US011505797B2

(12) United States Patent
Kmiec et al.

(10) Patent No.: US 11,505,797 B2
(45) Date of Patent: Nov. 22, 2022

(54) **GENE KNOCKOUT OF VARIANT *NRF2* FOR TREATMENT OF CANCER**

(71) Applicant: Christiana Care Health Services, Inc., Newark, DE (US)

(72) Inventors: Eric Kmiec, Middletown, DE (US); Pawel Bialk, Wilmington, DE (US)

(73) Assignee: Christiana Care Health Services, Inc., Newark, DE (US)

( * ) Notice: Subject to any disclaimer, the term of this patent is extended or adjusted under 35 U.S.C. 154(b) by 300 days.

(21) Appl. No.: 16/882,093

(22) Filed: May 22, 2020

(65) Prior Publication Data

US 2020/0370041 A1 Nov. 26, 2020

Related U.S. Application Data

(60) Provisional application No. 62/852,123, filed on May 23, 2019.

(51) Int. Cl.
| | |
|---|---|
| *C12N 15/11* | (2006.01) |
| *A61K 48/00* | (2006.01) |
| *A61P 35/00* | (2006.01) |
| *C12N 9/22* | (2006.01) |
| *C12N 15/85* | (2006.01) |
| *A61K 38/00* | (2006.01) |
| *C12N 15/113* | (2010.01) |
| *A61K 38/46* | (2006.01) |
| *C12N 15/90* | (2006.01) |
| *A61K 31/7088* | (2006.01) |

(52) U.S. Cl.
CPC ............ *C12N 15/11* (2013.01); *A61K 48/005* (2013.01); *A61P 35/00* (2018.01); *C12N 9/22* (2013.01); *C12N 15/85* (2013.01); *A61K 38/00* (2013.01); *C12N 2310/20* (2017.05); *C12N 2800/80* (2013.01)

(58) Field of Classification Search
None
See application file for complete search history.

(56) References Cited

FOREIGN PATENT DOCUMENTS

| CN | 106520772 | 3/2017 |
|---|---|---|
| WO | 2016/161207 | 10/2016 |
| WO | 2017/201497 | 11/2017 |
| WO | 2017/201527 | 11/2017 |
| WO | 2018/009525 | 1/2018 |
| WO | 2019/016772 | 1/2019 |

OTHER PUBLICATIONS

International Preliminary Report on Patentability pertaining to co-pending International Application No. PCT/US2020/034369, dated Nov. 16, 2021—pp. 1-9.

F.C. Passero et al., "Combinatorial ixazomib and belinostat therapy induces NFE2L2-dependent apoptosis in Hodgkin and T-cell lymphoma", BJH British Journal of Haematology, Jun. 13, 2019, John Wiley & Sons, Ltd.

S. Menogen et al., "The Dual Roles of NRF2 in Cancer", Trends in Molecular Medicine, Jul. 2016, vol. 22, No. 7, Elsevier Ltd.

P. Bialk et al., "Functional Gene Knockout of NRF2 Increases Chemosensitivity of Human Lung Cancer A549 Cells InVitro and in a Xenograft Mouse Model", Molecular Therapy Oncolytics, Dec. 2018, vol. 11.

H. Cho et al., "Functional Polymorphisms in NRF2: Implications For Human Disease", Free Radical Biology And Medicine, 2015, vol. 88, 362-372.

T. Shibata et al., "Cancer Related Mutations in NRF2 Impair Its Recognition By Keap1-Cul3 E3 Ligase And Promote Malignancy", PNAS, Sep. 9, 2008, vol. 105, No. 36.

J. Shao et al., "Impact of NRF2 On Tumour Growth and Drug Sensitivity in Oncogenic K-ras-Transformed Cells In Vitro and In Vivo", Free Radical Research, 2018, vol. 52, No. 6, 661-671.

C. Sun et al., "Oligomeric proanthocyanidins protects A549 cells against H2O2-induced oxidative stress via the Nrf2-ARE pathway", International Journal of Molecular Medicine, 39:1548-1554, 2017.

M. Gong et al., "Stable knockout of NRF2 gene in human A549 lung cancer cells by CRISPR/Cas9 system and its functional research", China Oncology, 2019 vol. 29 No. 11.

K. Banas et al., "Temporal analyses of CRISPR-directed gene editing on NRF2, a clinically relevant human gene involved in chemoresistance", BioRxiv, Oct. 10, 2019, http://dx.doi.org/10.1101/799676.

J. Strich et al., "CRISPR-Cas Biology and Its Application to Infectious Diseases", Journal of Clinical Microbiology, Apr. 2019, vol. 57, Issue 4, 1-14.

(Continued)

*Primary Examiner* — Suzanne M Noakes
*Assistant Examiner* — Jae W Lee
(74) *Attorney, Agent, or Firm* — McCarter & English, LLP

(57) ABSTRACT

The disclosure provides a guide RNA (gRNA) comprising a DNA-binding domain and a Clustered Regularly Interspaced Short Palindromic Repeat (CRISPR)-associated endonuclease protein-binding domain, wherein the DNA-binding domain is complementary to a target domain from a variant NRF2 gene found in a cancer cell but not in a non-cancerous cell. The disclosure also provides nucleic acid sequence encoding the gRNA. The disclosure further provides a method of treating cancer in a subject comprising administering to the subject a therapeutically effective amount of a pharmaceutical composition comprising a Clustered Regularly Interspaced Short Palindromic Repeat (CRISPR)-associated endonuclease and a guide RNA that is complementary to a target domain from a variant NRF2 gene in the subject. Methods of treating cancer comprising administering a pharmaceutical composition comprising: a DNA sequence encoding a guide RNA that is complementary to a target domain from a variant NRF2 gene in the subject; and a nucleic acid sequence encoding a Clustered Regularly Interspaced Short Palindromic Repeat (CRISPR)-associated endonuclease, are also provided.

8 Claims, 39 Drawing Sheets

Specification includes a Sequence Listing.

(56) References Cited

OTHER PUBLICATIONS

Eric B. Kmiec (2019) "CRISPR-Directed Gene Editing in a Community Cancer Center", Oncology Issues, 34:1, 30-37.
S. Wert et al., "Transcriptional Elements from the Human SP-C Gene Direct Expression in the Primordial Respiratory Epithelium of Transgenic Mice", Developmental Biology, 156, 426-443, 1993.
B. Davidson et al., "A model system for in vivo gene transfer into the central nervous system using an adenoviral vector", Nature Genetics, vol. 3, Mar. 1993, 219-223.
A. Anchini et al., "The non-small cell lung cancer immune landscape: emerging complexity, prognostic relevance and prospective significance in the context of immunotherapy", Cancer Immunology, Immunotherapy (2018) 67:1011-1022.
G. Le Gal La Salle et al., "An Adenovirus Vector for Gene Transfer into Neurons and Glia in the Brain", Science, Feb. 12, 1993, New Series, vol. 259, No. 5097 (Feb. 12, 1993), pp. 988-990.
M. Kaplitt et al., "Long-term gene expression and phenotypic correction using adena-associated virus vectors in the mammalian brain", Nature Genetics vol. 8 Oct. 1994.
E. Batrakova et al., "Using exosomes, naturally-equipped nanocarriers, for drug delivery", Journal of Controlled Release 219 (2015) 396-405.
A. Hayden et al., "The Nrf2 transcription factor contributes to resistance to cisplatin in bladder cancer", Urologic Oncology: Seminars and Original Investigations 32 (2014) 806-814.
Y. Zhou et al., "Adenovirus-delivered wwox inhibited lung cancer growth in vivo in a mouse model", Cancer Gene Therapy (2016) 23, 1-6.
P. Pandey et al., "The see-saw of Keap1-Nrf2 pathway in cancer", Critical Reviews in Oncology/Hematology 116 (2017) 89-98.
S. Menegon et al., "The Dual Roles of NRF2 in Cancer", Trends in Molecular Medicine, Jul. 2016, vol. 22, No. 7, 578-93.
Y. Zhou et al., "Over-expression of PDGF-C using a lung specific promoter results in abnormal lung development", Transgenic Res (2006) 15:543-555.
Q. Li et al., "Molecular Characterization of the Promoter Region of a Neuroendocrine Tumor Marker, IA-1", Biochemical and Biophysical Research Communications 236, 776-781 (1997).
S. Murakami et al., "Roles of Nrf2 in cell proliferation and differentiation", FreeRadicalBiologyandMedicine88(2015) 168-178.
S. Kim et al., "Cancer-derived exosomes as a delivery platform of CRISPR/Cas9 confer cancer cell tropism-dependent targeting", Journal of Controlled Release 266 (2017) 8-16.
M.D. Hellmann, "Chemotherapy remains an essential element of personalized care for persons with lung cancers", Annals of Oncology 27: 1829-1835, 2016.
A. Bianco et al., "Targeting immune checkpoints in non small cell lung cancer", Current Opinion in Pharmacology 2018, 40:46-50.
M. Rosenfeld et al., "In Vivo Transfer of the Human Cystic Fibrosis Transmembrane Conductance Regulator Gene to the Airway Epithelium", Cell, vol. 68, 143-155, Jan. 10, 1992.
K. Makarova et al., "Evolutionary classification of CRISPR-Cas systems: a burst of class 2 and derived variants", Nature Reviews Microbiology, vol. 18, Feb. 2020.
A. Singh et al., "Gain of Nrf2 Function in Non-Small-Cell Lung Cancer Cells Confers Radioresistance", Antioxidants & Redox Signaling, vol. 13, No. 11, 2010, 1627-1637.
T. Scholzen et al., "The Ki-67 Protein: From the Known and the Unknown", Journal of Cellular Physiology 182:311-322 (2000).
V. Velma et al., "Low Doses of Cisplatin Induce Gene Alterations, Cell Cycle Arrest, and Apoptosis in Human Promyelocytic Leukemia Cells", Biomarker Insights 2016:11, 113-121.
Y. Mitsuishi et al., "Nrf2 Redirects Glucose and Glutamine into Anabolic Pathways in Metabolic Reprogramming", Cancer Cell 22, 66-79, Jul. 10, 2012.
A. Geller et al., "Long-term increases in neurotransmitter release from neuronal cells expressing a constitutively active adenylate cyclase from a herpes simplex virus type 1 vector", Proc. Natl. Acad. Sci., vol. 90, pp. 7603-7607, Aug. 1993.
A. Geller et al., "Infection of cultured central nervous system neurons with a defective herpes simplex virus 1 vector results in stable expression of *Escherichia coli* beta-galactosidase", Proc. Natl. Acad. Sci., vol. 87, pp. 1149-1153, Feb. 1990.
Y. Fu et al., "Improving CRISPR-Cas nuclease specificity using truncated guide RNAs", Nat Biotechnol. Mar. 2014 ; 32(3): 279-284.
L. Torrente et al., "Crosstalk between NRF2 and HIPK2 shapes cytoprotective responses", Oncogene (2017) 36, 6204-6212.
B. Quantin et al., "Adenovirus as an expression vector in muscle cells in vivo", Proc. Nadl. Acad., vol. 89, pp. 2581-2584, Apr. 1992.
B. Jung et al., "Dysregulation of NRF2 in Cancer: from Molecular Mechanisms to Therapeutic Opportunities", Biomol Ther 26(1), 57-68 (2018).
H. Funaki et al., "Localization and expression of AQP5 in cornea, serous salivary glands, and pulmonary epithelial cells", Am J Physiol, 275, C1151-1157, 1998.
T. Fukutomi et al., "Kinetic, Thermodynamic, and Structural Characterizations of the Association between Nrf2-DLGex Degron and Keap1", Molecular and Cellular Biology, Mar. 2014, vol. 34, No. 5, 832-846.
N. Sanjana et al., "Improved vectors and genome-wide libraries for CRISPR screening", Nat Methods. Aug. 2014 ; 11(8): 783-784.
H. Kitamura et al., "NRF2 addiction in cancer cells", Cancer Science. 2018;109:900-911.
M. Kerins et al., "A catalogue of somatic NRF2 gain of-function mutations in cancer", Scientific Reports, (2018) 8:12846.
A. Geller et al., "An HSV-1 Vector Expressing Tyrosine Hydroxylase Causes Production and Release of L-DOPA from Cultured Rat Striatal Cells", J Neurochem. Feb. 1995 ; 64(2): 487-496.
F.P. Fabrizio et al., "Epigenetic versus Genetic Deregulation of the KEAP1/NRF2 Axis in Solid Tumors: Focus on Methylation and Noncoding RNAs", Oxidative Medicine and Cellular Longevity, vol. 2018, Article ID 2492063, 21 p.
Y. Chen et al., "Expression of ssDNA in Mammalian Cells", BioTechniques 34:167-171 (Jan. 2003).
L. You et al,, "ONYX-015 Works Synergistically with Chemotherapy in Lung Cancer Cell Lines and Primary Cultures Freshly Made from Lung Cancer Patients", Cancer Research 60, 1009-1013, Feb. 15, 2000.
Y. Wang et al., "Beta1-Integrin Deletion From the Lens Activates Cellular Stress Responses Leading to Apoptosis and Fibrosis", IOVS, Aug. 2017, vol. 58, No. 10, 3896-3922.
T. Fukazawa et al., "Development of a Cancer-Targeted Tissue-Specific Promoter System", Cancer Research 64, 363-369, Jan. 1, 2004.
R. Frank et al., "Clinical and Pathological Characteristics of KEAP1- and NFE2L2-Mutated Non-Small Cell Lung Carcinoma (NSCLC)", Clinical Cancer Research, 2018, 3087-3097.
Y. Yang et al., "Cellular and Humoral Immune Responses to Viral Antigens Create Barriers to Lung-Directed Gene Therapy with Recombinant Adenoviruses", Journal of Virology, Apr. 1995, vol. 69, No. 4, 2004-2015.
M. Strayer et al., Pre- and Postnatal Lung Development, Maturation, and Plasticity Human surfactant protein B promoter in transgenic mice: temporal, spatial, and stimulus-responsive regulation, Am J Physiol Lung Cell Mol Physiol 282: L394-L404, 2002.
L.D. Stratford-Perricaudet et al., "Widespread long-term gene transfer to mouse skeletal muscles and heart", J Clin Invest. 1992;90(2):626-630.
B. Nounamo et al., "Myxoma Virus Optimizes Cisplatin for the Treatment of Ovarian Cancer In Vitro and in a Syngeneic Murine Dissemination Model", Molecular Therapy: Oncolytics vol. 6 Sep. 2017, 91-99.
A. Namani et al., "Modulation of NRF2 signaling pathway by nuclear receptors:Implications for cancer", Biochimica et Biophysica Acta 1843 (2014) 1875-1885.
D. Li et al., "Enhanced tumor suppression by adenoviral PTEN gene therapy combined with cisplatin chemotherapy in small-cell lung cancer", Cancer Gene Therapy (2013) 20, 251-259.
E. Koonin et al., "Diversity, classification and evolution of CRISPR-Cas systems", Curr Opin Microbiol. Jun. 2017 ; 37: 67-78.

(56) References Cited

OTHER PUBLICATIONS

P. Bialk et al., "Functional Gene Knockout of NRF2 Increases Chemosensitivity of Human Lung Cancer A549 Cells In Vitro and in a Xenograft Mouse Model", Molecular Therapy: Oncolytics vol. 11 Dec. 2018, 75-89.

J. Rock et al., "Airway basal stem cells: a perspective on their roles in epithelial homeostasis and remodeling", Disease Models & Mechanisms 3, 545-556 (2010), 545-556.

L. Marek et al., "Fibroblast Growth Factor (FGF) and FGF Receptor-Mediated Autocrine Signaling in Non-Small-Cell Lung Cancer Cells", Mol Pharmacol 75:196-207, 2009.

M. Bruno et al., "Lung cell-specific Expression of the Murine Surfactant Protein A (SP-A) Gene Is Mediated by Interactions between the SP-A Promoter and Thyroid Transcription Factor-1", The Journal of Biological Chemistry, vol. 270, No. 12, Mar. 24, 1995, 6531-6536.

J. Strich et al., "CRISPR-Cas Biology and Its Application to Infectious Diseases", Journal of Clinical Microbiology, vol. 57, Issue 4, Apr. 2019.

G. Simpson et al., "Cancer immunotherapy via combining oncolytic virotherapy with chemotherapy: recent advances", Oncolytic Virotherapy 2016:5 1-13.

T. Shibata et al., "Cancer related mutations in NRF2 impair its recognition by Keap1-Cul3 E3 ligase and promote malignancy", PNAS, Sep. 9, 2008, vol. 105, No. 36, 13568-13573.

T. Shibata et al., "NRF2 Mutation Confers Malignant Potential and Resistance to Chemoradiation Therapy in Advanced Esophageal Squamous Cancer", Neoplasia, vol. 13, No. 9, Sep. 2011, 864-873.

L. Ostrowski et al., "Targeting Expression of a Transgene to the Airway Surface Epithelium Using a Ciliated Cell-Specific Promoter", Molecular Therapy vol. 8, No. 4, Oct. 2003, 637-645.

J. Liu et al., "CRISPR-CasX is an RNA-dominated enzyme active for human genome editing", Nature. Feb. 2019 ; 566(7743): 218-223.

H. Kang et al., "HER2 confers drug resistance of human breast cancer cells through activation of NRF2 by direct interaction", Scientific Reports, 4:7201, 2014.

A. Cheung et al., "Specific targeting of point mutations in EGFR L858R-positive lung cancer by CRISPR/Cas9", Laboratory Investigation (2018) 98:968-976.

M. Wang et al., "UVA irradiation Enhances Brusatol-Mediated Inhibition of Melanoma Growth by Downregulation of the Nrf2-Mediated Antioxidant Response", Oxidative Medicine and Cellular Longevity, vol. 2018, Article ID 9742154, 15 pages.

B. Stripp et al., "cis-Acting Elements That Confer Lung Epithelial Cell Expression of the CC10 Gene", The Journal of Biological Chemistry, vol. 267, No. 21, Issue of Jul. 25, pp. 14703-14712, 1992.

M. Dong et al., "Advanced Malignant Pleural or Peritoneal Effusion in Patients Treated with Recombinant Adenovirus p53 Injection plus Cisplatin"; The Journal of International Medical Research, 2008; 36(6) 2.

Y. Chow et al., "Development of an epithelium-specific expression cassette with human DNA regulatory elements for transgene expression in lung airways", Proc. Natl. Acad. Sci., vol. 94, pp. 14695-14700, Dec. 1997.

E. Brinkman et al., "Easy quantitative assessment of genome editing by sequence trace decomposition", Nucleic Acids Research, 2014 1-8.

Sep. 4, 2020 International Search Report for corresponding PCT Appln. No. PCT/US2020/034369.

Sep. 4, 2020 International Written Opinion for corresponding PCT Appln. No. PCT/US2020/034369.

FIGURE 15

Summary of On-target Analysis

- Cell lines: H1703

CAAGATATAGATCTTGGAGTAAGTGG 23nt
AAGATATAGATCTTGGAGTAAGTGG 22nt
GATATAGATCTTGGAGTAAGTGG 20nt
TATAGATCTTGGAGTAAGTGG 18nt
ATAGATCTTGGAGTAAGTGG 17nt

|      | Experiment 1 | | Experiment 2 | |
|------|--------|------|--------|------|
|      | No cut | cut  | No cut | cut  |
| 17 nt | 98.0% | 1.5% | 97.7% | 1.6% |
| 18 nt | 97.4% | 1.9% | 96.6% | 2.6% |
| 20 nt | 98.4% | 0.8% | 96.2% | 2.9% |
| 22 nt | 98.2% | 1.2% | 96.5% | 2.3% |
| 23 nt | 95.8% | 3.4% | 95.2% | 3.8% |

- What to measure:
  - On target efficiencies

FIGURE 16

INDEL deconvolution of Exon 2 (Neh2) KO clones

SEQUENCE LISTING

```
<160> NUMBER OF SEQ ID NOS: 121

<210> SEQ ID NO 1
<211> LENGTH: 23
<212> TYPE: DNA
<213> ORGANISM: Artificial Sequence
<220> FEATURE:
<223> OTHER INFORMATION: Guide RNA recognition element

<400> SEQUENCE: 1
agctactctg gcccttatag tcc                                           23

<210> SEQ ID NO 2
<211> LENGTH: 23
<212> TYPE: RNA
<213> ORGANISM: Artificial Sequence
<220> FEATURE:
<223> OTHER INFORMATION: Guide RNA

<400> SEQUENCE: 2
ucgaugugac cgggaauauc agg                                           23

<210> SEQ ID NO 3
<211> LENGTH: 23
<212> TYPE: DNA
<213> ORGANISM: Artificial Sequence
<220> FEATURE:
<223> OTHER INFORMATION: Guide RNA recognition element

<400> SEQUENCE: 3
actaaatctg ccatacgttg tcc                                           23

<210> SEQ ID NO 4
<211> LENGTH: 23
<212> TYPE: RNA
<213> ORGANISM: Artificial Sequence
```

```
<220> FEATURE:
<223> OTHER INFORMATION: Guide RNA

<400> SEQUENCE: 4
ugauuuagac gguaugcaac agg                                             23

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
gtagtggtgc cttagagctt actcatcc                                        28

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
ctagcatggg cagtactcat gactaag                                         27

<210> SEQ ID NO 7
<211> LENGTH: 2446
<212> TYPE: DNA
<213> ORGANISM: Homo sapiens

<400> SEQUENCE: 7
gattaccgag tgccggggag cccggaggag ccgccgacgc agccgccacc gccgccgccg     60
ccgccaccag agccgccctg tccgcgccgc gcctcggcag ccggaacagg gccgccgtcg    120
gggagcccca acacacggtc cacagctcat catgatggac ttggagctgc cgccgccggg    180
actcccgtcc cagcaggaca tggatttgat tgacatactt tggaggcaag atatagatct    240
tggagtaagt cgagaagtat ttgacttcag tcagcgacgg aaagagtatg agctggaaaa    300
acagaaaaaa cttgaaaagg aaagacaaga acaactccaa aaggagcaag agaaagcctt    360
tttcgctcag ttacaactag atgaagagac aggtgaattt ctcccaattc agccagccca    420
gcacatccag tcagaaacca gtggatctgc caactactcc caggttgccc acattcccaa    480
atcagatgct ttgtactttg atgactgcat gcagcttttg gcgcagacat cccgtttgt     540 agatgacaat gaggtttctt cggctacgtt tcagtcactt gttcctgata ttcccggtca    600
catcgagagc ccagtcttca ttgctactaa tcaggctcag tcacctgaaa cttctgttgc    660
tcaggtagcc cctgttgatt tagacggtat gcaacaggac attgagcaag tttggggagga    720 gctattatcc attcctgagt tacagtgtct taatattgaa aatgacaagc tggttgagac    780
taccatggtt ccaagtccag aagccaaact gacagaagtt gacaattatc attttttactc    840 atctataccc tcaatggaaa agaagtagg taactgtagt ccacattttc ttaatgcttt    900
tgaggattcc ttcagcagca tcctctccac agaagacccc aaccagttga cagtgaactc    960
attaaattca gatgccacag tcaacacaga ttttggtgat gaatttttatt ctgctttcat   1020 agctgagccc agtatcagca acagcatgcc ctcacctgct actttaagcc attcactctc   1080
tgaacttcta aatgggccca ttgatgtttc tgatctatca ctttgcaaag ctttcaacca   1140
aaaccaccct gaaagcacag cagaattcaa tgattctgac tccggcattt cactaaacac   1200
```

```
aagtcccagt gtggcatcac cagaacactc agtggaatct tccagctatg agacacact     1260
acttggcctc agtgattctg aagtggaaga gctagatagt gcccctggaa gtgtcaaaca    1320
gaatggtcct aaaacaccag tacattcttc tggggatatg gtacaaccct tgtcaccatc    1380
tcaggggcag agcactcacg tgcatgatgc ccaatgtgag aacacaccag agaaagaatt    1440
gcctgtaagt cctggtcatc ggaaaacccc attcacaaaa gacaaacatt caagccgctt    1500
ggaggctcat ctcacaagag atgaacttag ggcaaaagct ctccatatcc cattccctgt    1560
agaaaaaatc attaacctcc ctgttgttga cttcaacgaa atgatgtcca aagagcagtt    1620
caatgaagct caacttgcat taattcggga tatacgtagg aggggtaaga ataaagtggc    1680
tgctcagaat tgcagaaaaa gaaaactgga aaatatagta gaactagagc aagatttaga    1740
tcatttgaaa gatgaaaaag aaaaattgct caaagaaaaa ggagaaaatg acaaaagcct    1800
tcacctactg aaaaaacaac tcagcacctt atatctcgaa gttttcagca tgctacgtga    1860
tgaagatgga aaaccttatt ctcctagtga atactccctg cagcaaacaa gagatggcaa    1920
tgttttcctt gttcccaaaa gtaagaagcc agatgttaag aaaaaactaga tttaggagga   1980
tttgaccttt tctgagctag ttttttttgta ctattatact aaaagctcct actgtgatgt    2040
gaaatgctca tactttataa gtaattctat gcaaatcat agccaaaact agtatagaaa     2100
ataatacgaa actttaaaaa gcattggagt gtcagtatgt tgaatcagta gtttcacttt    2160
aactgtaaac aatttcttag gacaccattt gggctagttt ctgtgtaagt gtaaatacta    2220
caaaaactta tttatactgt tcttatgtca tttgttatat tcatagattt atatgatgat    2280
atgacatctg gctaaaaaga aattattgca aaactaacca ctatgtactt ttttataaat    2340
actgtatgga caaaaaatgg catttttttat attaaattgt ttagctctgg caaaaaaaaa   2400
aaattttaag agctggtact aataaaggat tattatgact gttaaa                   2446
```

<210> SEQ ID NO 8
<211> LENGTH: 605
<212> TYPE: PRT
<213> ORGANISM: Homo sapiens

<400> SEQUENCE: 8

```
Met Met Asp Leu Glu Leu Pro Pro Gly Leu Pro Ser Gln Gln Asp
1               5                   10                  15

Met Asp Leu Ile Asp Ile Leu Trp Arg Gln Asp Ile Asp Leu Gly Val
            20                  25                  30

Ser Arg Glu Val Phe Asp Phe Ser Gln Arg Arg Lys Glu Tyr Glu Leu
        35                  40                  45

Glu Lys Gln Lys Lys Leu Glu Lys Glu Arg Gln Glu Gln Leu Gln Lys
    50                  55                  60

Glu Gln Glu Lys Ala Phe Ala Gln Leu Gln Leu Asp Glu Glu Thr
65                  70                  75                  80

Gly Glu Phe Leu Pro Ile Gln Pro Ala Gln His Ile Gln Ser Glu Thr
                85                  90                  95

Ser Gly Ser Ala Asn Tyr Ser Gln Val Ala His Ile Pro Lys Ser Asp
            100                 105                 110

Ala Leu Tyr Phe Asp Asp Cys Met Gln Leu Leu Ala Gln Thr Phe Pro
        115                 120                 125

Phe Val Asp Asp Asn Glu Val Ser Ser Ala Thr Phe Gln Ser Leu Val
    130                 135                 140

Pro Asp Ile Pro Gly His Ile Glu Ser Pro Val Phe Ile Ala Thr Asn
145                 150                 155                 160
```

-continued

```
Gln Ala Gln Ser Pro Glu Thr Ser Val Ala Gln Val Ala Pro Val Asp
                165                 170                 175

Leu Asp Gly Met Gln Gln Asp Ile Glu Gln Val Trp Glu Glu Leu Leu
            180                 185                 190

Ser Ile Pro Glu Leu Gln Cys Leu Asn Ile Glu Asn Asp Lys Leu Val
        195                 200                 205

Glu Thr Thr Met Val Pro Ser Pro Glu Ala Lys Leu Thr Glu Val Asp
    210                 215                 220

Asn Tyr His Phe Tyr Ser Ser Ile Pro Ser Met Glu Lys Glu Val Gly
225                 230                 235                 240

Asn Cys Ser Pro His Phe Leu Asn Ala Phe Glu Asp Ser Phe Ser Ser
                245                 250                 255

Ile Leu Ser Thr Glu Asp Pro Asn Gln Leu Thr Val Asn Ser Leu Asn
            260                 265                 270

Ser Asp Ala Thr Val Asn Thr Asp Phe Gly Asp Glu Phe Tyr Ser Ala
        275                 280                 285

Phe Ile Ala Glu Pro Ser Ile Ser Asn Ser Met Pro Ser Pro Ala Thr
    290                 295                 300

Leu Ser His Ser Leu Ser Glu Leu Leu Asn Gly Pro Ile Asp Val Ser
305                 310                 315                 320

Asp Leu Ser Leu Cys Lys Ala Phe Asn Gln Asn His Pro Glu Ser Thr
                325                 330                 335

Ala Glu Phe Asn Asp Ser Asp Ser Gly Ile Ser Leu Asn Thr Ser Pro
            340                 345                 350

Ser Val Ala Ser Pro Glu His Ser Val Glu Ser Ser Ser Tyr Gly Asp
        355                 360                 365

Thr Leu Leu Gly Leu Ser Asp Ser Glu Val Glu Glu Leu Asp Ser Ala
    370                 375                 380

Pro Gly Ser Val Lys Gln Asn Gly Pro Lys Thr Pro Val His Ser Ser
385                 390                 395                 400

Gly Asp Met Val Gln Pro Leu Ser Pro Ser Gln Gly Gln Ser Thr His
                405                 410                 415

Val His Asp Ala Gln Cys Glu Asn Thr Pro Glu Lys Glu Leu Pro Val
            420                 425                 430

Ser Pro Gly His Arg Lys Thr Pro Phe Thr Lys Asp Lys His Ser Ser
        435                 440                 445

Arg Leu Glu Ala His Leu Thr Arg Asp Glu Leu Arg Ala Lys Ala Leu
    450                 455                 460

His Ile Pro Phe Pro Val Glu Lys Ile Ile Asn Leu Pro Val Val Asp
465                 470                 475                 480

Phe Asn Glu Met Met Ser Lys Glu Gln Phe Asn Glu Ala Gln Leu Ala
                485                 490                 495

Leu Ile Arg Asp Ile Arg Arg Gly Lys Asn Lys Val Ala Ala Gln
            500                 505                 510

Asn Cys Arg Lys Arg Lys Leu Glu Asn Ile Val Glu Leu Glu Gln Asp
        515                 520                 525

Leu Asp His Leu Lys Asp Glu Lys Glu Lys Leu Leu Lys Glu Lys Gly
    530                 535                 540

Glu Asn Asp Lys Ser Leu His Leu Leu Lys Lys Gln Leu Ser Thr Leu
545                 550                 555                 560

Tyr Leu Glu Val Phe Ser Met Leu Arg Asp Glu Asp Gly Lys Pro Tyr
                565                 570                 575
```

```
Ser Pro Ser Glu Tyr Ser Leu Gln Gln Thr Arg Asp Gly Asn Val Phe
        580                 585                 590

Leu Val Pro Lys Ser Lys Lys Pro Asp Val Lys Lys Asn
        595                 600                 605

<210> SEQ ID NO 9
<211> LENGTH: 23
<212> TYPE: DNA
<213> ORGANISM: Artificial Sequence
<220> FEATURE:
<223> OTHER INFORMATION: Guide RNA

<400> SEQUENCE: 9
tcgatgtgac cgggaatatc agg                                              23

<210> SEQ ID NO 10
<211> LENGTH: 23
<212> TYPE: DNA
<213> ORGANISM: Artificial Sequence
<220> FEATURE:
<223> OTHER INFORMATION: Guide RNA

<400> SEQUENCE: 10
tgatttagac ggtatgcaac agg                                              23

<210> SEQ ID NO 11
<211> LENGTH: 23
<212> TYPE: DNA
<213> ORGANISM: Artificial Sequence
<220> FEATURE:
<223> OTHER INFORMATION: Guide RNA

<400> SEQUENCE: 11
aagtacaaag catctgattt ggg                                              23

<210> SEQ ID NO 12
<211> LENGTH: 23
<212> TYPE: DNA
<213> ORGANISM: Artificial Sequence
<220> FEATURE:
<223> OTHER INFORMATION: Guide RNA

<400> SEQUENCE: 12
agcatctgat ttgggaatgt ggg                                              23

<210> SEQ ID NO 13
<211> LENGTH: 23
<212> TYPE: DNA
<213> ORGANISM: Artificial Sequence
<220> FEATURE:
<223> OTHER INFORMATION: Guide RNA

<400> SEQUENCE: 13
tggatttgat tgacatactt tgg                                              23

<210> SEQ ID NO 14
<211> LENGTH: 23
<212> TYPE: DNA
<213> ORGANISM: Artificial Sequence
<220> FEATURE:
<223> OTHER INFORMATION: Guide RNA

<400> SEQUENCE: 14
gcttcttact tttgggaaca agg                                              23
```

```
<210> SEQ ID NO 15
<211> LENGTH: 25
<212> TYPE: DNA
<213> ORGANISM: Artificial Sequence
<220> FEATURE:
<223> OTHER INFORMATION: Guide RNA

<400> SEQUENCE: 15
tttgattgac atactttgga ggcaa                                              25

<210> SEQ ID NO 16
<211> LENGTH: 25
<212> TYPE: DNA
<213> ORGANISM: Artificial Sequence
<220> FEATURE:
<223> OTHER INFORMATION: Guide RNA

<400> SEQUENCE: 16
ttttccttgt tcccaaaagt aagaa                                              25

<210> SEQ ID NO 17
<211> LENGTH: 23
<212> TYPE: DNA
<213> ORGANISM: Artificial Sequence
<220> FEATURE:
<223> OTHER INFORMATION: Guide RNA recognition sequence

<400> SEQUENCE: 17
aaactaactg tatgaaacct ccc                                                23

<210> SEQ ID NO 18
<211> LENGTH: 23
<212> TYPE: RNA
<213> ORGANISM: Artificial Sequence
<220> FEATURE:
<223> OTHER INFORMATION: Guide RNA

<400> SEQUENCE: 18
uuugauugac auacuuugga ggg                                                23

<210> SEQ ID NO 19
<211> LENGTH: 23
<212> TYPE: DNA
<213> ORGANISM: Artificial Sequence
<220> FEATURE:
<223> OTHER INFORMATION: Guide RNA recognition element

<400> SEQUENCE: 19
gaatgaggtt ctagatatag acc                                                23

<210> SEQ ID NO 20
<211> LENGTH: 23
<212> TYPE: RNA
<213> ORGANISM: Artificial Sequence
<220> FEATURE:
<223> OTHER INFORMATION: Guide RNA

<400> SEQUENCE: 20
cuuacuccaa gaucuauauc ugg                                                23

<210> SEQ ID NO 21
<211> LENGTH: 23
<212> TYPE: DNA
<213> ORGANISM: Artificial Sequence
<220> FEATURE:
<223> OTHER INFORMATION: Guide RNA recognition sequence
```

```
<400> SEQUENCE: 21
tatgaaacct ccgttctata tcc                                              23

<210> SEQ ID NO 22
<211> LENGTH: 23
<212> TYPE: RNA
<213> ORGANISM: Artificial Sequence
<220> FEATURE:
<223> OTHER INFORMATION: Guide RNA

<400> SEQUENCE: 22
auacuuugga ggcaagauau agg                                              23

<210> SEQ ID NO 23
<211> LENGTH: 23
<212> TYPE: DNA
<213> ORGANISM: Artificial Sequence
<220> FEATURE:
<223> OTHER INFORMATION: Guide RNA recognition element

<400> SEQUENCE: 23
tccgttctat atctagaacc tcc                                              23

<210> SEQ ID NO 24
<211> LENGTH: 23
<212> TYPE: RNA
<213> ORGANISM: Artificial Sequence
<220> FEATURE:
<223> OTHER INFORMATION: Guide RNA

<400> SEQUENCE: 24
aggcaagaua uagaucuugg agg                                              23

<210> SEQ ID NO 25
<211> LENGTH: 23
<212> TYPE: DNA
<213> ORGANISM: Artificial Sequence
<220> FEATURE:
<223> OTHER INFORMATION: Guide RNA recognition element

<400> SEQUENCE: 25
ctatatctag aacctcattc acc                                              23

<210> SEQ ID NO 26
<211> LENGTH: 23
<212> TYPE: RNA
<213> ORGANISM: Artificial Sequence
<220> FEATURE:
<223> OTHER INFORMATION: Guide RNA

<400> SEQUENCE: 26
gauauagauc uuggaguaag ugg                                              23

<210> SEQ ID NO 27
<211> LENGTH: 23
<212> TYPE: DNA
<213> ORGANISM: Artificial Sequence
<220> FEATURE:
<223> OTHER INFORMATION: Guide RNA recognition element

<400> SEQUENCE: 27
actgacttca gtttatgaag acc                                              23

<210> SEQ ID NO 28
<211> LENGTH: 23
```

```
<212> TYPE: RNA
<213> ORGANISM: Artificial Sequence
<220> FEATURE:
<223> OTHER INFORMATION: Guide RNA

<400> SEQUENCE: 28
ugacugaagu caaauacuuc ugg                                               23

<210> SEQ ID NO 29
<211> LENGTH: 23
<212> TYPE: DNA
<213> ORGANISM: Artificial Sequence
<220> FEATURE:
<223> OTHER INFORMATION: Guide RNA recognition element

<400> SEQUENCE: 29
aagtagatca acattgactc gcc                                               23

<210> SEQ ID NO 30
<211> LENGTH: 23
<212> TYPE: RNA
<213> ORGANISM: Artificial Sequence
<220> FEATURE:
<223> OTHER INFORMATION: Guide RNA

<400> SEQUENCE: 30
uucaucuagu uguaacugag cgg                                               23

<210> SEQ ID NO 31
<211> LENGTH: 23
<212> TYPE: DNA
<213> ORGANISM: Artificial Sequence
<220> FEATURE:
<223> OTHER INFORMATION: Guide RNA recognition element

<400> SEQUENCE: 31
taagtggaca gagaagtaga tcc                                               23

<210> SEQ ID NO 32
<211> LENGTH: 23
<212> TYPE: RNA
<213> ORGANISM: Artificial Sequence
<220> FEATURE:
<223> OTHER INFORMATION: Guide RNA

<400> SEQUENCE: 32
auucaccugu cucuucaucu agg                                               23

<210> SEQ ID NO 33
<211> LENGTH: 23
<212> TYPE: DNA
<213> ORGANISM: Artificial Sequence
<220> FEATURE:
<223> OTHER INFORMATION: Guide RNA recognition element

<400> SEQUENCE: 33
gagtcaatgt tgatctactt ccc                                               23

<210> SEQ ID NO 34
<211> LENGTH: 23
<212> TYPE: RNA
<213> ORGANISM: Artificial Sequence
<220> FEATURE:
<223> OTHER INFORMATION: Guide RNA

<400> SEQUENCE: 34
```
cucaguuaca acuagaugaa ggg                                              23

<210> SEQ ID NO 35
<211> LENGTH: 23
<212> TYPE: DNA
<213> ORGANISM: Artificial Sequence
<220> FEATURE:
<223> OTHER INFORMATION: Guide RNA recognition element

<400> SEQUENCE: 35
acttaacccT ctttaagtgg acc                                              23

<210> SEQ ID NO 36
<211> LENGTH: 23
<212> TYPE: RNA
<213> ORGANISM: Artificial Sequence
<220> FEATURE:
<223> OTHER INFORMATION: Guide RNA

<400> SEQUENCE: 36
ugaauuggga gaaauucacc ugg                                              23

<210> SEQ ID NO 37
<211> LENGTH: 23
<212> TYPE: DNA
<213> ORGANISM: Artificial Sequence
<220> FEATURE:
<223> OTHER INFORMATION: Guide RNA recognition element

<400> SEQUENCE: 37
gttgatctac ttctctgtcc acc                                              23

<210> SEQ ID NO 38
<211> LENGTH: 23
<212> TYPE: RNA
<213> ORGANISM: Artificial Sequence
<220> FEATURE:
<223> OTHER INFORMATION: Guide RNA

<400> SEQUENCE: 38
caacuagaug aagagacagg ugg                                              23

<210> SEQ ID NO 39
<211> LENGTH: 23
<212> TYPE: DNA
<213> ORGANISM: Artificial Sequence
<220> FEATURE:
<223> OTHER INFORMATION: Guide RNA recognition element

<400> SEQUENCE: 39
tattatcgag gagggtttga acc                                              23

<210> SEQ ID NO 40
<211> LENGTH: 23
<212> TYPE: RNA
<213> ORGANISM: Artificial Sequence
<220> FEATURE:
<223> OTHER INFORMATION: Guide RNA

<400> SEQUENCE: 40
auaauagcuc cucccaaacu ugg                                              23

<210> SEQ ID NO 41
<211> LENGTH: 23
<212> TYPE: DNA
<213> ORGANISM: Homo sapiens

```
<400> SEQUENCE: 41
tttgattgac atactttgga ggg                                              23

<210> SEQ ID NO 42
<211> LENGTH: 23
<212> TYPE: DNA
<213> ORGANISM: Homo sapiens

<400> SEQUENCE: 42
cttactccaa gatctatatc tgg                                              23

<210> SEQ ID NO 43
<211> LENGTH: 23
<212> TYPE: DNA
<213> ORGANISM: Homo sapiens

<400> SEQUENCE: 43
atactttgga ggcaagatat agg                                              23

<210> SEQ ID NO 44
<211> LENGTH: 23
<212> TYPE: DNA
<213> ORGANISM: Homo sapiens

<400> SEQUENCE: 44
aggcaagata tagatcttgg agg                                              23

<210> SEQ ID NO 45
<211> LENGTH: 23
<212> TYPE: DNA
<213> ORGANISM: Homo sapiens

<400> SEQUENCE: 45
gatatagatc ttggagtaag tgg                                              23

<210> SEQ ID NO 46
<211> LENGTH: 23
<212> TYPE: DNA
<213> ORGANISM: Homo sapiens

<400> SEQUENCE: 46
tgactgaagt caaatacttc tgg                                              23

<210> SEQ ID NO 47
<211> LENGTH: 23
<212> TYPE: DNA
<213> ORGANISM: Homo sapiens

<400> SEQUENCE: 47
ttcatctagt tgtaactgag cgg                                              23

<210> SEQ ID NO 48
<211> LENGTH: 23
<212> TYPE: DNA
<213> ORGANISM: Homo sapiens

<400> SEQUENCE: 48
attcacctgt ctcttcatct agg                                              23

<210> SEQ ID NO 49
<211> LENGTH: 23
<212> TYPE: DNA
```

```
<213> ORGANISM: Homo sapiens

<400> SEQUENCE: 49
ctcagttaca actagatgaa ggg                                              23

<210> SEQ ID NO 50
<211> LENGTH: 23
<212> TYPE: DNA
<213> ORGANISM: Homo sapiens

<400> SEQUENCE: 50
tgaattggga gaaattcacc tgg                                              23

<210> SEQ ID NO 51
<211> LENGTH: 23
<212> TYPE: DNA
<213> ORGANISM: Homo sapiens

<400> SEQUENCE: 51
caactagatg aagagacagg tgg                                              23

<210> SEQ ID NO 52
<211> LENGTH: 23
<212> TYPE: DNA
<213> ORGANISM: Homo sapiens

<400> SEQUENCE: 52
ataatagctc ctcccaaact tgg                                              23

<210> SEQ ID NO 53
<211> LENGTH: 22
<212> TYPE: DNA
<213> ORGANISM: Artificial Sequence
<220> FEATURE:
<223> OTHER INFORMATION: Guide RNA recognition sequence

<400> SEQUENCE: 53
aaaaagcgag taatgttgat cc                                               22

<210> SEQ ID NO 54
<211> LENGTH: 23
<212> TYPE: RNA
<213> ORGANISM: Artificial Sequence
<220> FEATURE:
<223> OTHER INFORMATION: Guide RNA

<400> SEQUENCE: 54
uuuuucgcuc aguuacaacu agg                                              23

<210> SEQ ID NO 55
<211> LENGTH: 23
<212> TYPE: DNA
<213> ORGANISM: Artificial Sequence
<220> FEATURE:
<223> OTHER INFORMATION: Guide RNA recognition sequence

<400> SEQUENCE: 55
gttgatctac ttctctgtcc acc                                              23

<210> SEQ ID NO 56
<211> LENGTH: 23
<212> TYPE: RNA
<213> ORGANISM: Artificial Sequence
<220> FEATURE:
<223> OTHER INFORMATION: Guide RNA
```

```
<400> SEQUENCE: 56
caacuagaug aagagacagg ugg                                          23

<210> SEQ ID NO 57
<211> LENGTH: 23
<212> TYPE: DNA
<213> ORGANISM: Homo sapiens

<400> SEQUENCE: 57
tttttcgctc agttacaact agg                                          23

<210> SEQ ID NO 58
<211> LENGTH: 23
<212> TYPE: DNA
<213> ORGANISM: Homo sapiens

<400> SEQUENCE: 58
caactagatg aagagacagg tgg                                          23

<210> SEQ ID NO 59
<211> LENGTH: 23
<212> TYPE: DNA
<213> ORGANISM: Artificial Sequence
<220> FEATURE:
<223> OTHER INFORMATION: Guide RNA

<400> SEQUENCE: 59
caagatatag atcttggagt aag                                          23

<210> SEQ ID NO 60
<211> LENGTH: 22
<212> TYPE: DNA
<213> ORGANISM: Artificial Sequence
<220> FEATURE:
<223> OTHER INFORMATION: Guide RNA

<400> SEQUENCE: 60
aagatataga tcttggagta ag                                           22

<210> SEQ ID NO 61
<211> LENGTH: 20
<212> TYPE: DNA
<213> ORGANISM: Artificial Sequence
<220> FEATURE:
<223> OTHER INFORMATION: Guide RNA

<400> SEQUENCE: 61
gatatagatc ttggagtaag                                              20

<210> SEQ ID NO 62
<211> LENGTH: 18
<212> TYPE: DNA
<213> ORGANISM: Artificial Sequence
<220> FEATURE:
<223> OTHER INFORMATION: Guide RNA

<400> SEQUENCE: 62
tatagatctt ggagtaag                                                18

<210> SEQ ID NO 63
<211> LENGTH: 17
<212> TYPE: DNA
<213> ORGANISM: Artificial Sequence
<220> FEATURE:
```

```
<223> OTHER INFORMATION: Guide RNA

<400> SEQUENCE: 63
atagatcttg gagtaag                                                        17

<210> SEQ ID NO 64
<211> LENGTH: 23
<212> TYPE: DNA
<213> ORGANISM: Artificial Sequence
<220> FEATURE:
<223> OTHER INFORMATION: Guide RNA

<400> SEQUENCE: 64
tggaggcaag atatagatct tgg                                                 23

<210> SEQ ID NO 65
<211> LENGTH: 200
<212> TYPE: DNA
<213> ORGANISM: Artificial Sequence
<220> FEATURE:
<223> OTHER INFORMATION: ssDNA template

<400> SEQUENCE: 65
ttaaaaaaca tgagctctct ccttcctttt tttgtcttaa acataggaca tggatttgat          60
tgacatactt tggaggcaag atatagatct tggagtaagt ggagaagtat ttgacttcag         120
tcagcgacgg aaagagtatg agctggaaaa acagaaaaaa cttgaaaagg aaagacaaga        180
acaactccaa aaggagcaag                                                    200

<210> SEQ ID NO 66
<211> LENGTH: 23
<212> TYPE: DNA
<213> ORGANISM: Artificial Sequence
<220> FEATURE:
<223> OTHER INFORMATION: Guide RNA

<400> SEQUENCE: 66
tcgatgtgac cgggaatatc agg                                                 23

<210> SEQ ID NO 67
<211> LENGTH: 23
<212> TYPE: DNA
<213> ORGANISM: Artificial Sequence
<220> FEATURE:
<223> OTHER INFORMATION: Guide RNA

<400> SEQUENCE: 67
tgatttagac ggtatgcaac agg                                                 23

<210> SEQ ID NO 68
<211> LENGTH: 24
<212> TYPE: PRT
<213> ORGANISM: Homo sapiens

<400> SEQUENCE: 68

Val Ser Ser Ala Thr Phe Gln Ser Leu Val Pro Asp Ile Pro Gly His
1               5                   10                  15

Ile Glu Ser Pro Val Phe Ile Ala
            20

<210> SEQ ID NO 69
<211> LENGTH: 24
<212> TYPE: PRT
<213> ORGANISM: Homo sapiens
```

-continued

```
<400> SEQUENCE: 69

Val Ser Ser Ala Thr Phe Gln Ser Leu Val Pro Asp Ile Pro Gly His
1               5                   10                  15

Ile Glu Ser Pro Val Phe Ile Ala
            20

<210> SEQ ID NO 70
<211> LENGTH: 24
<212> TYPE: PRT
<213> ORGANISM: Homo sapiens

<400> SEQUENCE: 70

Val Ser Ser Ala Thr Phe Gln Ser Leu Val Pro Asp Ile Pro Gly His
1               5                   10                  15

Ile Glu Ser Pro Val Phe Ile Ala
            20

<210> SEQ ID NO 71
<211> LENGTH: 24
<212> TYPE: PRT
<213> ORGANISM: Homo sapiens

<400> SEQUENCE: 71

Val Ser Ser Ala Thr Phe Gln Ser Leu Val Pro Asp Ile Pro Gly His
1               5                   10                  15

Ile Glu Ser Pro Val Phe Ile Ala
            20

<210> SEQ ID NO 72
<211> LENGTH: 24
<212> TYPE: PRT
<213> ORGANISM: Homo sapiens

<400> SEQUENCE: 72

Val Ser Ser Ala Thr Phe Gln Ser Leu Val Pro Asp Ile Pro Gly His
1               5                   10                  15

Ile Glu Ser Pro Val Phe Ile Ala
            20

<210> SEQ ID NO 73
<211> LENGTH: 17
<212> TYPE: PRT
<213> ORGANISM: Homo sapiens

<400> SEQUENCE: 73

Ser Leu Val Pro Asp Ile Pro Gly His Ile Glu Ser Pro Val Phe Ile
1               5                   10                  15

Ala

<210> SEQ ID NO 74
<211> LENGTH: 24
<212> TYPE: PRT
<213> ORGANISM: Homo sapiens

<400> SEQUENCE: 74

Ser Val Ala Gln Val Ala Pro Val Asp Leu Asp Gly Met Gln Gln Asp
1               5                   10                  15

Ile Glu Gln Val Trp Glu Glu Leu
            20
```

```
<210> SEQ ID NO 75
<211> LENGTH: 24
<212> TYPE: PRT
<213> ORGANISM: Homo sapiens

<400> SEQUENCE: 75

Ser Val Ala Gln Val Ala Pro Val Asp Leu Asp Gly Met Gln Gln Asp
1               5                   10                  15

Ile Glu Gln Val Trp Glu Glu Leu
            20

<210> SEQ ID NO 76
<211> LENGTH: 24
<212> TYPE: PRT
<213> ORGANISM: Homo sapiens

<400> SEQUENCE: 76

Ser Val Ala Gln Val Ala Pro Val Asp Leu Asp Gly Met Gln Gln Asp
1               5                   10                  15

Ile Glu Gln Val Trp Glu Glu Leu
            20

<210> SEQ ID NO 77
<211> LENGTH: 24
<212> TYPE: PRT
<213> ORGANISM: Homo sapiens

<400> SEQUENCE: 77

Ser Val Ala Gln Val Ala Pro Val Asp Leu Asp Gly Met Gln Gln Asp
1               5                   10                  15

Ile Glu Gln Val Trp Glu Glu Leu
            20

<210> SEQ ID NO 78
<211> LENGTH: 24
<212> TYPE: PRT
<213> ORGANISM: Homo sapiens

<400> SEQUENCE: 78

Ser Val Ala Gln Val Ala Pro Val Asp Leu Asp Gly Met Gln Gln Asp
1               5                   10                  15

Ile Glu Gln Val Trp Glu Glu Leu
            20

<210> SEQ ID NO 79
<211> LENGTH: 24
<212> TYPE: PRT
<213> ORGANISM: Homo sapiens

<400> SEQUENCE: 79

Ser Val Ala Gln Val Ala Pro Val Asp Leu Asp Gly Met Gln Gln Asp
1               5                   10                  15

Ile Glu Gln Val Trp Glu Glu Leu
            20

<210> SEQ ID NO 80
<211> LENGTH: 55
<212> TYPE: DNA
<213> ORGANISM: Artificial Sequence
<220> FEATURE:
<223> OTHER INFORMATION: NRF2 KO clone

<400> SEQUENCE: 80
```
gctacgtttc agtcacttgt tcctgatatt cccggtcaca tcgagagccc agtct    55

<210> SEQ ID NO 81
<211> LENGTH: 46
<212> TYPE: DNA
<213> ORGANISM: Artificial Sequence
<220> FEATURE:
<223> OTHER INFORMATION: NRF2 KO clone

<400> SEQUENCE: 81
gctacgtttc agtcacttgt tcccggtcac atcgagagcc cagtct    46

<210> SEQ ID NO 82
<211> LENGTH: 46
<212> TYPE: DNA
<213> ORGANISM: Artificial Sequence
<220> FEATURE:
<223> OTHER INFORMATION: NRF2 KO clone

<400> SEQUENCE: 82
gctacgtttc agtcacttgt tcccggtcac atcgagagcc cagtct    46

<210> SEQ ID NO 83
<211> LENGTH: 55
<212> TYPE: DNA
<213> ORGANISM: Artificial Sequence
<220> FEATURE:
<223> OTHER INFORMATION: NRF2 KO clone

<400> SEQUENCE: 83
gctacgtttc agtcacttgt tcctgatatt cccggtcaca tcgagagccc agtct    55

<210> SEQ ID NO 84
<211> LENGTH: 55
<212> TYPE: DNA
<213> ORGANISM: Artificial Sequence
<220> FEATURE:
<223> OTHER INFORMATION: NRF2 KO clone

<400> SEQUENCE: 84
tagcccctgt tgatttagac ggtatgcaac aggacattga gcaagtttgg gagga    55

<210> SEQ ID NO 85
<211> LENGTH: 54
<212> TYPE: DNA
<213> ORGANISM: Artificial Sequence
<220> FEATURE:
<223> OTHER INFORMATION: NRF2 KO clone

<400> SEQUENCE: 85
tagcccctgt tgatttagac ggtatgaaca ggacattgag caagtttggg agga    54

<210> SEQ ID NO 86
<211> LENGTH: 49
<212> TYPE: DNA
<213> ORGANISM: Artificial Sequence
<220> FEATURE:
<223> OTHER INFORMATION: NRF KO clone

<400> SEQUENCE: 86
tagcccctgt tgatttagac ggtatgcaaa ttgagcaagt ttgggagga    49

<210> SEQ ID NO 87
<211> LENGTH: 45
<212> TYPE: DNA
<213> ORGANISM: Artificial Sequence

```
<220> FEATURE:
<223> OTHER INFORMATION: NRF2 KO clone

<400> SEQUENCE: 87
tagcccctgt tgatttagac ggtatattga gcaagtttgg gagga            45

<210> SEQ ID NO 88
<211> LENGTH: 77
<212> TYPE: DNA
<213> ORGANISM: Artificial Sequence
<220> FEATURE:
<223> OTHER INFORMATION: NRF2 KO clone

<400> SEQUENCE: 88
gtttcttcgg ctacgtttca gtcacttgtt cctgataaca ggacattgag caagtttggg    60
aggagctatt atccatt                                                   77

<210> SEQ ID NO 89
<211> LENGTH: 78
<212> TYPE: DNA
<213> ORGANISM: Artificial Sequence
<220> FEATURE:
<223> OTHER INFORMATION: NRF2 KO clone

<400> SEQUENCE: 89
gtttcttcgg ctacgtttca gtcacttgtt cctgataaac aggacattga gcaagtttgg    60
gaggagctat tatccatt                                                  78

<210> SEQ ID NO 90
<211> LENGTH: 92
<212> TYPE: DNA
<213> ORGANISM: Artificial Sequence
<220> FEATURE:
<223> OTHER INFORMATION: NRF2 KO clone

<400> SEQUENCE: 90
gtttcttcgg ctacgtttca gtcacttgtt cctgatattc ccggtcacat cgagagccca    60
gtcttcattg ctactaatca ggctcagtca cc                                  92

<210> SEQ ID NO 91
<211> LENGTH: 77
<212> TYPE: DNA
<213> ORGANISM: Artificial Sequence
<220> FEATURE:
<223> OTHER INFORMATION: NRF2 KO clone

<400> SEQUENCE: 91
gtttcttcgg ctacgtttca gtcacttgtt cctgataaca ggacattgag caagtttggg    60
aggagctatt atccatt                                                   77

<210> SEQ ID NO 92
<211> LENGTH: 78
<212> TYPE: DNA
<213> ORGANISM: Artificial Sequence
<220> FEATURE:
<223> OTHER INFORMATION: NRF2 KO clone

<400> SEQUENCE: 92
gtttcttcgg ctacgtttca gtcacttgtt cctgataaac aggacattga gcaagtttgg    60
gaggagctat tatccatt                                                  78

<210> SEQ ID NO 93
```

```
<211> LENGTH: 77
<212> TYPE: DNA
<213> ORGANISM: Artificial Sequence
<220> FEATURE:
<223> OTHER INFORMATION: NRF2 KO clone

<400> SEQUENCE: 93
gtttcttcgg ctacgtttca gtcacttgtt cctgataaca ggacattgag caagtttggg    60
aggagctatt atccatt                                                   77

<210> SEQ ID NO 94
<211> LENGTH: 78
<212> TYPE: DNA
<213> ORGANISM: Artificial Sequence
<220> FEATURE:
<223> OTHER INFORMATION: NRF2 KO clone

<400> SEQUENCE: 94
gtttcttcgg ctacgtttca gtcacttgtt cctgataaac aggacattga gcaagtttgg    60
gaggagctat tatccatt                                                  78

<210> SEQ ID NO 95
<211> LENGTH: 78
<212> TYPE: DNA
<213> ORGANISM: Artificial Sequence
<220> FEATURE:
<223> OTHER INFORMATION: NRF2 KO clone

<400> SEQUENCE: 95
gtttcttcgg ctacgtttca gtcacttgtt cctgatcaac aggacattga gcaagtttgg    60
gaggagctat tatccatt                                                  78

<210> SEQ ID NO 96
<211> LENGTH: 92
<212> TYPE: DNA
<213> ORGANISM: Artificial Sequence
<220> FEATURE:
<223> OTHER INFORMATION: NRF2 KO clone

<400> SEQUENCE: 96
gtttcttcgg ctacgtttca gtcacttgtt cctgatattc ccggtcacat cgagagccca    60
gtcttcattg ctactaatca ggctcagtca cc                                  92

<210> SEQ ID NO 97
<211> LENGTH: 76
<212> TYPE: DNA
<213> ORGANISM: Artificial Sequence
<220> FEATURE:
<223> OTHER INFORMATION: NRF2 KO clone

<400> SEQUENCE: 97
gtttcttcgg ctacgtttca gtcacttgtt cctgcaacag gacattgagc aagtttggga    60
ggagctatta tccatt                                                    76

<210> SEQ ID NO 98
<211> LENGTH: 79
<212> TYPE: DNA
<213> ORGANISM: Artificial Sequence
<220> FEATURE:
<223> OTHER INFORMATION: NRF2 KO clone

<400> SEQUENCE: 98
gtttcttcgg ctacgtttca gtcacttgtt cctgatacaa caggacattg agcaagtttg    60
```
ggaggagcta ttatccatt                                                    79

<210> SEQ ID NO 99
<211> LENGTH: 67
<212> TYPE: DNA
<213> ORGANISM: Artificial Sequence
<220> FEATURE:
<223> OTHER INFORMATION: NRF2 KO clone

<400> SEQUENCE: 99
gtttcttcgg ctacgtttca gtcacttgtt cctgattgag caagtttggg aggagctatt     60
atccatt                                                                67

<210> SEQ ID NO 100
<211> LENGTH: 78
<212> TYPE: DNA
<213> ORGANISM: Artificial Sequence
<220> FEATURE:
<223> OTHER INFORMATION: NRF2 KO clone

<400> SEQUENCE: 100
gtttcttcgg ctacgtttca gtcacttgtt cctgataaac aggacattga gcaagtttgg     60
gaggagctat tatccatt                                                    78

<210> SEQ ID NO 101
<211> LENGTH: 92
<212> TYPE: DNA
<213> ORGANISM: Artificial Sequence
<220> FEATURE:
<223> OTHER INFORMATION: NRF2 KO clone

<400> SEQUENCE: 101
gtttcttcgg ctacgtttca gtcacttgtt cctgatattc ccggtcacat cgagagccca     60
gtcttcattg ctactaatca ggctcagtca cc                                    92

<210> SEQ ID NO 102
<211> LENGTH: 76
<212> TYPE: DNA
<213> ORGANISM: Artificial Sequence
<220> FEATURE:
<223> OTHER INFORMATION: NRF2 KO clone

<400> SEQUENCE: 102
gtttcttcgg ctacgtttca gtcacttgtt cctgcaacag gacattgagc aagtttggga     60
ggagctatta tccatt                                                      76

<210> SEQ ID NO 103
<211> LENGTH: 77
<212> TYPE: DNA
<213> ORGANISM: Artificial Sequence
<220> FEATURE:
<223> OTHER INFORMATION: NRF2 KO clone

<400> SEQUENCE: 103
gtttcttcgg ctacgtttca gtcacttgtt cctgataaca ggacattgag caagtttggg     60
aggagctatt atccatt                                                     77

<210> SEQ ID NO 104
<211> LENGTH: 78
<212> TYPE: DNA
<213> ORGANISM: Artificial Sequence
<220> FEATURE:

```
<223> OTHER INFORMATION: NRF2 KO clone

<400> SEQUENCE: 104
gtttcttcgg ctacgtttca gtcacttgtt cctgataaac aggacattga gcaagtttgg     60
gaggagctat tatccatt                                                   78

<210> SEQ ID NO 105
<211> LENGTH: 78
<212> TYPE: DNA
<213> ORGANISM: Artificial Sequence
<220> FEATURE:
<223> OTHER INFORMATION: NRF2 KO clone

<400> SEQUENCE: 105
gtttcttcgg ctacgtttca gtcacttgtt cctgatcaac aggacattga gcaagtttgg     60
gaggagctat tatccatt                                                   78

<210> SEQ ID NO 106
<211> LENGTH: 84
<212> TYPE: DNA
<213> ORGANISM: Artificial Sequence
<220> FEATURE:
<223> OTHER INFORMATION: NRF2 KO clone

<400> SEQUENCE: 106
gtcgagaagt atttgacttc agtcagacgg aaagagtatg agctgaaaaa cagaaaaaac     60
ttgaaaagga aagacaagaa caac                                            84

<210> SEQ ID NO 107
<211> LENGTH: 84
<212> TYPE: DNA
<213> ORGANISM: Artificial Sequence
<220> FEATURE:
<223> OTHER INFORMATION: NRF2 KO clone

<400> SEQUENCE: 107
gtcgagaagt atttgacttc agtccgacgg aaagagtatg agctgaaaaa cagaaaaaac     60
ttgaaaagga aagacaagaa caac                                            84

<210> SEQ ID NO 108
<211> LENGTH: 73
<212> TYPE: DNA
<213> ORGANISM: Artificial Sequence
<220> FEATURE:
<223> OTHER INFORMATION: NRF2 KO clone

<400> SEQUENCE: 108
gtcgagaagt atttgacttc aggagtatga gctgaaaaac agaaaaaact tgaaaaggaa     60
agacaagaac aac                                                        73

<210> SEQ ID NO 109
<211> LENGTH: 85
<212> TYPE: DNA
<213> ORGANISM: Artificial Sequence
<220> FEATURE:
<223> OTHER INFORMATION: NRF2 KO clone

<400> SEQUENCE: 109
gtcgagaagt atttgacttc agtcacgacg gaaagagtat gagctgaaaa acagaaaaaa     60
cttgaaaagg aaagacaaga acaac                                           85
```

<210> SEQ ID NO 110
<211> LENGTH: 84
<212> TYPE: DNA
<213> ORGANISM: Artificial Sequence
<220> FEATURE:
<223> OTHER INFORMATION: NRF2 KO clone

<400> SEQUENCE: 110

```
gtcgagaagt atttgacttc agtccgacgg aaagagtatg agctgaaaaa cagaaaaaac    60
ttgaaaagga aagacaagaa caac                                           84
```

<210> SEQ ID NO 111
<211> LENGTH: 143
<212> TYPE: DNA
<213> ORGANISM: Homo sapiens

<400> SEQUENCE: 111

```
taggacatgg atttgattga catactttgg aggcaagata tagatcttgg agtaagtgga    60
gaagtatttg acttcagtca gcgacggaaa gagtatgagc tggaaaaaca gaaaaaactt   120
gaaaaggaaa gacaagaaca act                                           143
```

<210> SEQ ID NO 112
<211> LENGTH: 47
<212> TYPE: PRT
<213> ORGANISM: Homo sapiens

<400> SEQUENCE: 112

```
Asp Met Asp Leu Ile Asp Ile Leu Trp Arg Gln Asp Ile Asp Leu Gly
1               5                   10                  15

Val Ser Gly Glu Val Phe Asp Phe Ser Gln Arg Arg Lys Glu Tyr Glu
            20                  25                  30

Leu Glu Lys Gln Lys Lys Leu Glu Lys Glu Arg Gln Gln Gln Leu
        35                  40                  45
```

<210> SEQ ID NO 113
<211> LENGTH: 159
<212> TYPE: DNA
<213> ORGANISM: Homo sapiens

<400> SEQUENCE: 113

```
gacatggatt tgaatgacat actttggagg caagatatag atcttggagt aagtcgagaa    60
gtatttgact tcagtcagcg acggaaagag tatgagctgg aaaaacagaa aaacttgaa   120 aaggaaagac aagaacaact ccaaaaggag caagagaaa                          159
```

<210> SEQ ID NO 114
<211> LENGTH: 159
<212> TYPE: DNA
<213> ORGANISM: Homo sapiens

<400> SEQUENCE: 114

```
gacatggatt tgaatgacat actttggagg caagatatag atcttggagt aagtsgagaa    60
gtatttgact tcagtcagsg acggaaagag tatgagctgg aaaaacagaa aaacttgaa   120 aaggaaagac aagaacaact ccaaaaggag caagagaaa                          159
```

<210> SEQ ID NO 115
<211> LENGTH: 159
<212> TYPE: DNA
<213> ORGANISM: Homo sapiens

<400> SEQUENCE: 115

```
gacatggatt tgaatgacat actttggagg caagatatag atcttggagt aagtcgagaa    60
gtatttgact tcagtcagcg acggaaagag tatgagctgg aaaaacagaa aaaacttgaa   120
aaggaaagac aagaacaact ccaaaaggag caagagaaa                          159
```

```
<210> SEQ ID NO 116
<211> LENGTH: 79
<212> TYPE: DNA
<213> ORGANISM: Artificial Sequence
<220> FEATURE:
<223> OTHER INFORMATION: NRF2 KO clone

<400> SEQUENCE: 116
ctttggaggc aagatatagt ggagtaagtg gagaagtatt tgacttcagt cagcgacgga    60
aagagtatga gctggaaaa                                                79
```

```
<210> SEQ ID NO 117
<211> LENGTH: 81
<212> TYPE: DNA
<213> ORGANISM: Artificial Sequence
<220> FEATURE:
<223> OTHER INFORMATION: NRF2 KO clone

<400> SEQUENCE: 117
ctttggaggc aagatataga ttggagtaag tggagaagta tttgacttca gtcagcgacg    60
gaaagagtat gagctggaaa a                                             81
```

```
<210> SEQ ID NO 118
<211> LENGTH: 77
<212> TYPE: DNA
<213> ORGANISM: Artificial Sequence
<220> FEATURE:
<223> OTHER INFORMATION: NRF2 KO clone

<400> SEQUENCE: 118
ctttggaggc aagatcttgg agtaagtcga gaagtatttg acttcagtca gcgacggaaa    60
gagtatgagc tggaaaa                                                  77
```

```
<210> SEQ ID NO 119
<211> LENGTH: 79
<212> TYPE: DNA
<213> ORGANISM: Artificial Sequence
<220> FEATURE:
<223> OTHER INFORMATION: NRF KO clone

<400> SEQUENCE: 119
ctttggaggc aagatataga ggagtaagtc gagaagtatt tgacttcagt cagcgacgga    60
aagagtatga gctggaaaa                                                79
```

```
<210> SEQ ID NO 120
<211> LENGTH: 84
<212> TYPE: DNA
<213> ORGANISM: Artificial Sequence
<220> FEATURE:
<223> OTHER INFORMATION: NRF2 KO clone

<400> SEQUENCE: 120
acatactttg gaggcaagat atagatcttg gagtaagtgc gagaagtatt tgacttcagt    60
cagcgacgga aagagtatga gctg                                          84
```

```
<210> SEQ ID NO 121
```

```
<211> LENGTH: 63
<212> TYPE: DNA
<213> ORGANISM: Artificial Sequence
<220> FEATURE:
<223> OTHER INFORMATION: NRF2 KO clone

<400> SEQUENCE: 121
acatactttg gagtaagtcg agaagtattt gacttcagtc agcgacggaa agagtatgag      60
ctg                                                                   63
```

GENE KNOCKOUT OF VARIANT *NRF2* FOR TREATMENT OF CANCER

RELATED APPLICATIONS

This application claims the benefit of U.S. Provisional Application 62/852,123, filed May 23, 2019, which is incorporated herein, in its entirety, by reference.

SEQUENCE LISTING

The sequence Listing associated with this application is filed in electronic format via EFS-Web and is hereby incorporated by reference into the specification in its entirety. The name of the text file containing the Sequence Listing is 130949_00201_SEQUENCELISTING.TXT. The size of the text file is 35 KB, and the text file was created on Jun. 21, 2022.

FIELD

The present disclosure relates to compositions and methods for knocking out a variant NRF2 found in certain cancers to treat such cancer using Clustered Regularly Interspaced Short Palindromic Repeat (CRISPR)/endonuclease gene editing.

BACKGROUND

Cancer is presently one of the leading causes of death in developed nations. A diagnosis of cancer traditionally involves serious health complications. Cancer can cause disfigurement, chronic or acute pain, lesions, organ failure, or even death. Commonly diagnosed cancers include lung cancer, pancreatic cancer, breast cancer, melanoma, lymphoma, carcinoma, sarcoma leukemia, endometrial cancer, colon and rectal cancer, prostate cancer, and bladder cancer. Traditionally, many cancers are treated with surgery, chemotherapy, radiation, or combinations thereof.

Nuclear factor (erythroid-derived 2)-like 2, also known as NFE2L2 or NRF2, is a transcription factor that in humans is encoded by the NFE2L2 gene. NRF2 is a basic leucine zipper (bZIP) protein that regulates the expression of antioxidant proteins that protect against oxidative damage triggered by injury and inflammation.

A recent study catalogued somatic NRF2 mutations in various cancer cases reported in The Cancer Genome Atlas. Kerins, M. J. & Ooi, A, *Sci. Rep.* 8, Article No. 12846 (2018). This study identified the percentage of NRF2 and KEAP1 mutations found across 33 different tumor types as well as the common mutations responsible for constitutive NRF2 activation. The study reported 214 cases of NRF2 mutations, with the most cases seen in Lung Squamous Cell Carcinoma. The NRF2 mutations commonly seen among the tumor types are found within the Neh2 Domain of the protein, which is known as the KEAP1 binding domain. KEAP1 is a negative regulator of NRF2 and mediates NRF2 degradation under basal conditions. The mutations reported in the study cause loss of KEAP1 binding and lead to constitutive expression of NRF2 in cancerous cells. The most common mutation reported in LUSC, R34G, is especially of interest because this mutation forms a new PAM site for Cas9 recognition. The first base of codon 34 in NRF2 is mutated from cytosine to guanine. This new PAM site allows for differentiation of cancerous and noncancerous cells. There have been several other mutations reported within the Neh2 Domain of NRF2, which form new PAM sites as well. Frank, R. et al., *Clin. Cancer Res.* 24:3087-96 (2018); Menegon, S., Columbano, A. & Giordano, S. The Dual Roles of NRF2 in Cancer. *Trends in Molecular Medicine* (2016); Shibata, T. et al., *Proc Natl Acad Sci USA* 105:13568-73 (2008). Similar experiments have been carried out using known mutations as new recognition sites for CRISPR/Cas9. Cheung, A. H. K. et al., *Lab. Investig.* 98:968-76 (2018).

Chemotherapeutic agents used in the treatment of cancer are known to produce several serious and unpleasant side effects in patients. For example, some chemotherapeutic agents cause neuropathy, nephrotoxicity, stomatitis, alopecia, decreased immunity, anemia, cardiotoxicity, fatigue, neuropathy, myelosuppression, or combinations thereof. Oftentimes, chemotherapy is not effective, or loses effectiveness after a period of efficacy, either during treatment, or shortly after the treatment regimen concludes.

Thus a need exists for improved methods of treating cancer.

SUMMARY

One aspect is for a method of reducing NRF2 expression or activity in a cancer cell comprising introducing into the cancer cell (a) one or more DNA sequences encoding one or more guide RNAs (gRNAs) that are complementary to one or more target sequences in a variant NRF2 gene and (b) a nucleic acid sequence encoding a Clustered Regularly Interspaced Short Palindromic Repeat (CRISPR)-associated endonuclease, whereby the one or more gRNAs hybridize to the variant NRF2 gene and the CRISPR-associated endonuclease cleaves the variant NRF2 gene, and wherein NRF2 expression or activity is reduced in the cancer cell relative to a cancer cell in which the one or more DNA sequences encoding the one or more gRNAs and the nucleic acid sequence encoding the CRISPR-associated endonuclease are not introduced. In some embodiments, the one or more gRNAs are complementary to a target sequence in exon 2 of the variant NRF2 gene. In some embodiments, the one or more gRNAs comprise a trans-activated small RNA (tracrRNA) and a CRISPR RNA (crRNA). In some embodiments, the one or more gRNAs are one or more single guide RNAs. In some embodiments, the CRISPR-associated endonuclease is a class 2 CRISPR-associated endonuclease, and in some embodiments, the class 2 CRISPR-associated endonuclease is Cas9 or Cas12a. In some embodiments, expression of one or more allele(s) of the variant NRF2 gene is reduced in the cancer cell. In some embodiments, NRF2 activity is reduced in the cancer cell. In some embodiments, NRF2 expression or activity is not completely eliminated in the cancer cell. In some embodiments, NRF2 expression or activity is completely eliminated in the cancer cell. In some embodiments, the cancer cell is a lung cancer cell; in some embodiments, the lung cancer cell is a non-small-cell lung cancer cell (NSCLC); and in some embodiments, the NSCLC is adenocarcinoma, squamous cell carcinoma, or large cell carcinoma. In some embodiments, expression or activity of wild-type NRF2 in a non-cancerous cell of a subject that contains the cancer cell is unaffected by the introduction of the one or more DNA sequences of (a) and the nucleic acid sequence of (b). In some embodiments, a variant NRF2 polypeptide encoded by the variant NRF2 gene in the cancer cell comprises one or more amino acid substitutions of (a) Q26E, D29G, V32G, R34G, F71S, Q75H, D77G, E79G, T80P, E82W, or E185D relative to SEQ ID NO:8; (b) Q26E, D29G, V32G, R34P, F71S, Q75H, D77G, E79G, T80P, E82W, or E185D relative to SEQ ID NO:8; (c) Q26P, D29G, V32G, R34G, F71S, Q75H, D77G, E79G, T80P, E82W, or E185D relative to SEQ ID NO:8; (d) Q26P, D29G, V32G, R34P, F71S, Q75H, D77G, E79G, T80P, E82W, or E185D relative to SEQ ID NO:8; (e) Q26E, D29G, V32G, R34G, F71S, Q75H, D77G, E79G, T80P, E82G, or E185D relative to SEQ ID NO:8; (f) Q26E, D29G, V32G, R34P, F71S, Q75H, D77G, E79G, T80P, E82G, or E185D relative to SEQ ID NO:8; (g) Q26P, D29G, V32G, R34G, F71S, Q75H, D77G, E79G, T80P, E82G, or E185D relative to SEQ ID NO:8; or (h) Q26P, D29G, V32G, R34P, F71S, Q75H, D77G, E79G, T80P, E82G, or E185D relative to SEQ ID NO:8. In some embodiments, the variant NRF2 gene comprises: (a) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (b) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (c) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (d) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (e) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (f) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (g) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; or (h) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7.

Another aspect is for a cancer cell comprising a mutated variant NRF2 gene produced by the aforementioned method.

A further aspect is for a method of reducing variant NRF2 expression or activity in a cancer cell comprising introducing into the cancer cell (a) one or more guide RNAs (gRNAs) that are complementary to one or more target sequences in the variant NRF2 gene and (b) a Clustered Regularly Interspaced Short Palindromic Repeat (CRISPR)-associated endonuclease, whereby the one or more gRNAs hybridize to the variant NRF2 gene and the CRISPR-associated endonuclease cleaves the variant NRF2 gene, and wherein variant NRF2 expression or activity is reduced in the cancer cell relative to a cancer cell in which the one or more gRNAs and the CRISPR-associated endonuclease are not introduced. In some embodiments, the one or more gRNAs are complementary to a target sequence in exon 2 of the variant NRF2 gene. In some embodiments, the one or more gRNAs comprise a trans-activated small RNA (tracrRNA) and a CRISPR RNA (crRNA). In some embodiments, the one or more gRNAs are one or more single guide RNAs. In some embodiments, the CRISPR-associated endonuclease is a class 2 CRISPR-associated endonuclease; and in some embodiments, the class 2 CRISPR-associated endonuclease is Cas9 or Cas12a. In some embodiments, expression of one or more allele(s) of the variant NRF2 gene is reduced in the cancer cell. In some embodiments, NRF2 activity is reduced in the cancer cell. In some embodiments, NRF2 expression or activity is not completely eliminated in the cancer cell. In some embodiments, NRF2 expression or activity is completely eliminated in the cancer cell. In some embodiments, the cancer cell is a lung cancer cell; in some embodiments, the lung cancer cell is a non-small-cell lung cancer cell (NSCLC); and in some embodiments, the NSCLC is adenocarcinoma, squamous cell carcinoma, or large cell carcinoma. In some embodiments, expression or activity of wild-type NRF2 in a non-cancerous cell of a subject that contains the cancer cell is unaffected by the introduction of the one or more DNA sequences of (a) and the nucleic acid sequence of (b). In some embodiments, a variant NRF2 polypeptide encoded by the variant NRF2 gene in the cancer cell comprises one or more amino acid substitutions of (a) Q26E, D29G, V32G, R34G, F71S, Q75H, D77G, E79G, T80P, E82W, or E185D relative to SEQ ID NO:8; (b) Q26E, D29G, V32G, R34P, F71S, Q75H, D77G, E79G, T80P, E82W, or E185D relative to SEQ ID NO:8; (c) Q26P, D29G, V32G, R34G, F71S, Q75H, D77G, E79G, T80P, E82W, or E185D relative to SEQ ID NO:8; (d) Q26P, D29G, V32G, R34P, F71S, Q75H, D77G, E79G, T80P, E82W, or E185D relative to SEQ ID NO:8; (e) Q26E, D29G, V32G, R34G, F71S, Q75H, D77G, E79G, T80P, E82G, or E185D relative to SEQ ID NO:8; (f) Q26E, D29G, V32G, R34P, F71S, Q75H, D77G, E79G, T80P, E82G, or E185D relative to SEQ ID NO:8; (g) Q26P, D29G, V32G, R34G, F71S, Q75H, D77G, E79G, T80P, E82G, or E185D relative to SEQ ID NO:8; or (h) Q26P, D29G, V32G, R34P, F71S, Q75H, D77G, E79G, T80P, E82G, or E185D relative to SEQ ID NO:8. In some embodiments, the variant NRF2 gene comprises: (a) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, or SEQ ID NO:52 substituting positions 728-706 of the reverse complement of SEQ ID NO:7; (b) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, or SEQ ID NO:52 substituting positions 728-706 of the reverse complement of SEQ ID NO:7; (c) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, or SEQ ID NO:52 substituting positions 728-706 of the reverse complement of SEQ ID NO:7; or (d) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, or SEQ ID NO:52 substituting positions 728-706 of the reverse complement of SEQ ID NO:7(a) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (b) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (c) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (d) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (e) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (f) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (g) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; or (h) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7.

An additional aspect is for a cancer cell comprising a mutated variant NRF2 gene produced by the aforementioned method.

Another aspect is for a guide RNA (gRNA) comprising a DNA-binding domain and a Clustered Regularly Interspaced Short Palindromic Repeat (CRISPR)-associated endonuclease protein-binding domain, wherein the DNA-binding domain is complementary to a target sequence in a variant NRF2 gene. In some embodiments, the variant NRF2 gene comprises: (a) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (b) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (c) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (d) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (e) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (f) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (g) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; or (h) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7. In some embodiments, the gRNA is complementary to a target sequence in exon 2 of the variant NRF2 gene. In some embodiments, the DNA-binding domain comprises the nucleic acid sequence of SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:53, SEQ ID NO:55, or a biologically active fragment thereof. In some embodiments, the gRNA comprises a trans-activated small RNA (tracrRNA) and a CRISPR RNA (crRNA). In some embodiments, the gRNA is a single guide RNA.

A further aspect is for a pharmaceutical composition comprising the aforementioned gRNA. In some embodiments, the pharmaceutical composition further comprises a Clustered Regularly Interspaced Short Palindromic Repeat (CRISPR)-associated endonuclease; in some embodiments, the CRISPR-associated endonuclease is a class 2 CRISPR-associated endonuclease; and in some embodiments, the class 2 CRISPR-associated endonuclease is Cas9 or Cas12a.

An additional aspect is for a ribonucleoprotein (RNP) complex comprising the aforementioned gRNA and a Clustered Regularly Interspaced Short Palindromic Repeat (CRISPR)-associated endonuclease. In some embodiments, the CRISPR-associated endonuclease is a class 2 CRISPR-associated endonuclease; and in some embodiments, the class 2 CRISPR-associated endonuclease is Cas9 or Cas12a.

Another aspect is for a pharmaceutical composition comprising the aforementioned RNP complex.

A further aspect is for a DNA sequence encoding the aforementioned gRNA, or a biologically active fragment thereof. In some embodiments, the biologically active fragment is a tracrRNA or a crRNA. In some embodiments, the DNA sequence comprises the nucleic acid sequence of SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:54, or SEQ ID NO:56; and in some embodiments, the biologically active fragment is crRNA comprising the nucleic acid sequence of SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:54, or SEQ ID NO:56.

An additional aspect is for a vector comprising the aforementioned DNA sequence. In some embodiments, the vector is an adeno-associated virus (AAV) vector. In some embodiments, the vector further comprises a nucleic acid sequence that encodes a Clustered Regularly Interspaced Short Palindromic Repeat (CRISPR)-associated endonuclease protein; in some embodiments, the CRISPR-associated endonuclease is a class 2 CRISPR-associated endonuclease; and in some embodiments, class 2 CRISPR-associated endonuclease is Cas9 or Cas12a.

Another aspect is for a pharmaceutical composition comprising the aforementioned DNA sequence or the aforementioned vector. In some embodiments, the pharmaceutical composition comprises the aforementioned DNA sequence and further comprises a nucleic acid sequence that encodes a Clustered Regularly Interspaced Short Palindromic Repeat (CRISPR)-associated endonuclease protein; in some embodiments, the CRISPR-associated endonuclease is a class 2 CRISPR-associated endonuclease; and in some embodiments, the class 2 CRISPR-associated endonuclease is Cas9 or Cas12a.

A further aspect is for a method of treating cancer in a subject comprising administering to the subject a therapeutically effective amount of the aforementioned pharmaceutical composition. In some embodiments, expression or activity of wild-type NRF2 in a non-cancerous cell of the subject is unaffected by the administration of the pharmaceutical composition. In some embodiments, the cancer is resistant to one or more chemotherapeutic agents. In some embodiments, the cancer is lung cancer; in some embodiments, the lung cancer is non-small-cell lung cancer (NSCLC); and in some embodiments, the NSCLC is adenocarcinoma, squamous cell carcinoma, or large cell carcinoma. In some embodiments, the method further comprises administering one or more chemotherapeutic agents to the subject; and in some embodiments, the one or more chemotherapeutic agents are selected from the group consisting of cisplatin, vinorelbine, carboplatin, and a combination thereof. In some embodiments, the pharmaceutical composition is administered in an amount sufficient to reduce proliferation of cells of the cancer relative to cancer cells that are not treated with the pharmaceutical composition. In some embodiments, the pharmaceutical composition is administered in an amount sufficient to reduce tumor growth relative to a tumor that is not treated with the pharmaceutical composition. In some embodiments, the pharmaceutical composition is administered in an amount sufficient to reduce proliferation of cells of the cancer relative to cancer cells that are treated with the at least one chemotherapeutic agent but are not treated with the pharmaceutical composition. In some embodiments, the pharmaceutical composition is administered in an amount sufficient to reduce tumor growth relative to a tumor that is treated with the at least one chemotherapeutic agent but is not treated with the pharmaceutical composition. In some embodiments, the subject is a human.

Other objects and advantages will become apparent to those skilled in the art upon reference to the detailed description that hereinafter follows.

BRIEF DESCRIPTION OF THE DRAWINGS

FIG. 15 shows a summary of On-target analysis. The table provided in the figure is a compilation of the total indel efficiencies (listed as cut) from each experiment for each replicate. The "No cut" columns refer to the percentage of the sequence that aligned to the control sample. SEQ ID NOs: 59-63 represent the five sqRNAs.

FIG. 16 shows INDEL deconvolution BY DECODR of A549 Exon (Neh2) KO Clones. Single gRNA was used to target exon 2, encoding Neh2 Domain, 78 bps downstream from the start of the exon. Three clones, 1-17, 2-16, 2-23, were clonally expanded and analyzed for indel efficiency using the DECODR tool. Clone 1-17 contains −2 (SEQ ID NO:106), −2 (SEQ ID NO:107), −13 bp (SEQ ID NO:108)

deletion at the cleavage site in exon 2 of the NRF2 gene. Clone 2-16 contains a −1 bp (SEQ ID NO:109) deletion across all alleles at the cleavage site. Clone 2-23 contains 2 wildtype alleles with another allele containing a −2 bp (SEQ ID NO:110) deletion at the cleavage site.

Figure 16:
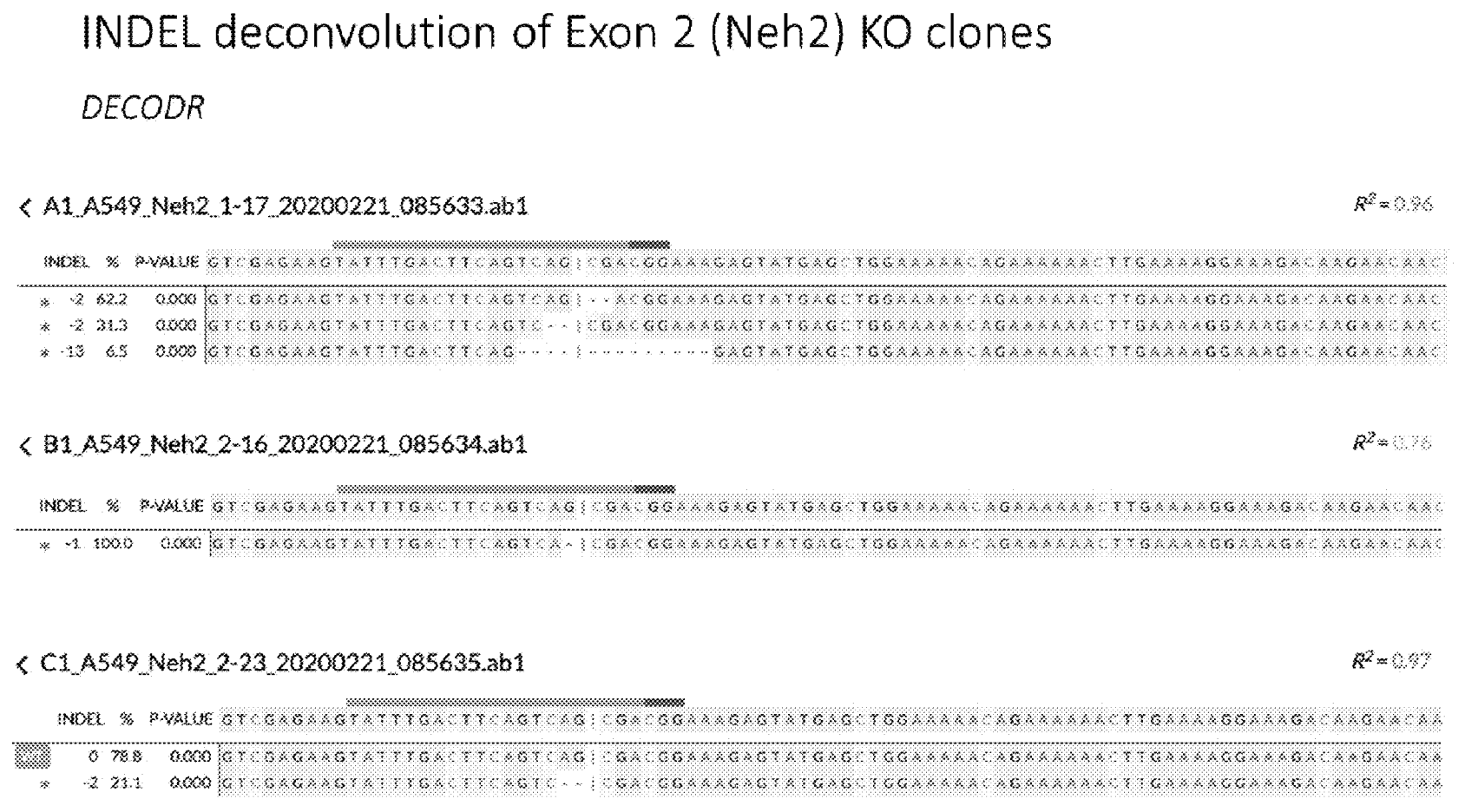

FIG. 16 shows INDEL deconvolution BY DECODR of A549 Exon (Neh2) KO Clones. Single gRNA was used to target exon 2, encoding Neh2 Domain, 78 bps downstream from the start of the exon. Three clones, 1-17, 2-16, 2-23, were clonally expanded and analyzed for indel efficiency using the DECODR tool. Clone 1-17 contains −2, −2, −13 bp deletion at the cleavage site in exon 2 of the NRF2 gene. Clone 2-16 contains a −1 bp deletion across all alleles at the cleavage site. Clone 2-23 contains 2 wildtype alleles with another allele containing a −2 bp deletion at the cleavage site.

Figure 17:
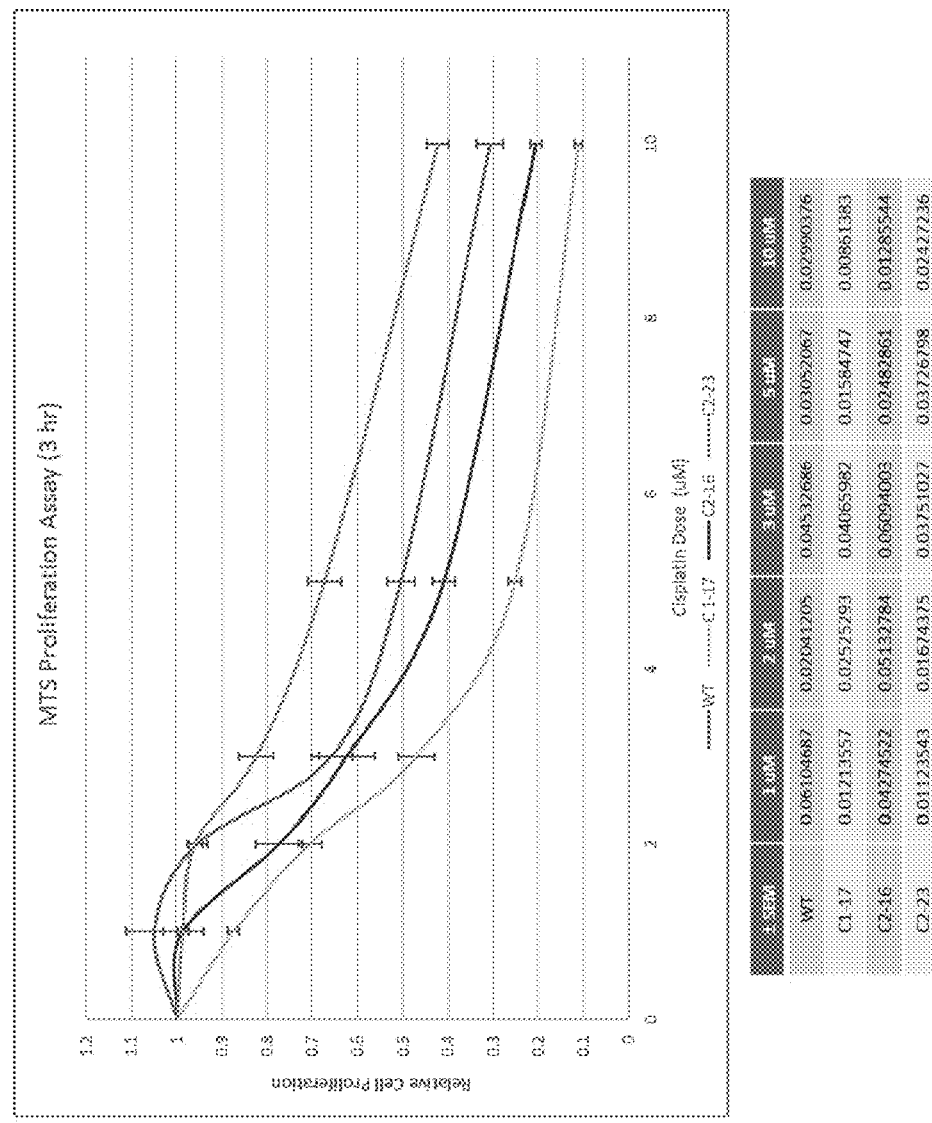

FIG. 17 shows a scatter graph of relative cellular proliferation measured by MTS using A549 Neh2 KO clones treated with cisplatin. The figure contains compiled data from the MTS assay from two separate experiments that were conducted using the same experimental procedures. Each clonal-derived cell line (Clone 1-17, 2-16, 2-23) was plated in quadruplet and treated with increasing concentrations of cisplatin (1, 2, 3, 5, 10 μM). All absorbance values were normalized for each concentration value and clone across both replicates and then graphed. Error bars represent±SEM as listed in the table below the graph.

Figure 19:
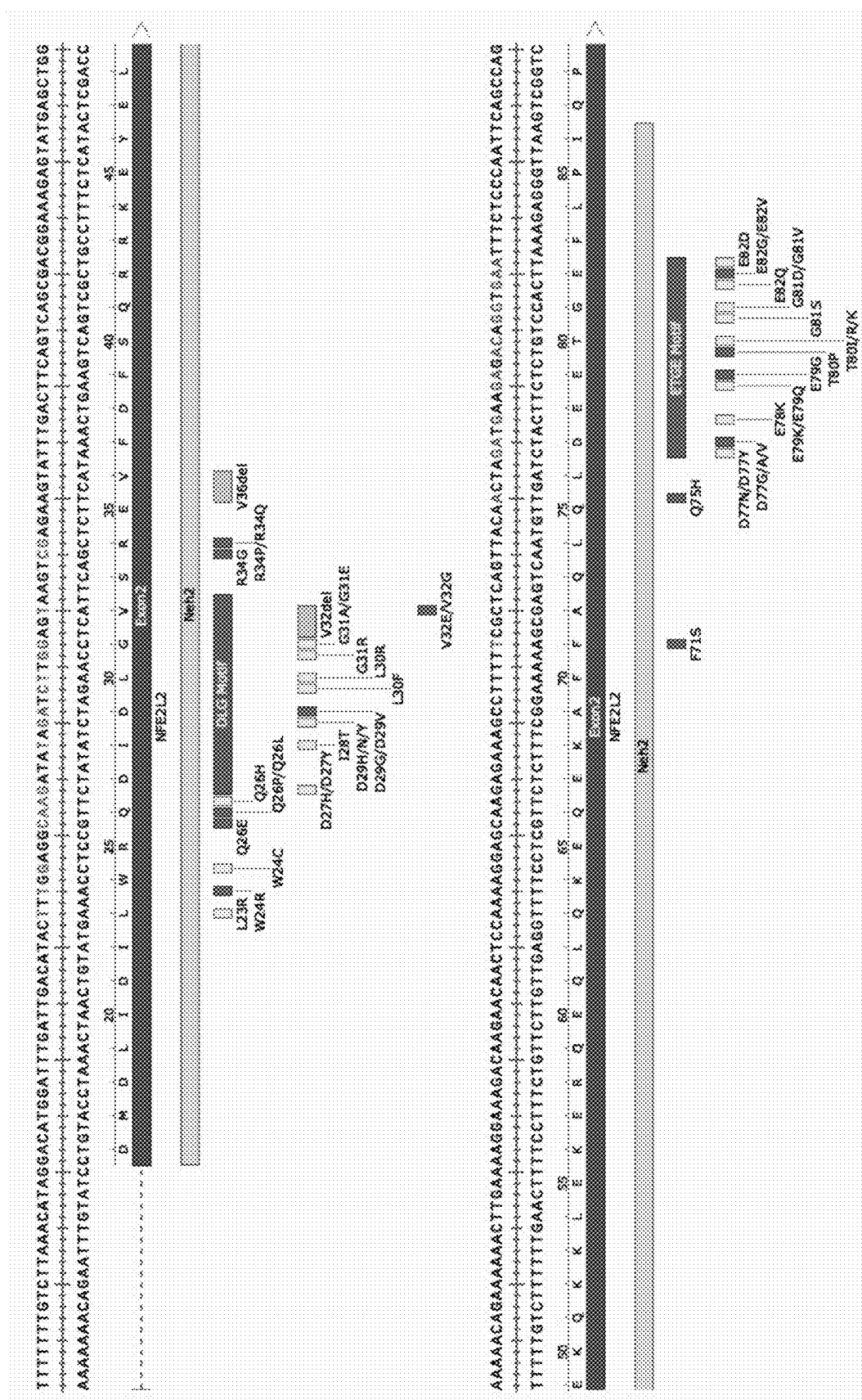

FIG. 19. A catalogue of reported and characterized NRF2 mutations. NRF2 mutations are primarily seen in the Neh2 Domain of the protein, found in exon 2 of the gene (see SEQ ID NO:7). Base changes for each mutation are in red text. Mutations that create new PAM sites for Cas9 recognition are shown in magenta. Other reported mutations are shown in green.

Figure 20:
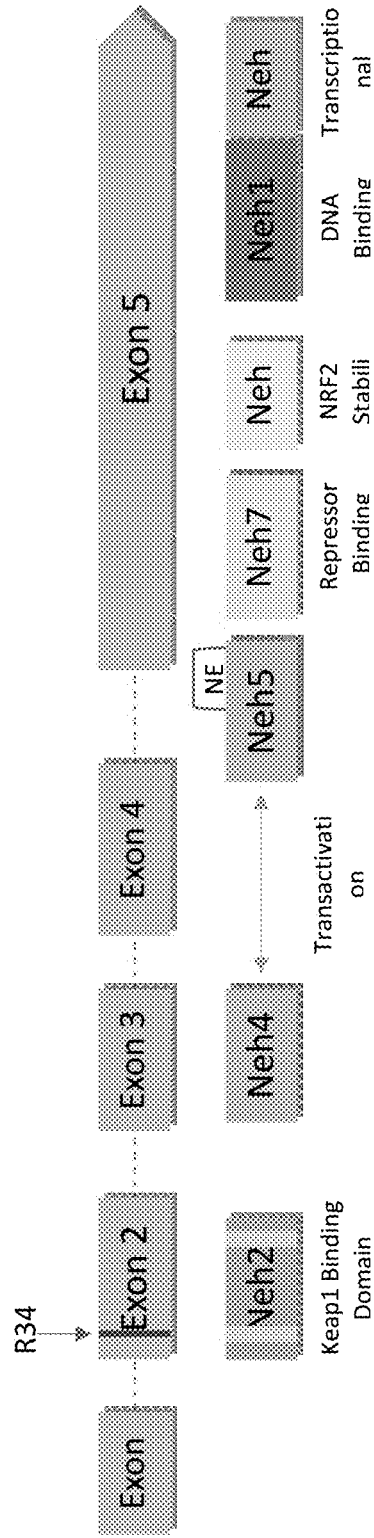

FIG. 20. Structural domains and selective targeting of NRF2. The R34G mutation occurs in exon 2 of the NRF2 gene (SEQ ID NO:7), which encodes the Neh2 Domain of the NRF2 protein (SEQ ID NO:8), shown in upper panel. The lower panel presents a schematic of the creation of a new CRISPR/Cas9 PAM site through the R34G mutation (TCG→TGG) (SEQ ID NO:111 encoding SEQ ID NO:112).

FIG. 19. A catalogue of reported and characterized NRF2 mutations. NRF2 mutations are primarily seen in the Neh2 Domain of the protein, found in exon 2 of the gene. Base changes for each mutation are in red text. Mutations that create new PAM sites for Cas9 recognition are shown in magenta. Other reported mutations are shown in green.

Figure 21:
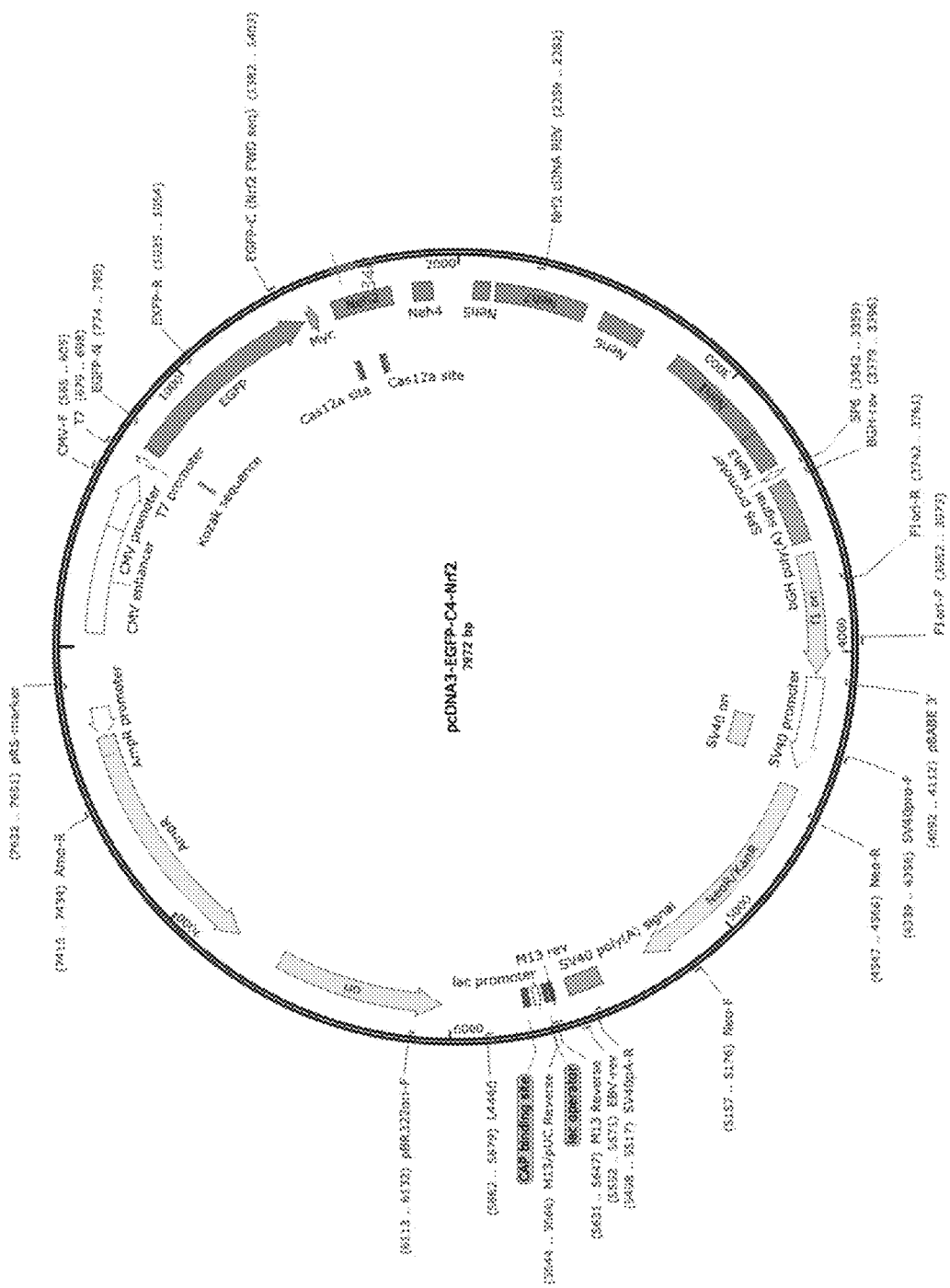

FIG. 21. Recreation of the R34G mutation in a NRF2 expression plasmid. The NRF2 expression plasmid (pcDNA3-EGFP-C4-NRF2, Addgene) was mutated to contain the R34G mutation using CRISPR-directed mutagenesis with two CRISPR/Cas12a cleavage sites and a duplexed oligonucleotide.

Figure 22:
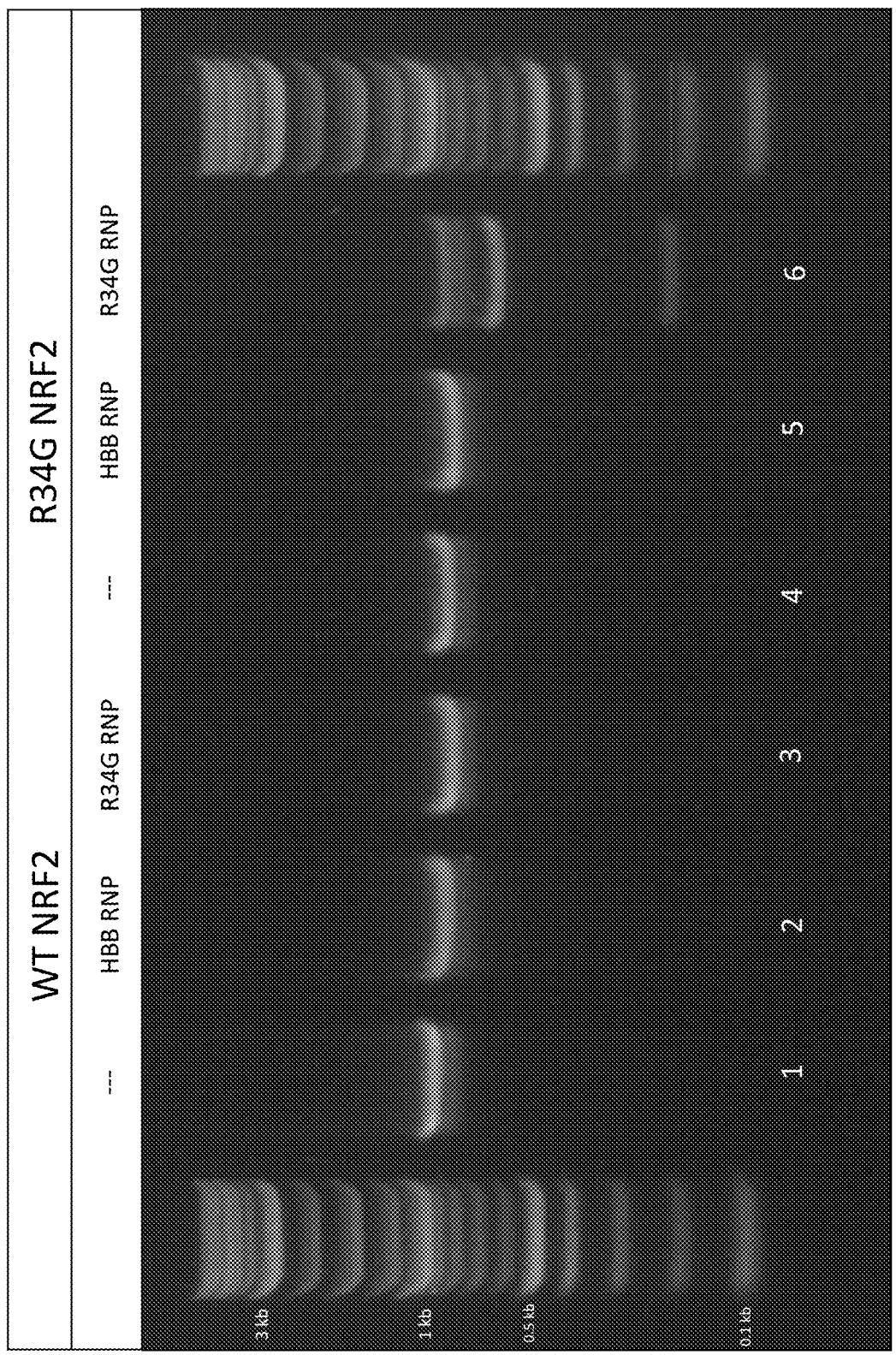

FIG. 22. Proof-of-concept in vitro cleavage reaction using the R34G mutation as a CRISPR/Cas9 cleavage site. Amplicons of wildtype (WT NRF2) and mutated (R34G NRF2) NRF2 expression plasmids were used for cleavage reactions and visualized by gel electrophoresis. Lanes 1 and 5 are amplicons incubated with buffer only (negative control). Lanes 2 and 5 are amplicons incubated with nonspecific RNP (HBB RNP). Lanes 3 and 6 are amplicons incubated with the R34G RNP. The red bars indicate the size of uncut amplicons (901 bp) and cleavage products (222 bp).

Figure 23:
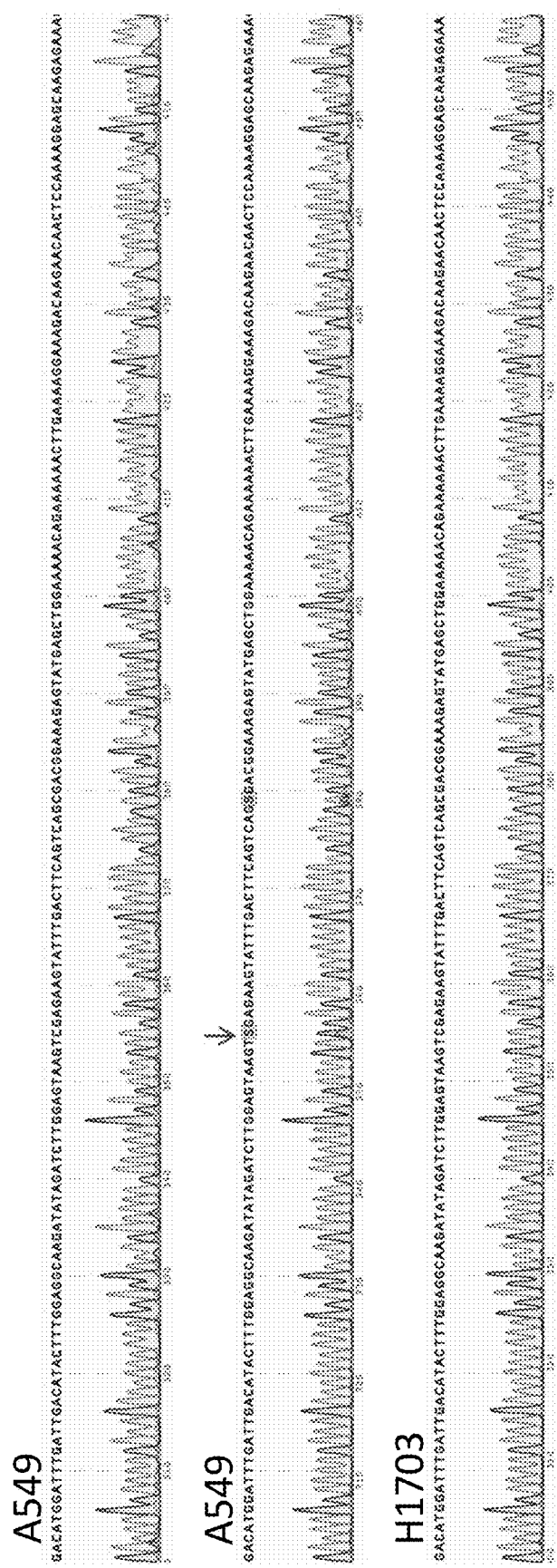

FIG. 23. NRF2 sequence analysis of A549 and H1703 parental cell lines and the A549 R34G-mutated cell line. Genomic DNA from each cell line was sanger sequenced and analyzed for mutations in the Neh2 Domain (exon 2). A549 (SEQ ID NO:113) and H1703 (SEQ ID NO:114) parental cell lines contain a wildtype sequence; whereas the A549 R34G-6 clone (SEQ ID NO:115) contains a heterozygous R34G mutation, indicated by the red arrow.

Figure 24:
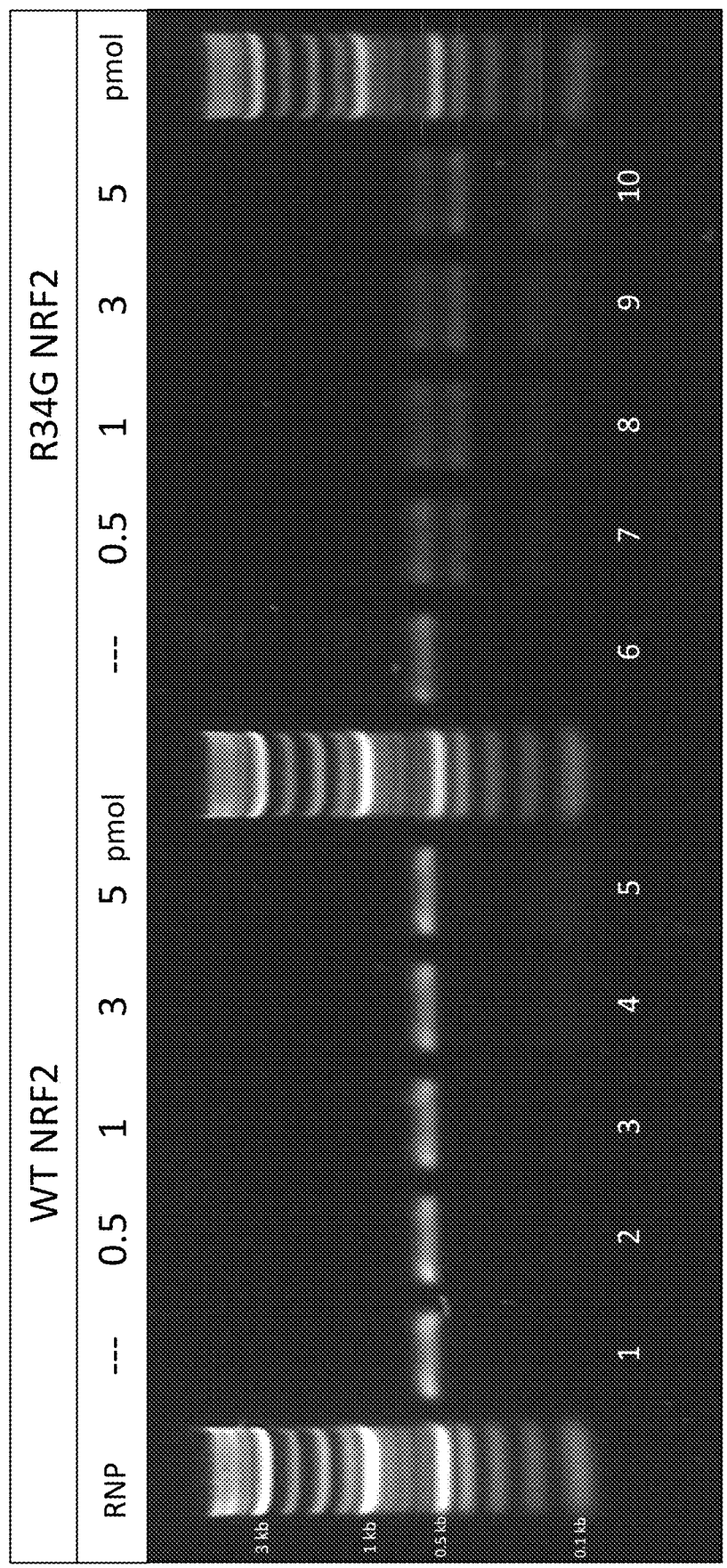

FIG. 24. In vitro cleavage reaction of wildtype and R34G-mutated NRF2 amplicons with varying concentrations of the R34G RNP. NRF2 amplicons, from A549 parental and R34G-6 cells, were incubated with increasing concentrations of the R34G RNP and visualized by gel electrophoresis. Lanes 1 and 6 are the NRF2 amplicons incubated with buffer only. Lanes 2-5 are wildtype NRF2 amplicons incubated with R34G RNP. Lanes 7-10 are R34G-mutated NRF2 amplicons incubated with R34G RNP. The red bars indicate the size of uncut amplicons (530 bp) and cleavage products (145 & 385 bp).

Figure 25:
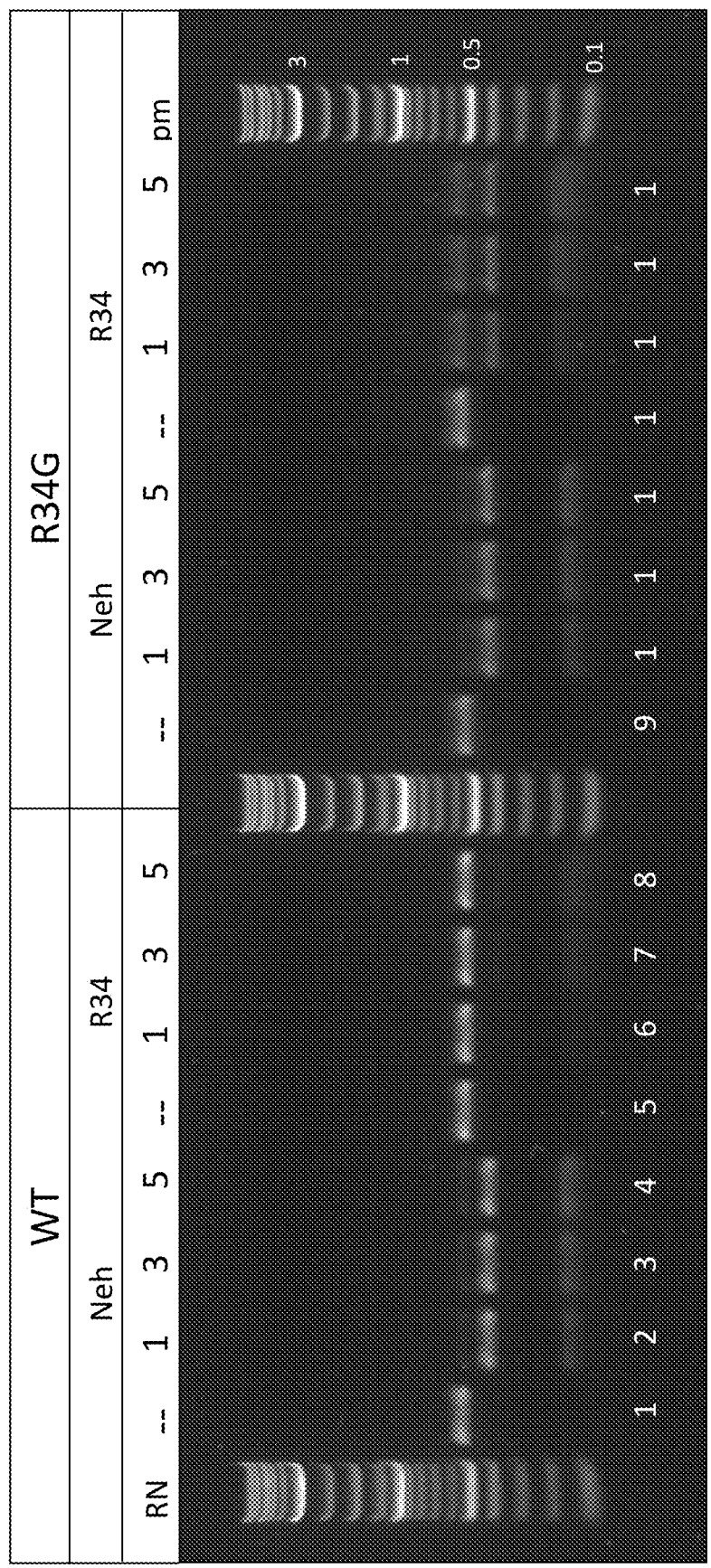

FIG. 25. In vitro cleavage reaction of wildtype and R34G-mutated NRF2 amplicons with varying concentrations of Neh2-targeting RNP and R34G-targeting RNP. NRF2 amplicons, from A549 parental and R34G-6 cells, were incubated with either an RNP targeting a native site within exon 2 of the gene (labeled Neh2) or the R34G mutation, present only in mutated cells. Increasing concentrations of the respective RNP was incubated with NRF2 amplicons and visualized by gel electrophoresis. Lanes 1, 5, 9, and 13 are NRF2 amplicons incubated with buffer only. Lanes 2-4 and 10-12 are the NRF2 amplicons incubated with Neh2-targeting RNP. Uncut amplicons will be visualized at 530 bp and cleavage products will be visualized at 116 and 414 bp. Lanes 6-8 and 14-16 are the NRF2 amplicons incubated with R34G-targeting RNP. Uncut amplicons will be visualized at 530 bp and cleavage products will be visualized at 145 and 385 bp.

Figure 26:
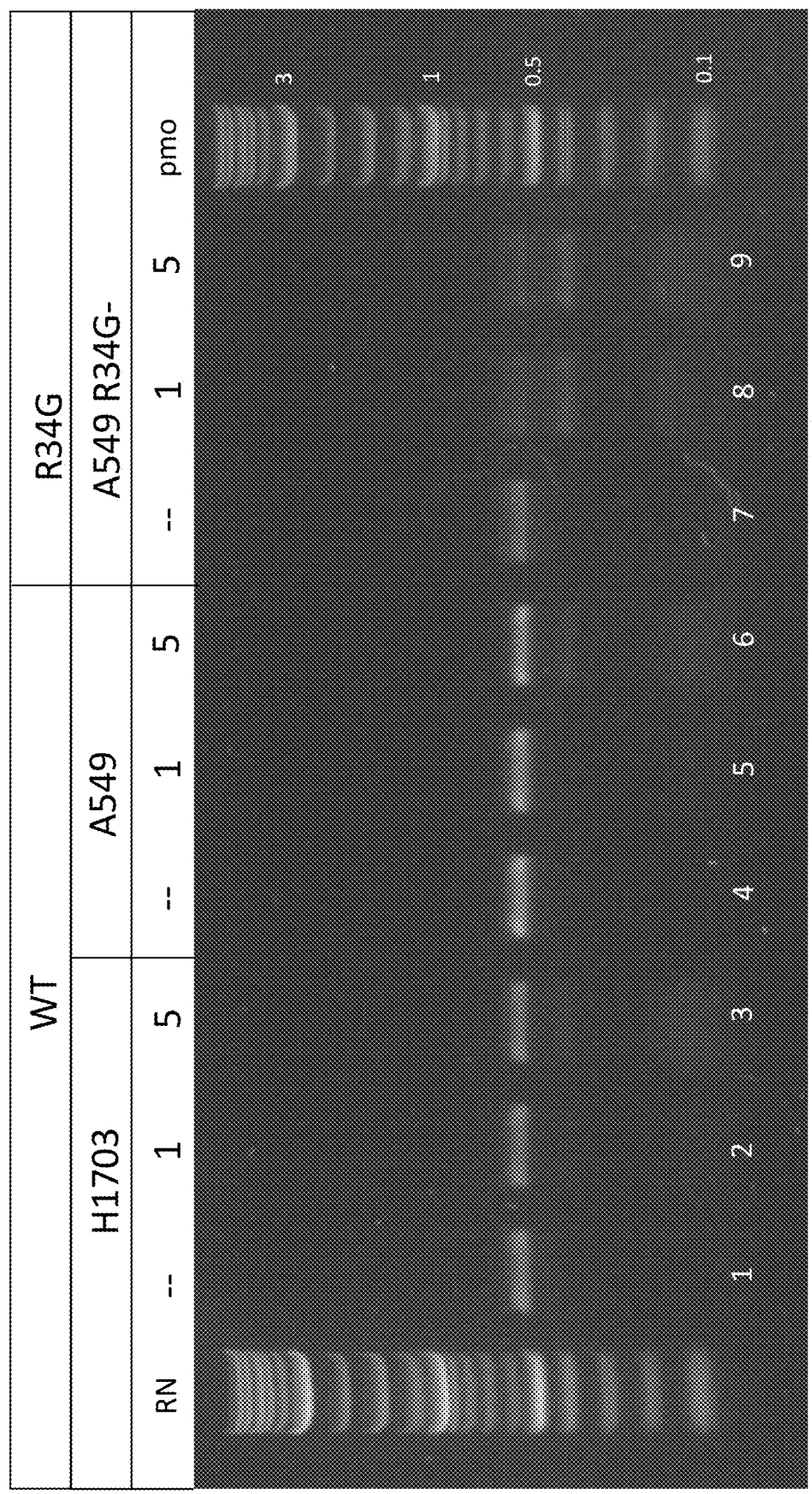

FIG. 26. In vitro cleavage reaction using wildtype and R34G-mutated NRF2 amplicons with varying concentrations of R34G RNP. NRF2 amplicons, from A549 parental, H1703 parental and A549 R34G-6 cells, were incubated with 1 and 5 pmol of R34G RNP and visualized by gel electrophoresis. Lanes 1, 4, and 7 are NRF2 amplicons incubated with buffer only. Lanes 2, 3 and 5, 6 are wildtype NRF2 amplicons incubated with R34G RNP. Lanes 8 and 9 are R34G mutated NRF2 amplicons incubated with R34G RNP. The red bars (right handside of ladder) indicate the size of the uncut amplicons (530 bp) and cleavage products (145 & 385 bp).

Figure 27:
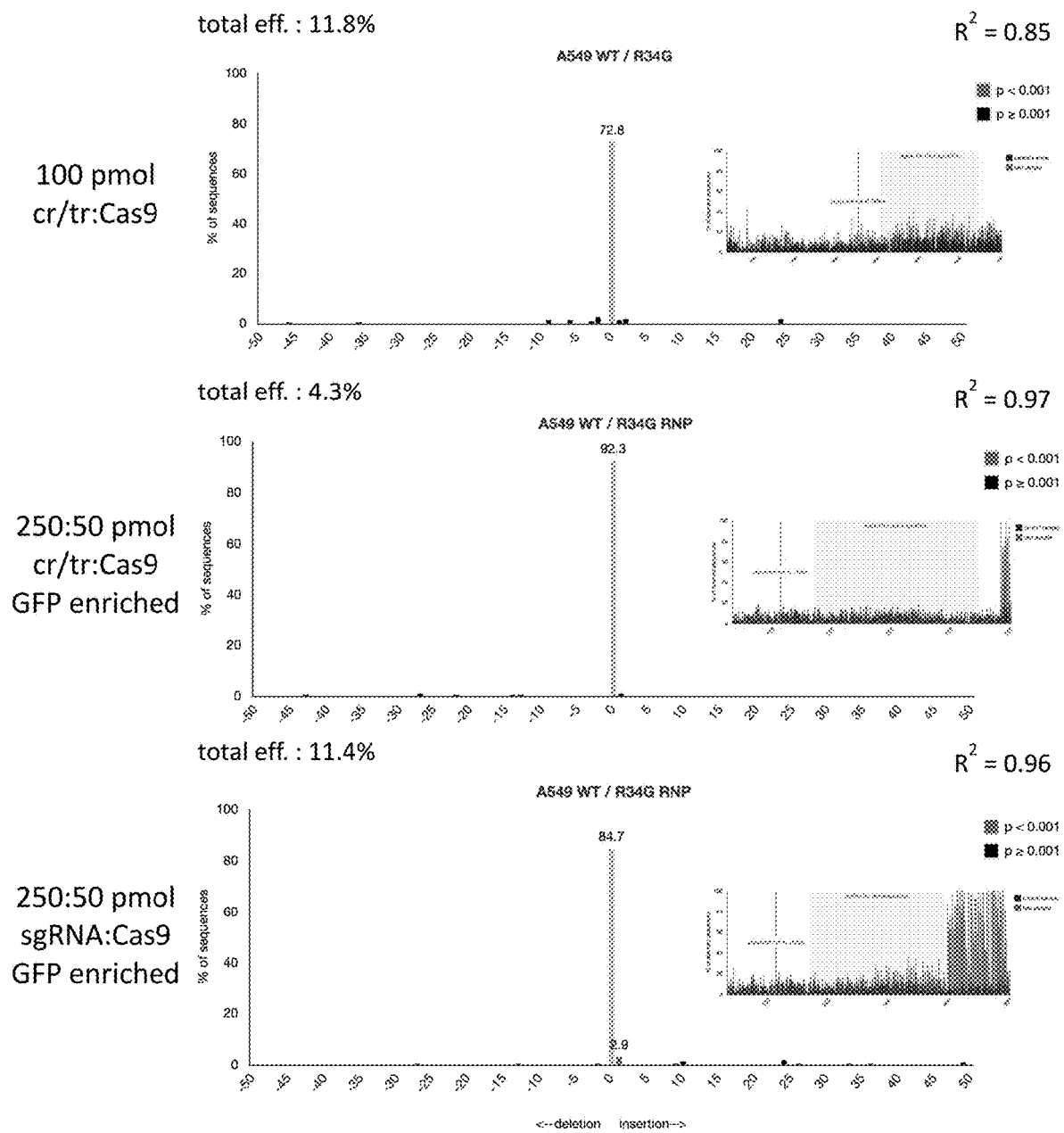

FIG. 27. Genetic analysis of the R34G-targeting RNP activity in the A549 parental cells. Genomic DNA was analyzed by TIDE analysis as a measure of gene editing activity. The top panel shows indel efficiency and sequence alignment of a bulk, unsorted population. The total indel efficiency is 11.4% with one statistically significant deletion noted by the pink bar, whereas the rest of the insertions and deletions are considered statistically insignificant (black bars—p value>0.001). The middle panel shows a total indel efficiency of 3.0% from a bulk, GFP-positive sorted population with only statistically insignificant insertions or deletions. The bottom panel shows a total indel efficiency of 11.3% from a bulk, GFP-positive sorted population with one statistically significant insertion.

Figure 28:
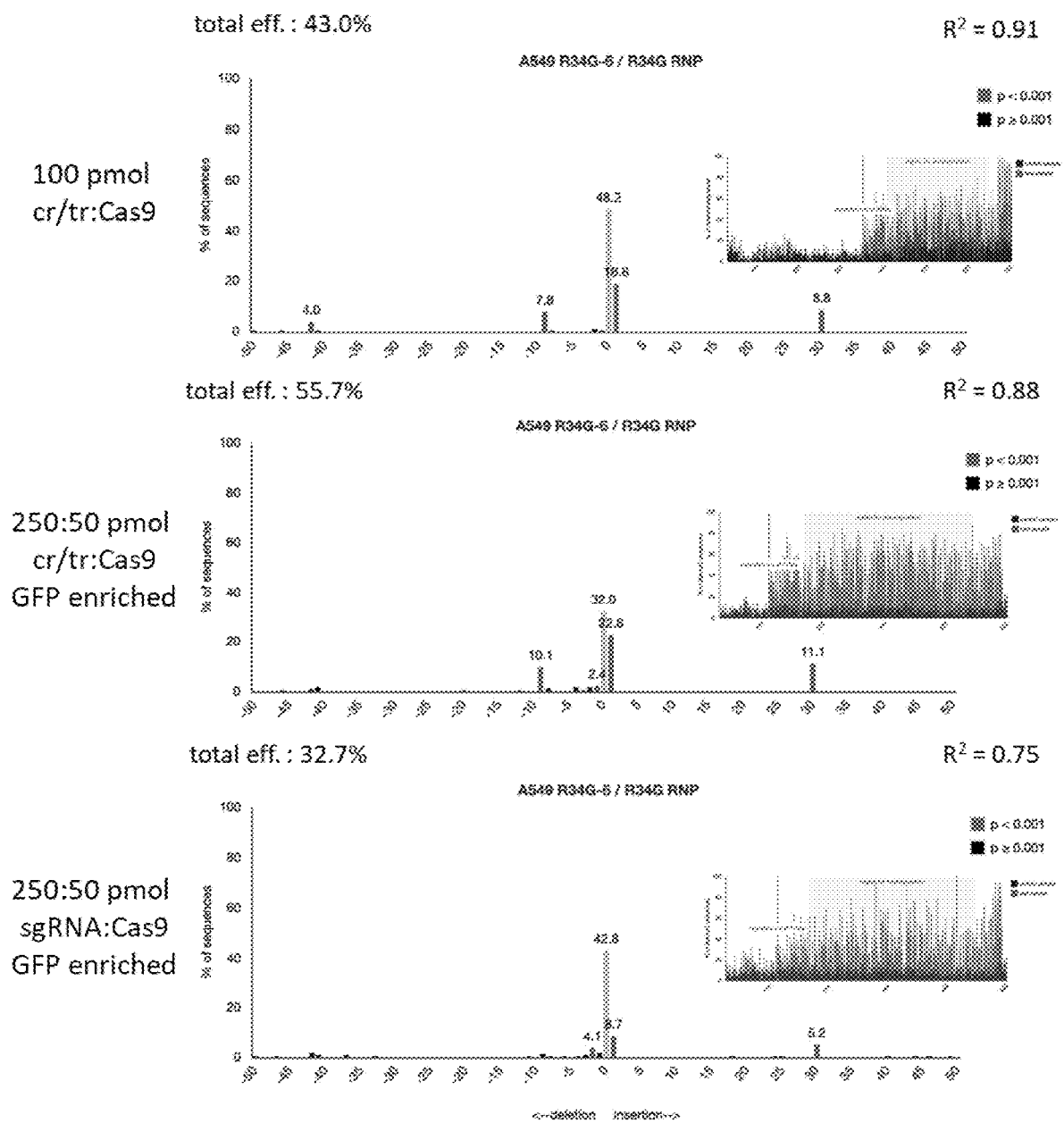

FIG. 28. Genetic analysis of the R34G-targeting RNP activity in the A549 R34G-mutated clonal cell line (A549 R34G-6). Genomic DNA was analyzed by TIDE analysis. The top panel shows indel efficiency and sequence alignment of a bulk, unsorted population with a total indel efficiency of 34.2% and a statistically significant insertion (+1 bp) and deletion (−9 bp) along with several insignificant deletions. The middle panel shows a total indel efficiency of 55.7% from a bulk, GFP-positive sorted population with several statistically significant insertions and deletions and insignificant deletions. The bottom panel shows a total indel efficiency of 32.7% with both significant and insignificant insertions and deletions from a bulk, GFP-positive sorted population.

Figure 29:
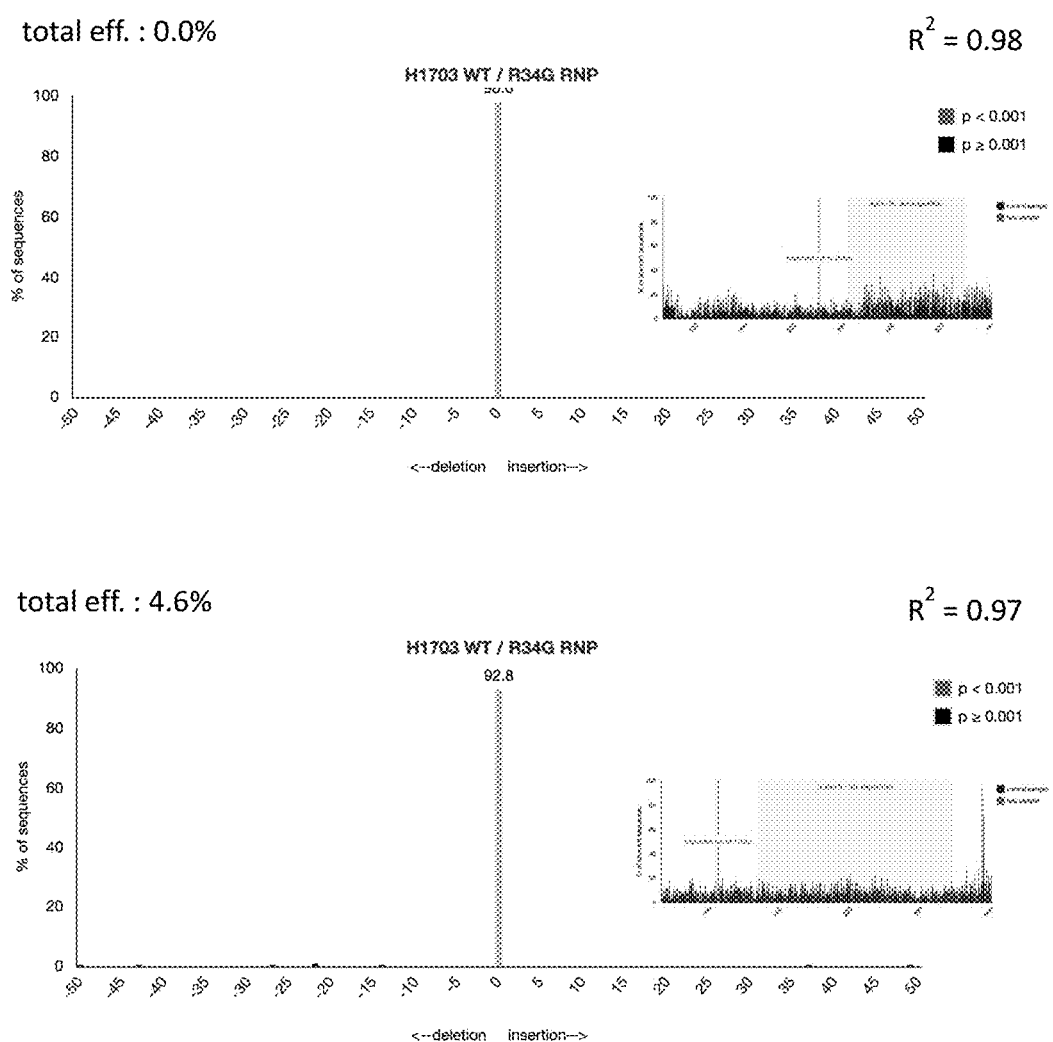

FIG. 29. Genetic analysis after transfection of the R34G-targeting RNP in the H1703 parental cell line. Genomic DNA was by TIDE analysis. The top panel shows total indel efficiency of 0.0% from a bulk, unsorted population. The bottom panel shows total indel efficiency of 4.6% with only insignificant indels from a bulk, GFP-sorted population.

Figure 30:
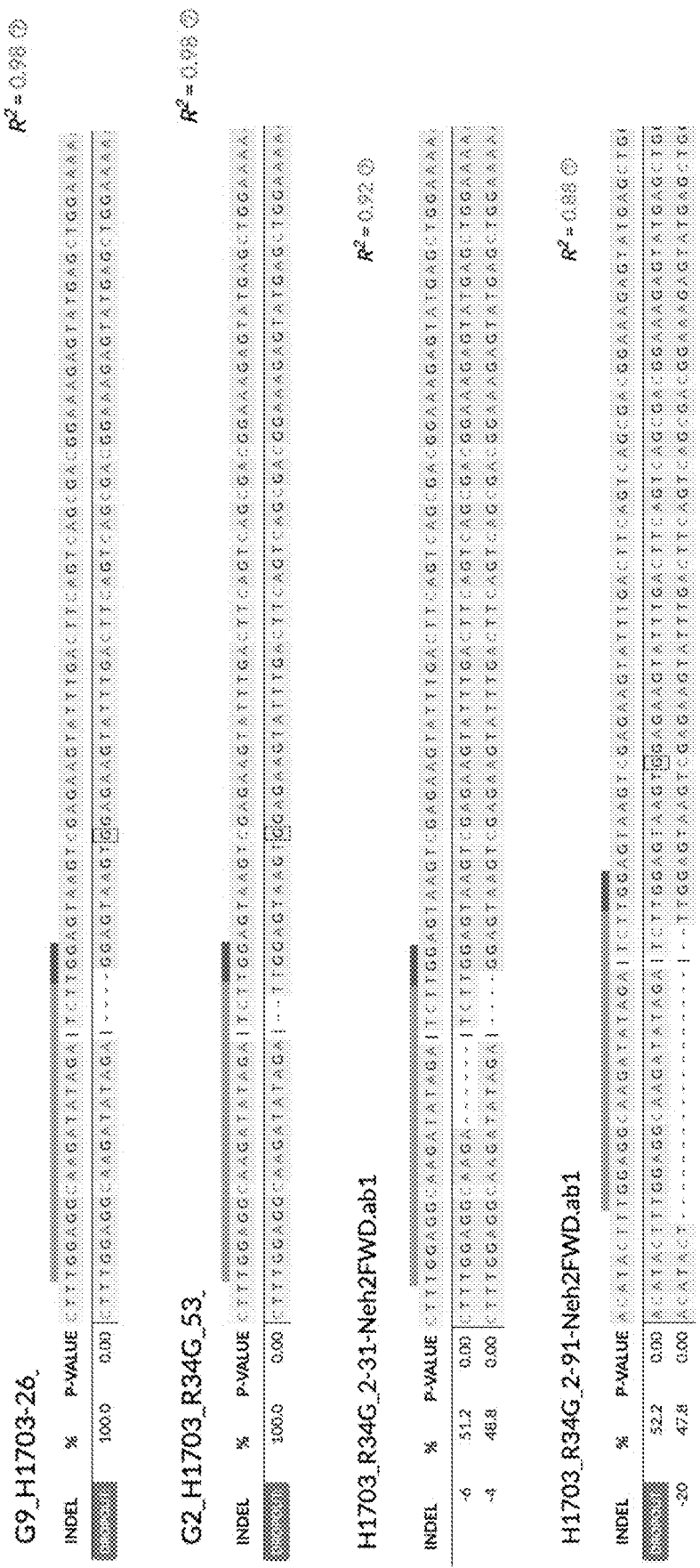

FIG. 30 shows genetic Analysis of H1703 NRF2 KO clonal-derived cell lines. The H1703 cell line was transfected with Exon 2 gRNA 3 and R34G ssDNA template. Cells were expanded and analyzed. Several NRF2 KO clones were selected for further characterization. SEQ ID NO:116 (G9 H1703-26 dropout), SEQ ID NO:117 (G2 H1703 R34G 53 dropout), SEQ ID NO:118 (H1703 R34G 2-31-Neh2FWD.ab1-6 indel), SEQ ID NO:119 (H1703 R34G 2-31-Neh2FWD.ab1-4 indel), SEQ ID NO:120 (H1703 R34G 2-91-Neh2FWD.ab1 dropout), SEQ ID NO:121 (H1703 R34G 2-91-Neh2FWD.ab1-20 indel).

DETAILED DESCRIPTION

This disclosure is based at least in part on the discovery that successful knockout of the NRF2 gene using CRISPR/Cas9 in chemo-resistant A549 lung cancer cells decreased proliferation of the cancer cells and increased effectiveness of the anticancer drugs cisplatin, carboplatin and vinorelbine in both in vitro culture and a xenograft mouse model. The overall strategy was to design and utilize a CRISPR/Cas gene editing tool to disable the NRF2 gene in cancer cells rendering it incapable of producing a functional protein. The CRISPR/Cas9 complex aligns in homologous register with the target gene, which enables it to execute a double-stranded DNA break. This action is followed by an attempt by the cell to reclose scission, most often through a process known as nonhomologous end joining (NHEJ). The reclosure is often imperfect and unfaithful as a number of nucleotides are lost during the process resulting in a genetic frameshift and the subsequent production of nonfunctional transcripts, a gene knockout of NRF2.

The compositions described herein include nucleic acids encoding a CRISPR-associated endonuclease (e.g., Cas9) and a guide RNA that is complementary to an NRF2 gene (e.g. exon 1, 2, 3, 4, or 5 of an NRF2 gene). Compositions comprising the guide RNA and the CRISPR-associated endonuclease are also described, as well as methods of administering the compositions to a subject for the treatment of cancer.

In some embodiments, the guide RNA is complementary to a variant NRF2 gene that is found only in cancer cells and not in wild-type NRF2 genes in normal (i.e., non-cancerous) cells (e.g. exon 1, 2, 3, 4, or 5). In some embodiments, the guide RNA is complementary to a sequence in exon 2 of a variant NRF2 gene that is found only in cancer cells.

Definitions

Applicants specifically incorporate the entire contents of all cited references in this disclosure. Further, when an amount, concentration, or other value or parameter is given as either a range or a list of upper values and lower values, this is to be understood as specifically disclosing all ranges formed from any pair of any upper range limit or value and any lower range limit or value, regardless of whether ranges are separately disclosed. Where a range of numerical values is recited herein, unless otherwise stated, the range is intended to include the endpoints thereof, and all integers and fractions within the range. It is not intended that the scope of the present disclosure be limited to the specific values recited when defining a range.

The indefinite articles "a" and "an", as used herein in the specification and in the claims, unless clearly indicated to the contrary, should be understood to mean "at least one".

The phrase "and/or", as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of", or, when used in the claims, "consisting of", will refer to the inclusion of exactly one element of a number or list of elements. In general, the term "or" as used herein shall only be interpreted as indicating exclusive alternatives (i.e., "one or the other but not both") when preceded by terms of exclusivity, "either", "one of", "only one of", "exactly one of". "Consisting essentially of", when used in the claims, shall have its ordinary meaning as used in the field of patent law.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

A "Clustered Regularly Interspaced Short Palindromic Repeat (CRISPR)-associated endonuclease protein-binding domain" or "Cas binding domain" refers to a nucleic acid element or domain within a nucleic acid sequence or polynucleotide sequence that, in an effective amount, will bind or have an affinity for one or a plurality of CRISPR-associated endonuclease (or functional fragments thereof). In some embodiments, in the presence of the one or a plurality of proteins (or functional fragments thereof) and a target sequence, the one or plurality of proteins and the nucleic acid element forms a biologically active CRISPR complex and/or can be enzymatically active on a target sequence. In some embodiments, the CRISPR-associated endonuclease is a class 1 or class 2 CRISPR-associated endonuclease, and in some embodiments, a Cas9 or Cas12a endonuclease. The Cas9 endonuclease can have a nucleotide sequence identical to the wild type *Streptococcus pyogenes* sequence. In some embodiments, the CRISPR-associated endonuclease can be a sequence from other species, for example other *Streptococcus* species, such as *thermophilus; Pseudomona aeruginosa, Escherichia coli*, or other sequenced bacteria genomes and archaea, or other prokaryotic microorganisms. Such species include: *Acidovorax avenae, Actinobacillus pleuropneumoniae, Actinobacillus succinogenes, Actinobacillus suis, Actinomyces* sp., *Cycliphilusdenitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, Gammaproteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria meningitidis, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus aureus, Staphylococcus lugdunensis, Streptococcus* sp., *Subdoligranulum* sp., *Tistrella mobilis, Treponema* sp., and *Verminephrobacter eiseniae* (or functional fragments or variants of any of the aforementioned sequences that have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to any of the aforementioned Cas9 endonucleases). In some embodiments, the CRISPR-associated endonuclease can be a Cas12a nuclease. The Cas12a nuclease can have a nucleotide sequence identical to a wild type Prevotella or Francisella sequence (or functional fragments or variants of any of the aforementioned sequences that have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to any of the aforementioned Cas12 endonucleases).

In some embodiments, the terms "(CRISPR)-associated endonuclease protein-binding domain" or "Cas binding domain" refer to a nucleic acid element or domain (e.g. and RNA element or domain) within a nucleic acid sequence that, in an effective amount, will bind to or have an affinity for one or a plurality of CRISPR-associated endonucleases (or functional fragments or variants thereof that are at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homologous to a CRISPR-associated endonucleas). In some embodiments, the Cas binding domain consists of at least or no more than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, or 250 nucleotides and comprises at least one sequence that is capable of forming a hairpin or duplex that partially associates or binds to a biologically active CRISPR-associated endonuclease at a concentration and within a microenvironment suitable for CRISPR system formation.

The "Clustered Regularly Interspaced Short Palindromic Repeats (CRISPR)-CRISPR associated (Cas) (CRISPR-Cas) system guide RNA" or "CRISPR-Cas system guide RNA" may comprise a transcription terminator domain. The term "transcription terminator domain" refers to a nucleic acid element or domain within a nucleic acid sequence (or polynucleotide sequence) that, in an effective amount, prevents bacterial transcription when the CRISPR complex is in a bacterial species and/or creates a secondary structure that stabilizes the association of the nucleic acid sequence to one or a plurality of Cas proteins (or functional fragments thereof) such that, in the presence of the one or a plurality of proteins (or functional fragments thereof), the one or plurality of Cas proteins and the nucleic acid element forms a biologically active CRISPR complex and/or can be enzymatically active on a target sequence in the presence of such a target sequence and a DNA-binding domain. In some embodiments, the transcription terminator domain consists of at least or no more than about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, or 250 nucleotides and comprises at least one sequence that is capable of forming a hairpin or duplex that partially drives association of the nucleic acid sequence (sgRNA, crRNA with tracrRNA, or other nucleic acid sequence) to a biologically active CRISPR complex at a concentration and microenvironment suitable for CRISPR complex formation.

The term "DNA-binding domain" refers to a nucleic acid element or domain within a nucleic acid sequence (e.g. a guide RNA) that is complementary to a target sequence (e.g. an NRF2 gene). In some embodiments, the DNA-binding domain will bind or have an affinity for an NRF2 gene such that, in the presence of a biologically active CRISPR complex, one or plurality of Cas proteins can be enzymatically active on the target sequence. In some embodiments, the DNA binding domain comprises at least one sequence that is capable of forming Watson Crick basepairs with a target sequence as part of a biologically active CRISPR system at a concentration and microenvironment suitable for CRISPR system formation.

"CRISPR system" refers collectively to transcripts or synthetically produced transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a nucleic acid sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, the target sequence is a DNA polynucleotide and is referred to a DNA target sequence. In some embodiments, a target sequence comprises at least three nucleic acid sequences that are recognized by a Cas-protein when the Cas protein is associated with a CRISPR complex or system which comprises at least one sgRNA or one tracrRNA/crRNA duplex at a concentration and within an microenvironment suitable for association of such a system. In some embodiments, the target DNA comprises at least one or more proto-spacer adjacent motifs which sequences are known in the art and are dependent upon the Cas protein system being used in conjunction with the sgRNA or crRNA/tracrRNAs employed by this work. In some embodiments, the target DNA comprises NNG, where G is an guanine and N is any naturally occurring nucleic acid. In some embodiments the target DNA comprises any one or combination of NNG, NNA, GAA, NNAGAAW and NGGNG, where G is an guanine, A is adenine, and N is any naturally occurring nucleic acid In some embodiments, a target sequence is located in the nucleus or cytoplasm of a cell.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional (bind the Cas protein or functional fragment thereof). In some embodiments, the tracr sequence has at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of sequence complementarity along the length of the tracr mate sequence when optimally aligned. In some embodiments, one or more vectors driving expression of one or more elements of a CRISPR system are introduced into a host cell such that the presence and/or expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. With at least some of the modification contemplated by this disclosure, in some embodiments, the guide sequence or RNA or DNA sequences that form a CRISPR complex are at least partially synthetic. The CRISPR system elements that are combined in a single vector may be arranged in any suitable orientation, such as one element located 5' with respect to ("upstream" of) or 3' with respect to ("downstream" of) a second element. In some embodiments, the disclosure relates to a composition comprising a chemically synthesized guide sequence. In some embodiments, the chemically synthesized guide sequence is used in conjunction with a vector comprising a coding sequence that encodes a CRISPR enzyme, such as a class 2 Cas9 or Cas12a protein. In some embodiments, the chemically synthesized guide sequence is used in conjunction with one or more vectors, wherein each vector comprises a coding sequence that encodes a CRISPR enzyme, such as a class 2 Cas9 or Cas12a protein. The coding sequence of one element may be located on the same or opposite strand of the coding sequence of a second element, and oriented in the same or opposite direction. In some embodiments, a single promoter drives expression of a transcript encoding a CRISPR enzyme and one or more additional (second, third, fourth, etc.) guide sequences, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, one or more additional guide sequence, tracr mate sequence, and tracr sequence are each a component of different nucleic acid sequences. For instance, in the case of a tracr and tracr mate sequences and in some embodiments, the disclosure relates to a composition comprising at least a first and second nucleic acid sequence, wherein the first nucleic acid sequence comprises a tracr sequence and the second nucleic acid sequence comprises a tracr mate sequence, wherein the first nucleic acid sequence is at least partially complementary to the second nucleic acid sequence such that the first and second nucleic acid for a duplex and wherein the first nucleic acid and the second nucleic acid either individually or collectively comprise a DNA-targeting domain, a Cas protein binding domain, and a transcription terminator domain. In some embodiments, the CRISPR enzyme, one or more additional guide sequence, tracr mate sequence, and tracr sequence are operably linked to and expressed from the same promoter. In some embodiments, the disclosure relates to compositions comprising any one or combination of the disclosed domains on one guide sequence or two separate tracrRNA/crRNA sequences with or without any of the disclosed modifications. Any methods disclosed herein also relate to the use of tracrRNA/crRNA sequence interchangeably with the use of a guide sequence, such that a composition may comprise a single synthetic guide sequence and/or a synthetic tracrRNA/crRNA with any one or combination of modified domains disclosed herein.

In some embodiments, a guide RNA can be a short, synthetic, chimeric tracrRNA/crRNA (a "single-guide RNA" or "sgRNA"). A guide RNA may also comprise two short, synthetic tracrRNA/crRNAs (a "dual-guide RNA" or "dgRNA").

The terms "cancer" or "tumor" are well known in the art and refer to the presence, e.g., in a subject, of cells possessing characteristics typical of cancer-causing cells, such as uncontrolled proliferation, immortality, metastatic potential, rapid growth and proliferation rate, decreased cell death/apoptosis, and certain characteristic morphological features.

As used herein, "cancer" refers to all types of cancer or neoplasm or malignant tumors found in humans, including, but not limited to: leukemias, lymphomas, melanomas, carcinomas and sarcomas. As used herein, the terms or language "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also cancer stem cells, as well as cancer progenitor cells or any cell derived from a cancer cell ancestor. This includes metastasized cancer cells, and in vitro cultures and cell lines derived from cancer cells. In certain embodiments, the cancer is a blood tumor (i.e., a non-solid tumor). In some embodiments, the cancer is lymphoid neoplasm diffuse large B-cell lymphoma, cholangiocarcinoma, uterine carcinosarcoma, kidney chromophobe, uveal melanoma, mesothelioma, adrenocortical carcinoma, thymoma, acute myeloid leukemia, testicular germ cell tumor, rectum adenocarcinoma, pancreatic adenocarcinoma, phenochromocytoma and paraganglioma, esophageal carcinoma, sarcoma, kidney renal papillary cell carcinoma, cervical squamous cell carcinoma and endocervical adenocarcinoma, kidney renal clear cell carcinoma, liver hepatocellular carcinoma, glioblastoma multiforme, bladder urothelial carcinoma, colon adenocarcinoma, stomach adenocarcinoma, ovarian serous cystadenocarcinoma, skin cutaneous melanoma, prostate adenocarcinoma, thyroid carcinoma, lung squamous cell carcinoma, head and neck squamous cell carcinoma, brain lower grade glioma, uterine corpus endometrial carcinoma, lung adenocarcinoma, or breast invasive carcinoma (see, e.g., Kerins et al., Sci. Rep. 8:12846 (2018)).

In certain embodiments, the cancer is a solid tumor. A "solid tumor" is a tumor that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient. The tumor does not need to have measurable dimensions.

Specific criteria for the staging of cancer are dependent on the specific cancer type based on tumor size, histological characteristics, tumor markers, and other criteria known by those of skill in the art. Generally, cancer stages can be described as follows:

Stage 0—Carcinoma in situ

Stage I, Stage II, and Stage III—Higher numbers indicate more extensive disease: Larger tumor size and/or spread of the cancer beyond the organ in which it first developed to nearby lymph nodes and/or tissues or organs adjacent to the location of the primary tumor Stage IV—The cancer has spread to distant tissues or organs As used herein, a "variant", "mutant", or "mutated" polynucleotide contains at least one polynucleotide sequence alteration as compared to the polynucleotide sequence of the corresponding wild-type or parent polynucleotide. Mutations may be natural, deliberate, or accidental. Mutations include substitutions, deletions, and insertions.

As used herein, the terms "treat," "treating" or "treatment" refer to an action to obtain a beneficial or desired clinical result including, but not limited to, alleviation or amelioration of one or more signs or symptoms of a disease or condition (e.g., regression, partial or complete), diminishing the extent of disease, stability (i.e., not worsening, achieving stable disease) of the state of disease, amelioration or palliation of the disease state, diminishing rate of or time to progression, and remission (whether partial or total). "Treatment" of a cancer can also mean prolonging survival as compared to expected survival in the absence of treatment. Treatment need not be curative. In certain embodiments, treatment includes one or more of a decrease in pain or an increase in the quality of life (QOL) as judged by a qualified individual, e.g., a treating physician, e.g., using accepted assessment tools of pain and QOL. In certain embodiments, a decrease in pain or an increase in the QOL as judged by a qualified individual, e.g., a treating physician, e.g., using accepted assessment tools of pain and QOL is not considered to be a "treatment" of the cancer.

"Chemotherapeutic agent" refers to a drug used for the treatment of cancer. Chemotherapeutic agents include, but are not limited to, small molecules, hormones and hormone analogs, and biologics (e.g., antibodies, peptide drugs, nucleic acid drugs). In certain embodiments, chemotherapy does not include hormones and hormone analogs.

A "cancer that is resistant to one or more chemotherapeutic agents" is a cancer that does not respond, or ceases to respond to treatment with a chemotherapeutic regimen, i.e., does not achieve at least stable disease (i.e., stable disease, partial response, or complete response) in the target lesion either during or after completion of the chemotherapeutic regimen. Resistance to one or more chemotherapeutic agents results in, e.g., tumor growth, increased tumor burden, and/or tumor metastasis.

A "therapeutically effective amount" is that amount sufficient, at dosages and for periods of time necessary, to achieve a desired therapeutic result, such as for treatment of a disease (e.g. cancer), condition, or disorder, and/or pharmacokinetic or pharmacodynamic effect of the treatment in a subject. A therapeutically effective amount can be administered in one or more administrations. The therapeutically effective amount may vary according to factors such as the disease state, age, sex, and weight of the subject.

NRF2

Nuclear Factor Erythroid 2-Related Factor (NRF2) is considered the master regulator of 100-200 target genes involved in cellular responses to oxidative/electrophilic stress. Targets include glutathione (GSH) mediators, antioxidants and genes controlling efflux pumps. Hayden, et al., Urol. Oncol. Semin. Orig. Investig. 32, 806-814 (2014). NRF2 is also known to regulate expression of genes involved in protein degradation and detoxification and is negatively regulated by Kelch-like ECH-associated protein 1 (KEAP1), a substrate adapter for the Cul3-dependent E3 ubiquitin ligase complex. Under normal conditions, Keap1 constantly targets NRF2 for ubiquitin-dependent degradation maintaining low expression of NRF2 on downstream target genes. However, chemotherapy has been shown to activate transcriptional activity of the NRF2 target genes often triggering a cytoprotective response; enhanced expression of NRF2 occurs in response to environmental stress or detrimental growth conditions. Other mechanisms that lead to NRF2 upregulation include mutations in KEAP1 or epigenetic changes of the promoter region. The upregulation of NRF2 expression leads to an enhanced resistance of cancer cells to chemotherapeutic drugs, which by their very action induce an unfavorable environment for cell proliferation. Indeed, Hayden et al. (ibid) have clearly demonstrated that increased NRF2 expression leads to the resistance of cancer cells to chemotherapeutic drugs including cisplatin. Singh et al. (2010, Antioxidants & Redox Signaling 13) also showed that constitutive expression of NRF2 leads to radioresistance, and inhibition of NRF2 causes increased endogenous reactive oxygen species (ROS) levels as well as decreased survival. Recently, Torrente et al. (Oncogene (2017). doi: 10.1038/onc.2017.221) identified crosstalk between NRF2 and the homeodomain interacting protein kinase two, HIPK2, demonstrating that HIPK2 exhibits a cytoprotective effect through NRF2.

By using CRISPR/Cas9, it is possible to target and knock out the mutated NRF2 protein causing chemoresistance, while not disrupting the function of wildtype NRF2 protein. Thus, some embodiments are directed to reducing or, in some embodiments, eliminating expression of variant NRF2s found only in cancer cells and not in non-cancerous cells. These variants are commonly found within the Neh2 Domain of NRF2, which is known as the KEAP1 binding domain. In some embodiments, the NRF2 mutations can be those found in Table 1 below.

TABLE 1

| SEQ ID NO: | Sequence, with substitution identified in brackets | Base position in SEQ ID NO: 7 | Notes/ Amino Acid substitution (relative to position in (SEQ ID NO: 8) |
|---|---|---|---|
| 41 | TTTGATTGACATACT TTGGAGGC(C > G) | 205-227 | Q26E |
| 42 | CTTACTCCAAGATCT ATATCTT(T > G)G | 249-227 | Reverse complement; Q26P |
| 43 | ATACTTTGGAGGCAA GATATAGA(A > G) | 215-237 | D29G |
| 44 | AGGCAAGATATAGAT CTTGGAGT(T > G) | 224-246 | V32G |
| 45 | GATATAGATCTTGGA GTAAGTC(C > G)G | 230-252 | R34G |
| 46 | TGACTGAAGTCAAAT ACTTCTC(C > G)G | 273-251 | Reverse complement; R34P |
| 47 | TTCATCTAGTTGTAA CTGAGCGA(A > G) | 385-363 | Reverse complement; F71S |
| 48 | ATTCACCTGTCTCTT CATCTAGT(T > G) | 398-376 | Reverse complement; Q75H |
| 49 | CTCAGTTACAACTAG ATGAAGA(A > G)G | 366-388 | E79G |
| 50 | TGAATTGGGAGAAAT TCACCTGT(T > G) | 411-389 | Reverse complement; T80P |
| 51 | CAACTAGATGAAGAG ACAGGTGA(A > G) | 374-396 | E82W |

TABLE 1-continued

| SEQ ID NO: | Sequence, with substitution identified in brackets | Base position in SEQ ID NO: 7 | Notes/ Amino Acid substitution (relative to position in (SEQ ID NO: 8) |
|---|---|---|---|
| 52 | ATAATAGCTCCTCCC AAACTTGC(C > G) | 728-706 | Reverse complement; E185D |
| 57 | TTTTTCGCTCAGTTA CAACTAGA(A > G) | 360-381 | D77G |
| 58 | CAACTAGATGAAGAG ACAGGTGA(A > G) | 374-396 | E82G |

PAM sequence underlined.

In some embodiments, a variant NRF2 polypeptide encoded by the variant NRF2 gene in a cancer cell can comprise one or more amino acid substitutions of: (a) Q26E, D29G, V32G, R34G, F71S, Q75H, D77G, E79G, T80P, E82W, or E185D relative to SEQ ID NO:8; (b) Q26E, D29G, V32G, R34P, F71S, Q75H, D77G, E79G, T80P, E82W, or E185D relative to SEQ ID NO:8; (c) Q26P, D29G, V32G, R34G, F71S, Q75H, D77G, E79G, T80P, E82W, or E185D relative to SEQ ID NO:8; (d) Q26P, D29G, V32G, R34P, F71S, Q75H, D77G, E79G, T80P, E82W, or E185D relative to SEQ ID NO:8; (e) Q26E, D29G, V32G, R34G, F71S, Q75H, D77G, E79G, T80P, E82G, or E185D relative to SEQ ID NO:8; (f) Q26E, D29G, V32G, R34P, F71S, Q75H, D77G, E79G, T80P, E82G, or E185D relative to SEQ ID NO:8; (g) Q26P, D29G, V32G, R34G, F71S, Q75H, D77G, E79G, T80P, E82G, or E185D relative to SEQ ID NO:8; or (h) Q26P, D29G, V32G, R34P, F71S, Q75H, D77G, E79G, T80P, E82G, or E185D relative to SEQ ID NO:8.

In some embodiments, a variant NRF2 gene can comprise: (a) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (b) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (c) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (d) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:51 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (e) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (f) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; (g) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; or (h) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7.

CRISPR/Endonucleases

CRISPR/endonuclease (e.g., CRISPR/Cas9) systems are known in the art and are described, for example, in U.S. Pat. No. 9,925,248, which is incorporated by reference herein in its entirety. CRISPR-directed gene editing can identify and execute DNA cleavage at specific sites within the chromosome at a surprisingly high efficiency and precision. The natural activity of CRISPR/Cas9 is to disable a viral genome infecting a bacterial cell. Subsequent genetic reengineering of CRISPR/Cas function in human cells presents the possibility of disabling human genes at a significant frequency.

In bacteria, the CRISPR/Cas loci encode RNA-guided adaptive immune systems against mobile genetic elements (viruses, transposable elements and conjugative plasmids). Three types (I-III) of CRISPR systems have been identified. CRISPR clusters contain spacers, the sequences complementary to antecedent mobile elements. CRISPR clusters are transcribed and processed into mature CRISPR (Clustered Regularly Interspaced Short Palindromic Repeats) RNA (crRNA) containing a DNA binding region (spacer) which is complementary to the target gene. The CRISPR-associated endonuclease, Cas9, belongs to the type II CRISPR/Cas system and has strong endonuclease activity to cut target DNA. Cas9 is guided by a mature crRNA that contains about 20 base pairs (bp) of unique target sequence (called a spacer) and a trans-activated small RNA (tracrRNA) that serves as a guide for ribonuclease III-aided processing of pre-crRNA. The crRNA:tracrRNA duplex directs Cas9 to target DNA via complementary base pairing between the spacer on the crRNA and the complementary sequence (called protospacer) on the target DNA. Cas9 recognizes a trinucleotide (NGG) protospacer adjacent motif (PAM) to specify the cut site (the 3rd nucleotide from PAM).

The compositions described herein can include a nucleic acid encoding a CRISPR-associated endonuclease. The CRISPR-associated endonuclease can be, e.g., a class 1 CRISPR-associated endonuclease or a class 2 CRISPR-associated endonuclease. Class 1 CRISPR-associated endonucleases include type I, type III, and type IV CRISPR-Cas systems, which have effector molecules that comprise multiple subunits. For class 1 CRISPR-associated endonucleases, effector molecules can include, in some embodiments, Cas7 and Cas5, along with, in some embodiments, SS (Cas11) and Cas8a1; Cas8b1; Cas8c; Cas8u2 and Cas6; Cas3" and Cas10d; Cas SS (Cas11), Cas8e, and Cas6; Cas8f and Cas6f; Cas6f; Cas8-like (Csf1); SS (Cash) and Cas8-like (Csf1); or SS (Cas11) and Cas10. Class 1 CRISPR-associated endonucleases also be associated with, in some embodiments, target cleavage molecules, which can be Cas3 (type I) or Cas10 (type III) and spacer acquisition molecules such as, e.g., Cas1, Cas2, and/or Cas4. See, e.g., Koonin et al., Curr. Opin. Microbiol. 37:67-78 (2017); Strich & Chertow, J. Clin. Microbiol. 57:1307-18 (2019).

Class 2 CRISPR-associated endonucleases include type I, type V, and type VI CRISPR-Cas systems, which have a single effector molecule. For class 2 CRISPR-associated endonucleases, effector molecules can include, in some embodiments, Cas9, Cas12a (cpf1), Cas12b1 (c2c1), Cas12b2, Cas12c (c2c3), Cas12d (CasY), Cas12e (CasX), Cas12f1 (Cas14a), Cas12f2 (Cas14b), Cas12f3 (Cas14c), Cas12g, Cas12h, Cas12i, Cas12k (c2c5), Cas13a (c2c2), Cas13b1 (c2c6), Cas13b2 (c2c6), Cas13c (c2c7), Cas13d, c2c4, c2c8, c2c9, and/or c2c10. See, e.g., Koonin et al., Curr. Opin. Microbiol. 37:67-78 (2017); Strich & Chertow, J. Clin. Microbiol. 57:1307-18 (2019); Makarova et al., Nat. Rev. Microbiol. 18:67-83 (2020).

In some embodiments, the CRISPR-associated endonuclease can be a Cas9 nuclease. The Cas9 nuclease can have a nucleotide sequence identical to the wild type *Streptococcus pyogenes* sequence. In some embodiments, the CRISPR-associated endonuclease can be a sequence from other species, for example other *Streptococcus* species, such as *thermophilus; Pseudomona aeruginosa, Escherichia coli*, or other sequenced bacteria genomes and archaea, or other prokaryotic microorganisms. Such species include: *Acidovorax avenae, Actinobacillus pleuropneumoniae, Actinobacillus succinogenes, Actinobacillus suis, Actinomyces* sp., *Cycliphilusdenitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, Gammaproteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria meningitidis, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus aureus, Staphylococcus lugdunensis, Streptococcus* sp., *Subdoligranulum* sp., *Tistrella mobilis, Treponema* sp., and *Verminephrobacter eiseniae*.

Alternatively, the wild type *Streptococcus pyogenes* Cas9 sequence can be modified. The nucleic acid sequence can be codon optimized for efficient expression in mammalian cells, e.g., human cells. A Cas9 nuclease sequence codon optimized for expression in human cells sequence can be for example, the Cas9 nuclease sequence encoded by any of the expression vectors listed in Genbank accession numbers KM099231.1 GI:669193757; KM099232.1 GI:669193761; or KM099233.1 GI:669193765. Alternatively, the Cas9 nuclease sequence can be, for example, the sequence contained within a commercially available vector such as pX458, pX330 or pX260 from Addgene (Cambridge, Mass.). In some embodiments, the Cas9 endonuclease can have an amino acid sequence that is a variant or a fragment of any of the Cas9 endonuclease sequences of Genbank accession numbers KM099231.1 GI:669193757; KM099232.1 GI:669193761; or KM099233.1 GI:669193765 or Cas9 amino acid sequence of pX458, pX330 or pX260 (Addgene, Cambridge, Mass.). The Cas9 nucleotide sequence can be modified to encode biologically active variants of Cas9, and these variants can have or can include, for example, an amino acid sequence that differs from a wild type Cas9 by virtue of containing one or more mutations (e.g., an addition, deletion, or substitution mutation or a combination of such mutations). One or more of the substitution mutations can be a substitution (e.g., a conservative amino acid substitution). For example, a biologically active variant of a Cas9 polypeptide can have an amino acid sequence with at least or about 50% sequence identity (e.g., at least or about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity) to a wild type Cas9 polypeptide.

In some embodiments, the CRISPR-associated endonuclease can be a Cas12a nuclease. The Cas12a nuclease can have a nucleotide sequence identical to a wild type Prevotella or Francisella sequence. Alternatively, a wild type Prevotella or Francisella Cas12a sequence can be modified. The nucleic acid sequence can be codon optimized for efficient expression in mammalian cells, e.g., human cells. A Cas12a nuclease sequence codon optimized for expression in human cells sequence can be for example, the Cas9 nuclease sequence encoded by any of the expression vectors listed in Genbank accession numbers MF193599.1 GI: 1214941796, KY985374.1 GI: 1242863785, KY985375.1 GI: 1242863787, or KY985376.1 GI: 1242863789. Alternatively, the Cas12a nuclease sequence can be, for example, the sequence contained within a commercially available vector such as pAs-Cpf1 or pLb-Cpf1 from Addgene (Cambridge, Mass.). In some embodiments, the Cas12a endonuclease can have an amino acid sequence that is a variant or a fragment of any of the Cas12a endonuclease sequences of Genbank accession numbers MF193599.1 GI: 1214941796, KY985374.1 GI: 1242863785, KY985375.1 GI: 1242863787, or KY985376.1 GI: 1242863789 or Cas12a amino acid sequence of pAs-Cpf1 or pLb-Cpf1 (Addgene, Cambridge, Mass.). The Cas12a nucleotide sequence can be modified to encode biologically active variants of Cas12a, and these variants can have or can include, for example, an amino acid sequence that differs from a wild type Cas12a by virtue of containing one or more mutations (e.g., an addition, deletion, or substitution mutation or a combination of such mutations). One or more of the substitution mutations can be a substitution (e.g., a conservative amino acid substitution). For example, a biologically active variant of a Cas12a polypeptide can have an amino acid sequence with at least or about 50% sequence identity (e.g., at least or about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity) to a wild type Cas12a polypeptide.

The compositions described herein may also include sequence encoding a guide RNA (gRNA) comprising a DNA-binding domain that is complementary to a target domain from an NRF2 gene (e.g., a target domain from exon 1, 2, 3, 4, or 5 of an NRF2 gene), and a Clustered Regularly Interspaced Short Palindromic Repeat (CRISPR)-associated endonuclease protein-binding domain. In some embodiments, the gRNA comprises a DNA-binding domain that is complementary to a target domain from a variant NRF2 gene that is found only in cancer cells and not in wild-type NRF2 genes in normal (i.e., non-cancerous) cells (e.g., a target domain from exon 1, 2, 3, 4, or 5 of a variant NRF2 gene). The guide RNA sequence can be a sense or anti-sense sequence. The guide RNA sequence may include a proto-spacer adjacent motif (PAM). The sequence of the PAM can vary depending upon the specificity requirements of the CRISPR endonuclease used. In the CRISPR-Cas system derived from *S. pyogenes*, the target DNA typically immediately precedes a 5'-NGG proto-spacer adjacent motif (PAM). Thus, for the *S. pyogenes* Cas9, the PAM sequence can be AGG, TGG, CGG or GGG. Other Cas9 orthologs may have different PAM specificities. The specific sequence of the guide RNA may vary, but, regardless of the sequence, useful guide RNA sequences will be those that minimize off-target effects while achieving high efficiency. In some embodiments, the guide RNA sequence achieves complete ablation of the NRF2 gene. In some embodiments, the guide RNA sequence achieves complete ablation of a variant NRF2 gene without affecting expression or activity of a wild-type NRF2 gene.

In some embodiments, the DNA-binding domain varies in length from about 20 to about 55 nucleotides, for example, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, or about 55 nucleotides. In some embodiments, the Cas protein-binding domain is from about 30 to about 55 nucleotides in length, for example, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, or about 55 nucleotides.

In some embodiments, the compositions comprise one or more nucleic acid (i.e. DNA) sequences encoding the guide RNA and the CRISPR endonuclease. When the compositions are administered as a nucleic acid or are contained within an expression vector, the CRISPR endonuclease can be encoded by the same nucleic acid or vector as the guide RNA sequence. In some embodiments, the CRISPR endonuclease can be encoded in a physically separate nucleic acid from the guide RNA sequence or in a separate vector. The nucleic acid sequence encoding the guide RNA may comprise a DNA binding domain, a Cas protein binding domain, and a transcription terminator domain.

The nucleic acid encoding the guide RNA and/or the CRISPR endonuclease may be an isolated nucleic acid. An "isolated" nucleic acid can be, for example, a naturally-occurring DNA molecule or a fragment thereof, provided that at least one of the nucleic acid sequences normally found immediately flanking that DNA molecule in a naturally-occurring genome is removed or absent. Isolated nucleic acid molecules can be produced by standard techniques. For example, polymerase chain reaction (PCR) techniques can be used to obtain an isolated nucleic acid containing a nucleotide sequence described herein, including nucleotide sequences encoding a polypeptide described herein. PCR can be used to amplify specific sequences from DNA as well as RNA, including sequences from total genomic DNA or total cellular RNA. Various PCR methods are described in, for example, PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids also can be obtained by mutagenesis of, e.g., a naturally occurring portion of a Cas9-encoding DNA (in accordance with, for example, the formula above).

Recombinant constructs are also provided herein and can be used to transform cells in order to express the CRISPR endonuclease and/or a guide RNA complementary to an NRF2 gene (in some embodiments, a variant NRF2 gene found only in cancer cells). A recombinant nucleic acid construct may comprise a nucleic acid encoding a CRISPR endonuclease and/or a guide RNA complementary to an NRF2 gene (in some embodiments, a variant NRF2 gene found only in cancer cells), operably linked to a promoter suitable for expressing the CRISPR endonuclease and/or a guide RNA complementary to the NRF2 gene (in some embodiments, the variant NRF2 gene) in the cell. In some embodiments the nucleic acid encoding a CRISPR endonuclease is operably linked to the same promoter as the nucleic acid encoding the guide RNA. In other embodiments, the nucleic acid encoding a CRISPR endonuclease and the nucleic acid encoding the guide RNA are operably linked to different promoters. In some embodiments, the nucleic acid encoding a CRISPR endonuclease and/or the nucleic acid encoding a guide RNA are operably linked to a lung specific promoter. Suitable lung specific promoters include, but are not limited to, Clara cell 10-kDa protein ($CC_{10}$) (aka Scgb1a1) promoter (Stripp et al., J. Biol. Chem. 267:14703-12 (1992)), SFTPC promoter (Wert et al., Dev. Biol. 156: 426-43 (1993)), FOXJ1 promoter (Ostrowski et al., Mol.

Ther. 8:637-45 (2003)), aquaporin (Aqp5) promoter (Funaki et al., Am. J. Physiol. 275:C1151-57 (1998)), Keratin 5 (Krt5) promoter (Rock et al., Dis. Model Mech. 3:545-56 (2010)), Keratin 14 (Krt14) promoter (Rock et al., Dis. Model Mech. 3:545-56 (2010)), cytokeratin 18 (K18) promoter (Chow et al., Proc. Natl. Acad. Sci. USA 94:14695-14700 (1997)), surfactant protein B (SP-B) promoter (Strayer et al., Am. J. Physiol. Lung Cell Mol. Physiol. 282:L394-404 (2002)), TTF1 gene under the control of human telomerase reverse transcriptase promoter and human surfactant protein A1 promoter (Fukazawa et al., Cancer Res. 64:363-69 (2004)), surfactant protein C (SP-C) promoter (Zhuo et al., Transgenic Res. 15:543-55 (2006)), insulinoma-associated antigen-1 (INSM1) promoter (Li et al., Biochem. Biophys. Res. Commun. 236:776-81 (1997)), and surfactant protein A (SP-A) promoter (Bruno et al., J. Biol. Chem. 270:6531-36 (1995)).

In some embodiments, one or more CRISPR endonucleases and one or more guide RNAs may be provided in combination in the form of ribonucleoprotein particles (RNPs). An RNP complex can be introduced into a subject by means of, e.g., injection, electroporation, nanoparticles, vesicles, and/or with the assistance of cell-penetrating peptides.

DNA vectors containing nucleic acids such as those described herein also are also provided. A "DNA vector" is a replicon, such as a plasmid, phage, or cosmid, into which another DNA segment may be inserted so as to bring about the replication of the inserted segment. Generally, a DNA vector is capable of replication when associated with the proper control elements. Suitable vector backbones include, for example, those routinely used in the art such as plasmids, viruses, artificial chromosomes, BACs, YACs, or PACs. The term "DNA vector" includes cloning and expression vectors, as well as viral vectors and integrating vectors. An "expression vector" is a vector that includes a regulatory region. A wide variety of host/expression vector combinations may be used to express the nucleic acid sequences described herein. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The DNA vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

The DNA vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns.

As used herein, the term "operably linked" refers to positioning of a regulatory region (e.g. a promoter) and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Vectors include, for example, viral vectors (such as adenoviruses ("Ad"), adeno-associated viruses (AAV), and vesicular stomatitis virus (VSV) and retroviruses), liposomes and other lipid-containing complexes, and other macromolecular complexes capable of mediating delivery of a polynucleotide to a host cell. Direct injection of adenoviral vectors into lung tumors has been a routine procedure in clinical trials evaluating gene therapy of lung cancer. Dong et al., J. Int. Med. Res. 36, 1273-1287 (2008); Li et al., Cancer Gene Ther. 20, 251-259 (2013); Zhou, et al., Cancer Gene Ther. 23, 1-6 (2016). Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; Bio Techniques, 34: 167-171 (2003). A large variety of such vectors are known in the art and are generally available.

Suitable nucleic acid delivery systems include recombinant viral vector, typically sequence from at least one of an adenovirus, adenovirus-associated virus (AAV), helper-dependent adenovirus, retrovirus, or hemagglutinating virus of Japan-liposome (HVJ) complex. In such cases, the viral vector comprises a strong eukaryotic promoter operably linked to the polynucleotide e.g., a cytomegalovirus (CMV) promoter. The recombinant viral vector can include one or more of the polynucleotides therein, in some embodiments about one polynucleotide. In embodiments in which the polynucleotide is to be administered with a non-viral vector, use of between from about 0.1 nanograms to about 4000 micrograms will often be useful e.g., about 0.1 ng to about 3900 μg, about 0.1 ng to about 3800 μg, about 0.1 ng to about 3700 μg, about 0.1 ng to about 3600 μg, about 0.1 ng to about 3500 μg, about 0.1 ng to about 3400 μg, about 0.1 ng to about 3300 μg, about 0.1 ng to about 3200 μg, about 0.1 ng to about 3100 μg, about 0.1 ng to about 3000 μg, about 0.1 ng to about 2900 μg, about 0.1 ng to about 2800 μg, about 0.1 ng to about 2700 μg, about 0.1 ng to about 2600 μg, about 0.1 ng to about 2500 μg, about 0.1 ng to about 2400 μg, about 0.1 ng to about 2300 μg, about 0.1 ng to about 2200 μg, about 0.1 ng to about 2100 μg, about 0.1 ng to about 2000 μg, about 0.1 ng to about 1900 μg, about 0.1 ng to about 1800 μg, about 0.1 ng to about 1700 μg, about 0.1 ng to about 1600 μg, about 0.1 ng to about 1500 μg, about 0.1 ng to about 1400 μg, about 0.1 ng to about 1300 μg, about 0.1 ng to about 1200 μg, about 0.1 ng to about 1100 μg, about 0.1 ng to about 1000 μg, about 0.1 ng to about 900 μg, about 0.1 ng to about 800 μg, about 0.1 ng to about 700 μg, about 0.1 ng to about 600 μg, about 0.1 ng to about 500 μg, about 0.1 ng to about 400 μg, about 0.1 ng to about 300 μg, about 0.1 ng to about 200 μg, about 0.1 ng to about 100 μg, about 0.1 ng to about 90 μg, about 0.1 ng to about 80 μg, about 0.1 ng to about 70 μg, about 0.1 ng to about 60 μg, about 0.1 ng to about 50 μg, about 0.1 ng to about 40 μg, about 0.1 ng to about 30 μg, about 0.1 ng to about 20 μg, about 0.1 ng to about 10 μg, about 0.1 ng to about 1 μg, about 0.1 ng to about 900 ng, about 0.1 ng to about 800 ng, about 0.1 ng to about 700 ng, about 0.1 ng to about 600 ng, about 0.1 ng to about 500 ng, about 0.1 ng to about 400 ng, about 0.1 ng to about 300 ng, about 0.1 ng to about 200 ng, about 0.1 ng to about 100 ng, about 0.1 ng to about 90 ng, about 0.1 ng to about 80 ng, about 0.1 ng to about 70 ng, about 0.1 ng to about 60 ng, about 0.1 ng to about 50 ng, about 0.1 ng to about 40 ng, about 0.1 ng to about 30 ng, about 0.1 ng to about 20 ng, about 0.1 ng to about 10 ng, about 0.1 ng to about 1 ng, about 1 ng to about 4000 μg, about 1 ng to about 3900 μg, about 1 ng to about 3800 μg, about 1 ng to about 3700 μg, about 1 ng to about 3600 μg, about 1 ng to about 3500 μg, about 1 ng to about 3400 μg, about 1 ng to about 3300 μg, about 1 ng to about 3200 μg, about 1 ng to about 3100 μg, about 1 ng to about 3000 μg, about 1 ng to about 2900 μg, about 1 ng to about 2800 μg, about 1 ng to about 2700 μg, about 1 ng to about 2600 μg, about 1 ng to about 2500 μg, about 1 ng to about 2400 μg, about 1 ng to about 2300 μg, about 1 ng to about 2200 μg, about 1 ng to about 2100 μg, about 1 ng to about 2000 μg, about 1 ng to about 1900 μg, about 1 ng to about 1800 μg, about 1 ng to about 1700 μg, about 1 ng to about 1600 μg, about 1 ng to about 1500 μg, about 1 ng to about 1400 μg, about 1 ng to about 1300 μg, about 1 ng to about 1200 μg, about 1 ng to about 1100 μg, about 1 ng to about 1000 μg, about 1 ng to about 900 μg, about 1 ng to about 800 μg, about 1 ng to about 700 μg, about 1 ng to about 600 μg, about 1 ng to about 500 μg, about 1 ng to about 400 μg, about 1 ng to about 300 μg, about 1 ng to about 200 μg, about 1 ng to about 100 μg, about 1 ng to about 90 μg, about 1 ng to about 80 μg, about 1 ng to about 70 μg, about 1 ng to about 60 μg, about 1 ng to about 50 μg, about 1 ng to about 40 μg, about 1 ng to about 30 μg, about 1 ng to about 20 μg, about 1 ng to about 10 μg, about 1 ng to about 1 μg, about 1 ng to about 900 ng, about 1 ng to about 800 ng, about 1 ng to about 700 ng, about 1 ng to about 600 ng, about 1 ng to about 500 ng, about 1 ng to about 400 ng, about 1 ng to about 300 ng, about 1 ng to about 200 ng, about 1 ng to about 100 ng, about 1 ng to about 90 ng, about 1 ng to about 80 ng, about 1 ng to about 70 ng, about 1 ng to about 60 ng, about 1 ng to about 50 ng, about 1 ng to about 40 ng, about 1 ng to about 30 ng, about 1 ng to about 20 ng, about 1 ng to about 10 ng, about 10 ng to about 4000 μg, about 20 ng to about 4000 μg, about 30 ng to about 4000 μg, about 40 ng to about 4000 μg, about 50 ng to about 4000 μg, about 60 ng to about 4000 μg, about 70 ng to about 4000 μg, about 80 ng to about 4000 μg, about 90 ng to about 4000 μg, about 100 ng to about 4000 μg, about 200 ng to about 4000 μg, about 300 ng to about 4000 μg, about 400 ng to about 4000 μg, about 500 ng to about 4000 μg, about 600 ng to about 4000 μg, about 700 ng to about 4000 μg, about 800 ng to about 4000 μg, about 900 ng to about 4000 μg, about 1 μg to about 4000 μg, 10 μg to about 4000 μg, 20 μg to about 4000 μg, 30 μg to about 4000 μg, 40 μg to about 4000 μg, 50 μg to about 4000 μg, 60 μg to about 4000 μg, 70 μg to about 4000 μg, 80 μg to about 4000 μg, 90 μg to about 4000 μg, 100 μg to about 4000 μg, 200 μg to about 4000 μg, 300 μg to about 4000 μg, 400 μg to about 4000 μg, 500 μg to about 4000 μg, 600 μg to about 4000 μg, 700 μg to about 4000 μg, 800 μg to about 4000 μg, 900 μg to about 4000 μg, 1000 μg to about 4000 μg, 1100 μg to about 4000 μg, 1200 μg to about 4000 μg, 1300 μg to about 4000 μg, 1400 μg to about 4000 μg, 1500 μg to about 4000 μg, 1600 μg to about 4000 μg, 1700 μg to about 4000 μg, 1800 μg to about 4000 μg, 1900 μg to about 4000 μg, 2000 μg to about 4000 μg, 2100 μg to about 4000 μg, 2200 μg to about 4000 μg, 2300 μg to about 4000 μg, 2400 μg to about 4000 μg, 2500 μg to about 4000 μg, 2600 μg to about 4000 μg, 2700 μg to about 4000 μg, 2800 μg to about 4000 μg, 2900 μg to about 4000 μg, 3000 μg to about 4000 μg, 3100 μg to about 4000 μg, 3200 μg to about 4000 μg, 3300 μg to about 4000 μg, 3400 μg to about 4000 μg, 3500 μg to about 4000 μg, 3600 μg to about 4000 μg, 3700 μg to about 4000 μg, 3800 μg to about 4000 μg, or 3900 μg to about 4000 μg.

Additional vectors include viral vectors, fusion proteins and chemical conjugates. Retroviral vectors include Moloney murine leukemia viruses and HIV-based viruses. One HIV-based viral vector comprises at least two vectors wherein the gag and pol genes are from an HIV genome and the env gene is from another virus. DNA viral vectors include pox vectors such as orthopox or avipox vectors, herpesvirus vectors such as a herpes simplex I virus (HSV) vector [Geller, A. I. et al., J. Neurochem, 64: 487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A.:90 7603 (1993); Geller, A. I., et al., Proc Natl. Acad. Sci USA: 87:1149 (1990)], Adenovirus Vectors [LeGal LaSalle et al., Science, 259:988 (1993); Davidson, et al., Nat. Genet. 3: 219 (1993); Yang, et al., J. Virol. 69: 2004 (1995)] and Adeno-associated Virus Vectors [Kaplitt, M. G., et al., Nat. Genet. 8:148 (1994)].

If desired, the polynucleotides described here may also be used with a microdelivery vehicle such as cationic liposomes, adenoviral vectors, and exosomes. For a review of the procedures for liposome preparation, targeting and delivery of contents, see Mannino and Gould-Fogerite, BioTechniques, 6:682 (1988). See also, Feigner and Holm, Bethesda Res. Lab. Focus, 11(2):21 (1989) and Maurer, R. A., Bethesda Res. Lab. Focus, 11(2):25 (1989). In some embodiments, exosomes may be used for delivery of a nucleic acid encoding a CRISPR endonuclease and/or guide RNA to a target cell, e.g. a cancer cell. Exosomes are nanosized vesicles secreted by a variety of cells and are comprised of cellular membranes. Exosomes can attach to target cells by a range of surface adhesion proteins and vector ligands (tetraspanins, integrins, CD11b and CD18 receptors), and deliver their payload to target cells. Several studies indicate that exosomes have a specific cell tropism, according to their characteristics and origin, which can be used to target them to disease tissues and/or organs. See Batrakova et al., 2015, J Control Release 219: 396-405. For example, cancer-derived exosomes function as natural carriers that can efficiently deliver CRISPR/Cas9 plasmids to cancer cells. See Kim et al., 2017, J Control Release 266: 8-16.

Replication-defective recombinant adenoviral vectors, can be produced in accordance with known techniques. See, Quantin, et al., Proc. Natl. Acad. Sci. USA, 89:2581-2584 (1992); Stratford-Perricadet, et al., J. Clin. Invest., 90:626-630 (1992); and Rosenfeld, et al., Cell, 68:143-155 (1992).

Another delivery method is to use single stranded DNA producing vectors which can produce the expressed products intracellularly. See for example, Chen et al., Bio Techniques, 34: 167-171 (2003), which is incorporated herein, by reference, in its entirety.

Pharmaceutical Compositions

Any of the pharmaceutical compositions disclosed herein can be formulated for use in the preparation of a medicament, and particular uses are indicated below in the context of treatment, e.g., the treatment of a subject having cancer. When employed as pharmaceuticals, any of the nucleic acids and vectors can be administered in the form of pharmaceutical compositions. Administration may be pulmonary (e.g., by inhalation or insufflation of powders or aerosols, including by nebulizer; intratracheal, intranasal, epidermal and transdermal), topical (including ophthalmic and to mucous membranes including intranasal, vaginal and rectal delivery), ocular, oral or parenteral. Parenteral administration includes intravenous, intra-arterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

In some embodiments, pharmaceutical compositions can contain, as the active ingredient, nucleic acids and vectors described herein in combination with one or more pharmaceutically acceptable carriers. The term "pharmaceutically acceptable" refers to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance. In making the pharmaceutical compositions disclosed herein, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), lotions, creams, ointments, gels, soft and hard gelatin capsules, suppositories, sterile injectable solutions, and sterile packaged powders. As is known in the art, the type of diluent can vary depending upon the intended route of administration. The resulting compositions can include additional agents, such as preservatives. In some embodiments, the carrier can be, or can include, a lipid-based or polymer-based colloid. In some embodiments, the carrier material can be a colloid formulated as a liposome, a hydrogel, a microparticle, a nanoparticle, or a block copolymer micelle. As noted, the carrier material can form a capsule, and that material may be a polymer-based colloid.

The nucleic acid sequences disclosed herein can be delivered to an appropriate cell of a subject, e.g. a cancer cell. This can be achieved by, for example, the use of a polymeric, biodegradable microparticle or microcapsule delivery vehicle, sized to optimize phagocytosis by phagocytic cells such as macrophages. Delivery of "naked DNA" (i.e., without a delivery vehicle) to an intramuscular, intradermal, or subcutaneous site, is another means to achieve in vivo expression. In the relevant polynucleotides (e.g., expression vectors) the nucleic acid sequence encoding the isolated nucleic acid sequence comprising a sequence encoding a CRISPR-associated endonuclease and a guide RNA can be operatively linked to a promoter or enhancer-promoter combination. Promoters and enhancers are described above.

In some embodiments, the pharmaceutical compositions can be formulated as a nanoparticle, for example, nanoparticles comprised of a core of high molecular weight linear polyethylenimine (LPEI) complexed with DNA and surrounded by a shell of polyethyleneglycol-modified (PEGylated) low molecular weight LPEI.

The nucleic acids and vectors may also be applied to a surface of a device (e.g., a catheter) or contained within a pump, patch, or other drug delivery device. The nucleic acids and vectors disclosed herein can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary).

In some embodiments, the compositions can be formulated as a nanoparticle encapsulating a nucleic acid encoding a CRISPR-associated endonuclease and a guide RNA sequence complementary to an NRF2 gene (or, in some embodiments, a variant NRF2 gene), or vector comprising a nucleic acid encoding a CRISPR-associated endonuclease and a guide RNA sequence complementary to an NRF2 gene (or, in some embodiments, a variant NRF2 gene).

Methods of Reducing NRF2 Expression or Activity in a Cell

In certain aspects, the disclosure relates to a method of reducing NRF2 expression or activity in a cell comprising introducing into the cell (a) one or more DNA sequence(s) encoding a guide RNA (gRNA) that is complementary to a target sequence in the NRF2 gene and (b) a nucleic acid sequence encoding a Clustered Regularly Interspaced Short Palindromic Repeat (CRISPR)-associated endonuclease, whereby the gRNA hybridizes to the NRF2 gene and the CRISPR-associated endonuclease cleaves the NRF2 gene, and wherein NRF2 expression or activity is reduced in the cell relative to a cell in which the one or more DNA sequences encoding the gRNA and the nucleic acid sequence encoding the CRISPR-associated nuclease are not introduced.

Reducing NRF2 expression in the cell may comprise reducing expression of NRF2 mRNA in the cell, reducing expression of the NRF2 protein in the cell, or both. In some embodiments, expression of one or more allele(s) of the NRF2 gene is reduced. In some embodiments, introducing the one or more DNA sequence(s) encoding the gRNA and the nucleic acid sequence encoding a CRISPR-associated endonuclease into the cell reduces NRF2 expression and/or activity in the cell, but does not completely eliminate it. In other embodiments, NRF2 expression and/or activity in the cell are completely eliminated.

The gRNA may be complementary to a target sequence in an exon of the NRF2 gene. In a particular embodiment, the gRNA is complementary to a target sequence in exon 1, 2, 3, 4, or 5 of the NRF2 gene. In some embodiments, the gRNA is encoded by a single DNA sequence. In other embodiments, the gRNA is encoded by two or more DNA sequences. For example, in some embodiments, the gRNA is encode by a first DNA sequence encoding a trans-activated small RNA (tracrRNA) and a second DNA sequence encoding a CRISPR RNA (crRNA). The tracrRNA and crRNA may hybridize within the cell to form the guide RNA. Accordingly, in some embodiments, the gRNA comprises a trans-activated small RNA (tracrRNA) and a CRISPR RNA (crRNA).

In some embodiments, the guide RNA is complementary to a variant NRF2 gene that is found only in cancer cells and not in wild-type NRF2 genes in normal (i.e., non-cancerous) cells (e.g. exon 1, 2, 3, 4, or 5). In some embodiments, the guide RNA is complementary to a sequence in exon 2 of a variant NRF2 gene that is found only in cancer cells. In some embodiments, introducing the one or more DNA sequence(s) encoding the gRNA and the nucleic acid sequence encoding a CRISPR-associated endonuclease into the cell reduces variant NRF2 expression and/or activity in the cell, but does not completely eliminate it. In other embodiments, variant NRF2 expression and/or activity in the cell are completely eliminated.

In some embodiments, CRISPR-associated endonucleases suitable for use in reducing expression of the variant NRF2 gene include, but are not limited to, a class 1 CRISPR-associated endonucleases such as, e.g., Cas7 and Cas5, along with, in some embodiments, SS (Cas11) and Cas8a1; Cas8b1; Cas8c; Cas8u2 and Cas6; Cas3" and Cas10d; Cas SS (Cas11), Cas8e, and Cas6; Cas8f and Cas6f; Cas6f; Cas8-like (Csf1); SS (Cas11) and Cas8-like (Csf1); or SS (Cas11) and Cas10. Class 2 CRISPR-associated endonucleases include type I, type V, and type VI CRISPR-Cas systems, which have a single effector molecule. In some embodiments, CRISPR-associated endonucleases suitable for use in reducing expression of the variant NRF2 gene include, but are not limited to, class 2 CRISPR-associated endonucleases such as, e.g., Cas9, Cas12a, Cas12b, Cas12c, Cas12d, Cas13a, Cas13b, Cas13c, c2c4, c2c5, c2c8, c2c9, and/or c2c10. In some embodiments, CRISPR-associated endonucleases suitable for use in reducing expression of the variant NRF2 gene include, but are not limited to, CasX, CasY, and/or MAD6 (see, e.g., Liu et al., Nature 566:218-23 (2019)).

Any cell containing a variant NRF2 gene may be suitable for use in the methods of reducing variant NRF2 expression or activity described herein. In some embodiments, the cell is a eukaryotic cell, e.g. a mammalian cell. In some embodiments, the cell is a human cell. In some embodiments, the NRF2 gene is a human NRF2 gene.

In certain aspects, the disclosure also relates to a cell comprising a mutated NRF2 gene produced by the methods of reducing NRF2 expression or activity described herein. In some embodiments, the mutated NRF2 gene comprises an insertion or a deletion relative to the variant NRF2 gene. In some embodiments, the insertion or deletion occurs within 1, 2, 3, 4, 5, 6, 7, 8, 9, 10, 11, 12, 13, 14, 15, 16, 17, 18, 19 or 20 nucleotide(s) of a protospacer adjacent motif sequence (PAM) in the NRF2 gene.

Methods for Treatment of Cancer

In certain aspects, the disclosure relates to a method of treating cancer in a subject comprising administering to the subject a therapeutically effective amount of a pharmaceutical composition comprising a Clustered Regularly Interspaced Short Palindromic Repeat (CRISPR)-associated endonuclease and a guide RNA that is complementary to a target domain from an NRF2 gene in the subject. In certain aspects, the disclosure relates to a method of treating cancer in a subject comprising administering to the subject a therapeutically effective amount of a pharmaceutical composition comprising a Clustered Regularly Interspaced Short Palindromic Repeat (CRISPR)-associated endonuclease and a guide RNA that is complementary to a target domain from a variant NRF2 gene in a cancer cell in the subject.

In certain aspects, the disclosure relates to a method of treating cancer in a subject comprising administering to the subject a therapeutically effective amount of a pharmaceutical composition comprising: (a) a DNA sequence encoding a guide RNA that is complementary to a target domain from an NRF2 gene in the subject; and (b) a nucleic acid sequence encoding a Clustered Regularly Interspaced Short Palindromic Repeat (CRISPR)-associated endonuclease. In some embodiments, the guide RNA is complementary to a variant NRF2 gene that is found only in cancer cells and not in wild-type NRF2 genes in normal (i.e., non-cancerous) cells (e.g. exon 1, 2, 3, 4, or 5). In some embodiments, the guide RNA is complementary to a sequence in exon 2 of a variant NRF2 gene that is found only in cancer cells.

In certain embodiments, the cancer is a solid tumor. In certain embodiments, the cancer is a non-small cell lung cancer. In certain embodiments, the cancer is treated only with the pharmaceutical composition comprising a Clustered Regularly Interspaced Short Palindromic Repeat (CRISPR)-associated endonuclease and a guide RNA that is complementary to a target domain from an NRF2 gene in the subject, or only with the pharmaceutical composition comprising: (a) a DNA sequence encoding a guide RNA that is complementary to a target domain from an NRF2 gene in the subject; and (b) a nucleic acid sequence encoding a Clustered Regularly Interspaced Short Palindromic Repeat (CRISPR)-associated endonuclease. In some embodiments, the guide RNA is complementary to a variant NRF2 gene that is found only in cancer cells and not in wild-type NRF2 genes in normal (i.e., non-cancerous) cells (e.g. exon 1, 2, 3, 4, or 5). In some embodiments, the guide RNA is complementary to a sequence in exon 2 of a variant NRF2 gene that is found only in cancer cells. In certain embodiments, the cancer is treated with the pharmaceutical compositions as described herein and an additional agent, e.g. a chemotherapeutic agent. In certain embodiments, treatment with the chemotherapeutic agent is initiated at the same time as treatment with the pharmaceutical composition. In certain embodiments, the treatment with the chemotherapeutic agent is initiated after the treatment with the pharmaceutical composition is initiated. In certain embodiments, treatment with the chemotherapeutic agent is initiated at before the treatment with the pharmaceutical composition.

In certain embodiments, the pharmaceutical compositions of the present disclosure may be utilized for the treatment of cancer wherein the subject has failed at least one prior chemotherapeutic regimen. For example, in some embodiments, the cancer is resistant to one or more chemotherapeutic agents. Accordingly, the present disclosure provides methods of treating cancer in a subject, wherein the subject has failed at least one prior chemotherapeutic regimen for the cancer, comprising administering the pharmaceutical compositions as described herein to the subject in an amount sufficient to treat the cancer, thereby treating the cancer. The pharmaceutical compositions described herein may also be utilized for inhibiting tumor cell growth in a subject wherein the subject has failed at least one prior chemotherapeutic regimen. Accordingly, the present disclosure further provides methods of inhibiting tumor cell growth in a subject, e.g. wherein the subject has failed at least one prior chemotherapeutic regimen, comprising administering the pharmaceutical compositions described herein to the subject, such that tumor cell growth is inhibited. In certain embodiments, the subject is a mammal, e.g. a human.

For example, the pharmaceutical compositions described herein may be administered to a subject in an amount sufficient to reduce proliferation of cancer cells relative to cancer cells that are not treated with the pharmaceutical composition. The pharmaceutical composition may reduce cancer cell proliferation by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% relative to cancer cells that are not treated with the pharmaceutical composition.

In some embodiments, the pharmaceutical composition is administered in an amount sufficient to reduce tumor growth relative to a tumor that is not treated with the pharmaceutical composition. The pharmaceutical composition may reduce tumor growth by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% relative to cancer cells that are not treated with the pharmaceutical composition. In a particular embodiment, administration of the pharmaceutical composition to the subject completely inhibits tumor growth.

In one embodiment, administration of a pharmaceutical composition as described herein, achieves at least stable disease, reduces tumor size, inhibits tumor growth and/or prolongs the survival time of a tumor-bearing subject as compared to an appropriate control. Accordingly, this disclosure also relates to a method of treating tumors in a human or other animal, including a subject, who has failed at least one prior chemotherapeutic regimen, by administering to such human or animal an effective amount of a pharmaceutical composition described herein. One skilled in the art would be able, by routine experimentation with the guidance provided herein, to determine what an effective amount of the pharmaceutical composition would be for the purpose of treating malignancies including in a subject who has failed at least one prior chemotherapeutic regimen. For example, a therapeutically active amount of the pharmaceutical composition may vary according to factors such as the disease stage (e.g., stage I versus stage IV), age, sex, medical complications, and weight of the subject, and the ability of the pharmaceutical composition to elicit a desired response in the subject. The dosage regimen may be adjusted to provide the optimum therapeutic response. For example, several divided doses may be administered daily, the dose may be administered by continuous infusion, or the dose may be proportionally reduced as indicated by the exigencies of the therapeutic situation.

In certain embodiments, the methods further include a treatment regimen which includes any one of or a combination of surgery, radiation, chemotherapy, e.g., hormone therapy, antibody therapy, therapy with growth factors, cytokines, and anti-angiogenic therapy.

Cancers for treatment using the methods of the disclosed herein include, for example, all types of cancer or neoplasm or malignant tumors found in mammals, including, but not limited to: leukemias, lymphomas, melanomas, carcinomas and sarcomas. In one embodiment, cancers for treatment using the methods of disclosed herein include melanomas, carcinomas and sarcomas. In some embodiments, the coenzyme Q10 compositions are used for treatment, of various types of solid tumors, for example breast cancer, bladder cancer, colon and rectal cancer, endometrial cancer, kidney (renal cell) cancer, lung cancer, melanoma, pancreatic cancer, prostate cancer, thyroid cancer, skin cancer, bone cancer, brain cancer, cervical cancer, liver cancer, stomach cancer, mouth and oral cancers, neuroblastoma, testicular cancer, uterine cancer, thyroid cancer, head and neck, kidney, lung, non-small cell lung, melanoma, mesothelioma, ovary, sarcoma, stomach, uterus and medulloblastoma, and vulvar cancer. In certain embodiments, solid tumors include breast cancer, including triple negative breast cancer. In certain embodiments, skin cancer includes melanoma, squamous cell carcinoma, cutaneous T-cell lymphoma (CTCL). In certain embodiments, the cancer includes leukemia. In certain embodiments, the cancer is selected from the group consisting of lung cancer, melanoma, esophageal squamous cancer (ESC), head and neck squamous cell carcinoma (HNSCC), and breast cancer.

In a particular embodiment, the cancer is lung cancer, e.g. non-small-cell lung cancer (NSCLC). In some embodiments, the NSCLC is adenocarcinoma, squamous cell carcinoma, or large cell carcinoma. Beyond the current well-established combinatorial drug strategies used to treat NSCLC, several different combinatorial approaches are also being investigated for the treatment of cancers. For example, the use of an oncolytic virus that infects tumor cells has been found to enhance the activity of chemotherapy. Infection with myxoma virus combined with cisplatin or gemcitabine efficiently destroyed ovarian cancer cells at much lower dosages than needed without viral addition. Nounamo et al., Mol. Ther. oncolytics 6, 90-99 (2017). The use of oncolytic virus therapy and cytotoxic chemotherapy for improved effectiveness of cancer treatment is an active area of development. Wennier, et al., Curr. Pharm. Biotechnol. 13, 1817-33 (2012); Pandha, et al., Oncolytic Virotherapy 5, 1 (2016). Infection with a replication competent virus before treatment with cisplatin markedly enhances the therapeutic benefit of chemotherapy.

With the usage of targeted therapy (targeting EGFR mutation, ALK rearrangement, etc.) and immunotherapy (checkpoint inhibitors, anti-PD1, anti-CTLA4, etc.), the clinical management of NSCLC has greatly improved. Patients can have a longer and better quality of life. However, these therapies cannot solve all the problems. For example, agents that target specific molecules typically have a response rate of ~70%. However, after a median period of 8-16 months, due to the inevitable resistance, relapse happens in almost all patients. Anichini, et al., Cancer Immunol. Immunother. 67, 1011-1022 (2018). In regards to immunotherapy, though pembrolizumab (Keytruda) can be used as first treatment in certain lung cancer patients, only a fraction of them will respond. Bianco, et al., Curr. Opin. Pharmacol. 40, 46-50 (2018).

On the other hand, chemotherapy is still indispensable in the lung cancer treatment paradigm. In patients with locoregional NSCLC, chemotherapy is the only systemic therapy proven to improve curability when combined with surgery or radiation. Wang, et al., Investig. Opthalmology Vis. Sci. 58, 3896 (2017). In patients with metastasis, chemotherapy is still the mainstay of care for those who have developed resistance to targeted therapy agents. Meanwhile, it also has the potential to stimulate the immune system to boost the effectiveness of immunotherapy.

Combination Therapies

In certain embodiments, the pharmaceutical compositions described herein can be used in combination therapy with at least one additional anticancer agent, e.g., a chemotherapeutic agent.

Small molecule chemotherapeutic agents generally belong to various classes including, for example: 1. Topoisomerase II inhibitors (cytotoxic antibiotics), such as the anthracyclines/anthracenediones, e.g., doxorubicin, epirubicin, idarubicin and nemorubicin, the anthraquinones, e.g., mitoxantrone and losoxantrone, and the podophillotoxines, e.g., etoposide and teniposide; 2. Agents that affect microtubule formation (mitotic inhibitors), such as plant alkaloids (e.g., a compound belonging to a family of alkaline, nitrogen-containing molecules derived from plants that are biologically active and cytotoxic), e.g., taxanes, e.g., paclitaxel and docetaxel, and the vinka alkaloids, e.g., vinblastine, vincristine, and vinorelbine, and derivatives of podophyllotoxin; 3. Alkylating agents, such as nitrogen mustards, ethyleneimine compounds, alkyl sulphonates and other compounds with an alkylating action such as nitrosoureas, dacarbazine, cyclophosphamide, ifosfamide and melphalan; 4. Antimetabolites (nucleoside inhibitors), for example, folates, e.g., folic acid, fiuropyrimidines, purine or pyrimidine analogues such as 5-fluorouracil, capecitabine, gemcitabine, methotrexate, and edatrexate; 5. Topoisomerase I inhibitors, such as topotecan, irinotecan, and 9-nitrocamptothecin, camptothecin derivatives, and retinoic acid; and 6. Platinum compounds/complexes, such as cisplatin, oxaliplatin, and carboplatin. Exemplary chemotherapeutic agents for use in the methods of disclosed herein include, but are not limited to, amifostine (ethyol), cisplatin, dacarbazine (DTIC), dactinomycin, mechlorethamine (nitrogen mustard), streptozocin, cyclophosphamide, carrnustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-I 1, 10-hydroxy-7-ethylcamptothecin (SN38), capecitabine, ftorafur, 5'deoxyflurouridine, UFT, eniluracil, deoxycytidine, 5-azacytosine, 5-azadeoxycytosine, allopurinol, 2-chloro adenosine, trimetrexate, aminopterin, methylene-10-deazaaminopterin (MDAM), oxaplatin, picoplatin, tetraplatin, satraplatin, platinum-DACH, ormaplatin, CI-973 (and analogs thereof), JM-216 (and analogs thereof), epirubicin, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, acyclovir, valacyclovir, ganciclovir, amantadine, rimantadine, lamivudine, zidovudine, bevacizumab, trastuzumab, rituximab, Pentostatin, floxuridine, fludarabine, hydroxyurea, ifosfamide, idarubicin, mesna, irinotecan, mitoxantrone, topotecan, leuprolide, megestrol, melphalan, plicamycin, mitotane, pegaspargase, pipobroman, tamoxifen, teniposide, testolactone, thiotepa, uracil mustard, vinorelbine, chlorambucil, mTor, epidermal growth factor receptor (EGFR), and fibroblast growth factors (FGF) and combinations thereof which are readily apparent to one of skill in the art based on the appropriate standard of care for a particular tumor or cancer. In a particular embodiment, the chemotherapeutic agent is selected from the group consisting of cisplatin, vinorelbine, carboplatin, and combinations thereof (e.g., cisplatin and vinorelbine; cisplatin and carboplatin; vinorelbine and carboplatin; cisplatin, vinorelbine, and carboplatin).

In some embodiments, the pharmaceutical composition is administered in an amount sufficient to reduce tumor growth relative to a tumor that is treated with the at least one chemotherapeutic agent but is not treated with the pharmaceutical composition. The pharmaceutical composition may reduce tumor growth by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% relative to cancer cells that are treated with the at least one chemotherapeutic agent but are not treated with the pharmaceutical composition.

TABLE 2

Description of Sequences

| SEQ ID NO: | Description | Sequence |
|---|---|---|
| 1 | Guide RNA1 (gRNA1) recognition element | 3'-AGCTACTCTGGCCCTTATAG<u>TCC</u>-5' |
| 2 | Guide RNA1 (gRNA1) | 5'-UCGAUGUGACCGGGAAUAUC<u>AGG</u>-3' |
| 3 | Guide RNA2 gRNA2) recognition element (from Sanjana et al., Nat. Methods 11(8):783-84 (2014)) | 3'-ACTAAATCTGCCATACGTTG<u>TCC</u>-5' |
| 4 | Guide RNA2 gRNA2) | 5'-UGAUUUAGACGGUAUGCAAC<u>AGG</u>-3' |
| 5 | PCR primer, forward | GTAGTGGTGCCTTAGAGCTTACTCATCC |
| 6 | PCR primer, reverse | CTAGCATGGGCAGTACTCATGACTAAG |
| 7 | human NRF2 DNA sequence | NCBI Reference Sequence NM_006164.5 |
| 8 | human NRF2 amino acid sequence | NCBI Reference Sequence NP_006155.2 |

PAM sequence underlined.

NM_006164.5

(SEQ ID NO: 7)

```
   1 gattaccgag tgccgggag cccggaggag ccgccgacgc agccgccacc gccgccgccg
  61 ccgccaccag agccgccctg tccgcgccgc gcctcggcag ccggaacagg gccgccgtcg
 121 gggagcccca acacacggtc cacagctcat catgatggac ttggagctgc cgccgccggg
 181 actcccgtcc cagcaggaca tggatttgat tgacatactt tggaggcaag atatagatct
 241 tggagtaagt cgagaagtat ttgacttcag tcagcgacgg aaagagtatg agctggaaaa
 301 acagaaaaaa cttgaaaagg aaagacaaga caactccaa aaggagcaag agaaagcctt
 361 tttcgctcag ttacaactag atgaagagac aggtgaattt ctcccaattc agccagccca
 421 gcacatccag tcagaaacca gtggatctgc caactactcc caggttgccc acattcccaa
 481 atcagatgct ttgtactttg atgactgcat gcagcttttg cgcagacat tcccgtttgt
 541 agatgacaat gaggtttctt cggctacgtt tcagtcactt gttcctgata ttcccggtca
 601 catcgagagc ccagtcttca ttgctactaa tcaggctcag tcacctgaaa cttctgttgc
 661 tcaggtagcc cctgttgatt tagacggtat gcaacaggac attgagcaag tttgggagga
 721 gctattatcc attcctgagt tacagtgtct taatattgaa aatgacaagc tggttgagac
 781 taccatggtt ccaagtccag aagccaaact gacagaagtt gacaattatc attttactc
 841 atctataccc tcaatggaaa agaagtagg taactgtagt ccacatttc ttaatgcttt
 901 tgaggattcc ttcagcagca tcctctccac agaagacccc aaccagttga cagtgaactc
 961 attaaattca gatgccacag tcaacacaga ttttggtgat gaattttat ctgctttcat
1021 agctgagccc agtatcagca acagcatgcc ctcacctgct actttaagcc attcactctc
1081 tgaacttcta aatgggccca ttgatgtttc tgatctatca cttttgcaaag ctttcaacca
1141 aaaccaccct gaaagcacag cagaattcaa tgattctgac tccggcattt cactaaacac
1201 aagtccagt gtggcatcac cagaacactc agtggaatct tccagctatg agacacact
1261 acttggcctc agtgattctg aagtggaaga gctagatagt gcccctggaa gtgtcaaaca
1321 gaatggtcct aaaacaccag tacattcttc tggggatatg gtacaaccct tgtcaccatc
1381 tcaggggcag agcactcacg tgcatgatgc ccaatgtgag aacacaccag agaaagaatt
```

```
-continued
1441 gcctgtaagt cctggtcatc ggaaaacccc attcacaaaa gacaaacatt caagccgctt 1501 ggaggctcat ctcacaagag atgaacttag ggcaaaagct ctccatatcc cattccctgt 1561 agaaaaaatc attaacctcc ctgttgttga cttcaacgaa atgatgtcca aagagcagtt 1621 caatgaagct caacttgcat taattcggga tatacgtagg aggggtaaga ataaagtggc 1681 tgctcagaat tgcagaaaaa gaaaactgga aaatatagta gaactagagc aagatttaga 1741 tcatttgaaa gatgaaaaag aaaaattgct caaagaaaaa ggagaaaatg acaaaagcct 1801 tcacctactg aaaaaacaac tcagcacctt atatctcgaa gttttcagca tgctacgtga 1861 tgaagatgga aaaccttatt ctcctagtga atactccctg cagcaaacaa gagatggcaa 1921 tgttttcctt gttcccaaaa gtaagaagcc agatgttaag aaaaactaga tttaggagga 1981 tttgaccttt tctgagctag ttttttttgta ctattatact aaaagctcct actgtgatgt 2041 gaaatgctca tactttataa gtaattctat gcaaaatcat agccaaaact agtatagaaa 2101 ataatacgaa actttaaaaa gcattggagt gtcagtatgt tgaatcagta gtttcacttt 2161 aactgtaaac aatttcttag gacaccattt gggctagttt ctgtgtaagt gtaaatacta 2221 caaaaactta tttatactgt tcttatgtca tttgttatat tcatagattt atatgatgat 2281 atgacatctg gctaaaagaa aattattgca aaactaacca ctatgtactt ttttataaat 2341 actgtatgga caaaaaatgg cattttttat attaaattgt ttagctctgg caaaaaaaaa 2401 aaattttaag agctggtact aataaaggat tattatgact gttaaa
```

```
NP_006155.2
                                                            (SEQ ID NO: 8)
  1 mmdlelpppg lpsqqdmdli dilwrqdidl gvsrevfdfs qrrkeyelek qkklekerqe 61 qlqkeqekaf faqlqldeet geflpiqpaq hiqsetsgsa nysqvahipk sdalyfddcm 121 qllaqtfpfv ddnevssatf qslvpdipgh iespvfiatn qaqspetsva qvapvdldgm 181 qqdieqvwee llsipelqcl niendklvet tmvpspeakl tevdnyhfys sipsmekevg 241 ncsphflnaf edsfssilst edpnqltvns lnsdatvntd fgdefysafi aepsisnsmp 301 spatlshsls ellngpidvs dlslckafnq nhpestaefn dsdsgislnt spsvaspehs 361 vesssygdtl lglsdsevee ldsapgsvkq ngpktpvhss gdmvqplsps qgqsthvhda 421 qcentpekel pvspghrktp ftkdkhssrl eahltrdelr akalhipfpv ekiinlpvvd 481 fnemmskeqf neaqlalird irrrgknkva aqncrkrkle niveleqdld hlkdekekll 541 kekgendksl hllkkqlstl ylevfsmlrd edgkpyspse yslqqtrdgn vflvpkskkp 601 dvkkn
```

EXAMPLES

Example 1

Creation of NRF2 Knockout Clonal A549 Cell Lines Using a CRISPR-Directed Gene Editing Approach Methods Cell Culture Conditions Human lung carcinoma A549 cells were purchased from ATCC (Manassas, Va., USA). A549 is a well-established non-small cell lung adenocarcinoma cell line, which harbors a mutation in the Kelch domain of KEAP1 causing overexpression of NRF2. It has been used often as a standard for the discovery of novel therapeutic agents directed against cancer. Cells were thawed according to manufacturer's protocol and grown in F-12K medium (ATCC, Manassas, Va., USA) supplemented with 10% FBS (ATCC, Manassas, Va., USA) and 1% Penicillin-Streptomycin Solution (ATCC, Manassas, Va., USA). Cells were cultured and maintained at a concentration between $2 \times 10^3$ and $1 \times 10^4$ viable cells/cm$^2$ and incubated at 37° C. and 5% $CO_2$. Cell number was determined using a hemacytometer.

Guide RNA Design and Construction

The NRF2 gene coding sequence was entered into the Zhang lab's online generator (crispr.mit.edu/), and the gRNA with the highest score was chosen for gRNA1 (5'-UCGAUGUGACCGGGAAUAUCAGG) (SEQ ID NO:2) and a previously validated gRNA targeting NRF2 (Sanjana et al., 2014, Nature Methods 11(8); 783-784) was also chosen for gRNA2 (5'-UGAUUUAGACGGUAUGCAACAGG) (SEQ ID NO:4). The CRISPR-directed gene editing system was designed to disable the NES domain of NRF2, which reduces the capacity of the protein to reenter the nucleus and activate the transcription factor. The CRISPR plasmid was cloned using standard cloning methods with single-step digestion-ligation. The CRISPR guide sequences with appropriate 5' overhangs were cloned into the pX458 backbone vector digested with BbsI (plasmid 48138; Addgene), a human codon optimized pSpCas9 and chimeric guide RNA expression plasmid with a 2AeGFP, purchased through Addgene (addgene.org). The guide RNA sequences were under transcriptional control of the constitutive U6 promoter. See FIG. 1A. Following construction, plasmids were validated by Sanger sequencing (Genewiz Inc., South Plainfield, N.J., USA).

Transfection and Clonal Isolation

A549 cells were transfected at a concentration of $5 \times 10^5$ cells/100 μl in 4 mm gap cuvette (BioExpress, Kaysville, Utah, USA). NRF2 targeting pX458 constructs were separately electroporated (250 V, LV, 13 ms pulse length, 2 pulses, 1 s interval) into A549 cells using a Bio-Rad Gene Pulser XCell Electroporation System (Bio-Rad Laboratories, Hercules, Calif., USA). Cells were then recovered in 6-well plates with complete growth media at 37° C. for 72 hours prior to sorting. A549s were sorted into a 96-well plate with a FACS AriaII flow cytometer (BD Biosciences, Franklin Lakes, N.J., USA), with an individual eGFP+ cell sorted to each well. Clones were expanded and transferred to larger plates as the individual clones reached confluence, with DNA isolation occurring when cells reached confluence in a six-well plate ($1 \times 10^6$ cells/mL).

Sequencing and Sequence Analyses

CRISPR/Cas9 targeted A549 clones were PCR amplified (forward 5'-gtagtggtgccttagagcttactcatcc (SEQ ID NO: 5), reverse 5'-ctagcatgggcagtactcatgactaag (SEQ ID NO: 6)) using Amplitaq Gold Fast PCR Master Mix (Applied Biosystems, Foster City, Calif.). Briefly, template DNA, primers, water and master mix were combined and cycled: 95° C. for 10 minutes, (96° C. for 3 s, 60° C. for 3 s, 68° C. for 5 s) ×35 cycles, and 72° C. for 10 s. The 402 bp products were purified (Qiagen, Hilden, Germany) and Sanger sequenced using the forward PCR primer. Clonal allelic analyses of individual A549 cell clones were analyzed by the software program, Tracking of Indels by DEcomposition (TIDE), to determine the individual sub-sequences within the multi-peaked breakdown product after CRISPR/Cas9 activity. Brinkman, et al., Nucleic Acids Res. 42, e168-(2014). The TIDE analyses provide a visual of the sequence decomposition, the indel patterns of the clone, as well as relative ratios of each clonal indel pattern, serving as an intermediate step in determining each allelic profile. By utilizing the indel patterns and their relative ratios provided by TIDE, the control trace sequence and a clonal trace sequence were manually aligned, allowing for the visualization of the indel patterns of each allele of a clone.

Western Blot Analysis

Total cellular protein was collected from A549 cell lines using a standard RIPA lysis buffer containing a protease inhibitor cocktail. Protein concentrations were determined using a BCA Protein Assay Kit (Pierce, Rockford, Ill., USA). The samples were heated at 95° C. for 10 minutes and then were subjected to SDS-PAGE on a 10% polyacrylamide gel for 90 minutes at 100V. The gel was transferred to a nitrocellulose membrane for 1 hour at 100V. The blot was placed in 3% BSA and blocked overnight on a shaker at 4° C. Primary antibody incubation was performed overnight on a shaker at 4° C. for NRF2 (phospho S40) (1:10,000, Abcam ab76026) and 1 hour at room temperature for beta actin (1:8,000, Abcam ab8226), and secondary antibody (Jackson Immunoresearch, West Grove, Pa., USA) incubations were all done 1 hour at room temperatures, at a 1:10,000 dilution. The protein bands were visualized via chemiluminescence using a Super signal west dura extended duration ECL (Pierce) and detected on the LiCor Odyssey FC. All bands were quantified for densitometry on the Image Studio software system.

Cell Proliferation by FACS Analysis

A549 cell lines were trypsinized and harvested at 50-70% confluency. Cells were fixed with ice cold 70% ethanol dropwise while vortexing and incubated at 4° C. for a minimum of 72 hours. Fixed cells were pelleted and washed twice with PBS followed by a 30-minute incubation on ice. As indicated in the manufacturer's protocol (BD Biosciences), 20 μl per $10^6$ cells of Alexa Fluor 647 Mouse anti-Ki67 (561126, BD Biosciences) was added to the cells and incubated for 30 minutes. Controls included Alexa Fluor 647 Mouse IgG1 k isotype control (557714, BD Biosciences), at the same dilution. After incubation, cells were washed twice and resuspended in stain buffer (5% BSA in 1× PBS). Cells were analyzed with a FACS AriaII flow cytometer and processed using FlowJo software.

Results

Figure 1A:
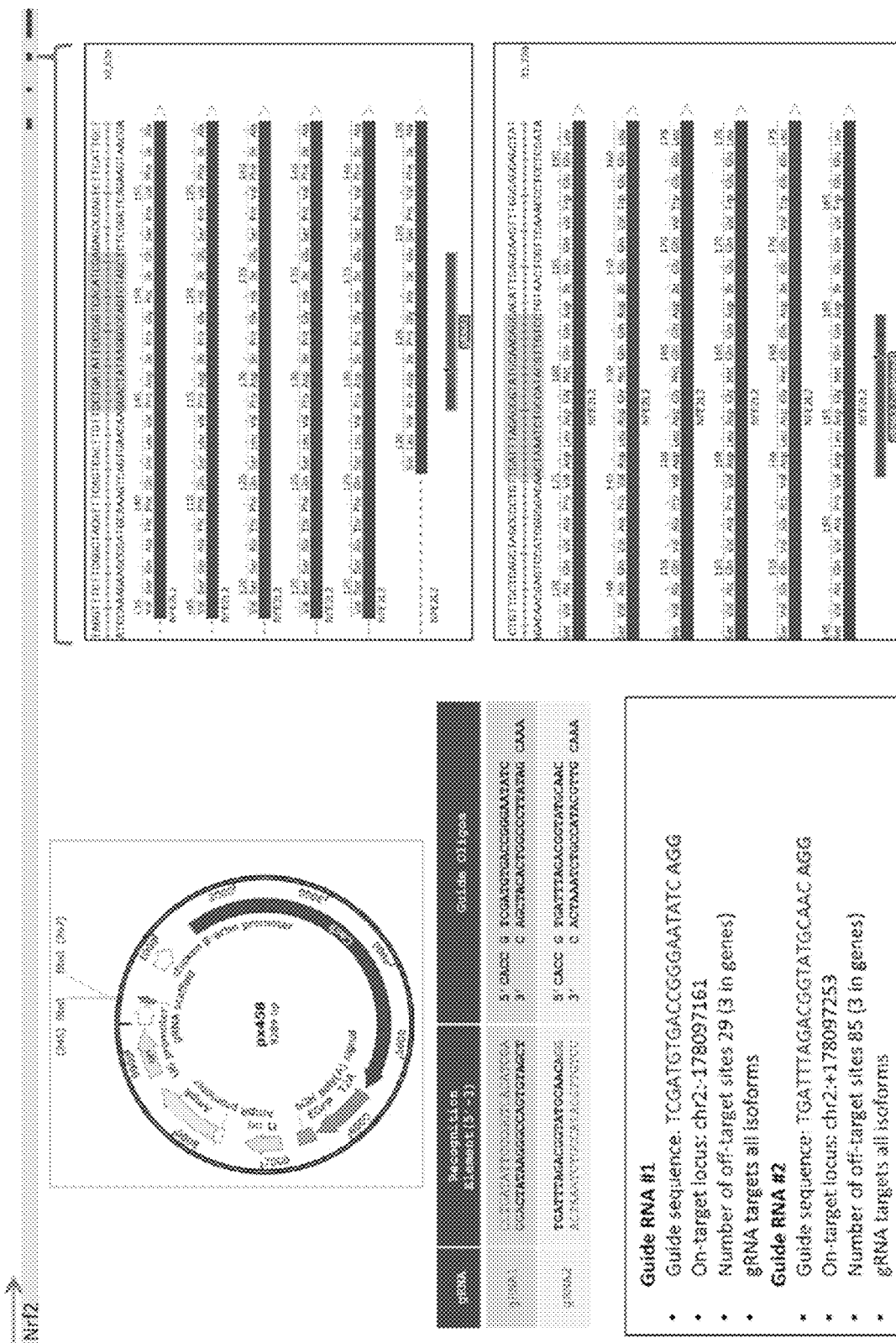
FIGS. 1A, 1B and 1C show CRISPR design and NRF2 knockout experimental workflow. NRF2 coding regions containing the six known genetic isoforms (SEQ ID NOs: 68-73 for qRNA1 and SEQ ID NOs: 74-79 for qRNA2) were utilized for targeting by CRISPR/Cas9. The gRNA sequences (SEQ ID NOs: 9 and 10), along with their chromosomal loci and cloning details are displayed (A). The structural domains and location of CRISPR-directed gene editing of the NRF2 protein (B). The experimental workflow for testing the efficiency of CRISPR/Cas9 knockout of NRF2 in a targeted population and in isolated and expanded clonal cell lines (C).

The strategy was to use CRISPR-directed gene editing to functionally disable NRF2 alleles in A549 lung carcinoma cells. It is critical to establish the fact that a gene editing technology can knockout a target gene. Below are provided the strategy details which were utilized to generate the genetic tools used to disable NRF2 in A549 cells. FIG. 1A illustrates the CRISPR/Cas9 machinery designed to target and knockout NRF2. The grey bar running along the top of the panels represents the genomic sequence of NRF2, with the red blocks indicating coding regions. The blue brackets indicate the relative region where each CRISPR/Cas9 is designed to cleave the DNA. Each gRNA was designed to target the fourth exon of NRF2 in a region that contains all known isoforms to ensure complete ablation of the gene (ncbi.nlm.nih.gov/gene/4780). The gRNA with the highest score, according to the Broad Institute's CRISPR Design software (crispr.mit.edu/), was chosen for gRNA1 and a previously validated gRNA (Sanjana et al., bioRxiv 006726 (2014). doi:10.1101/006726) was chosen for gRNA2. The gRNAs were assembled by annealing the crRNA oligos and ligating them to complementary restriction site overhangs in plasmid px458 (Addgene #48138) digested with BbsI, as depicted in each panel.

Figure 1B:
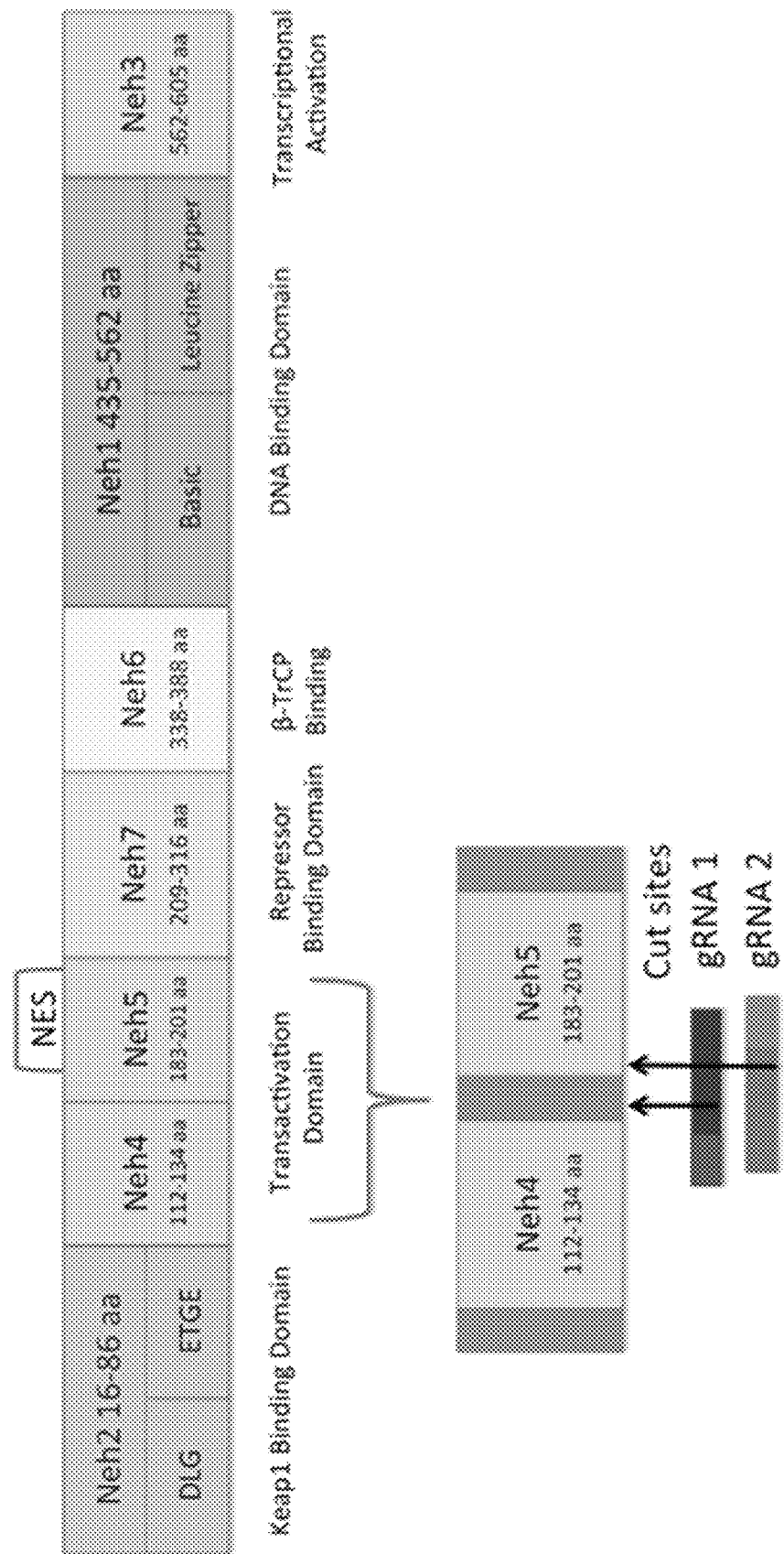
Figure 1C:
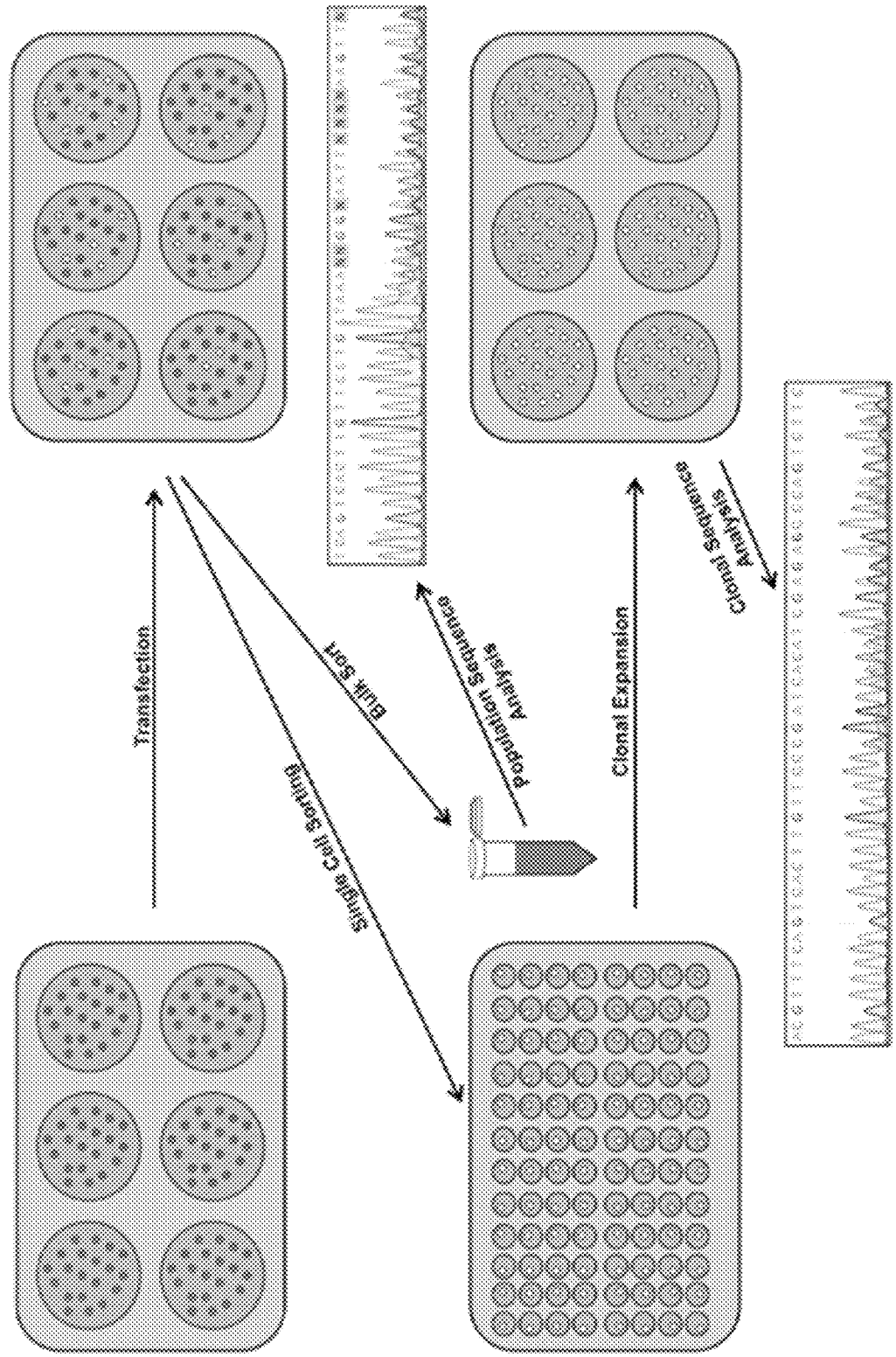
Figure 2A:
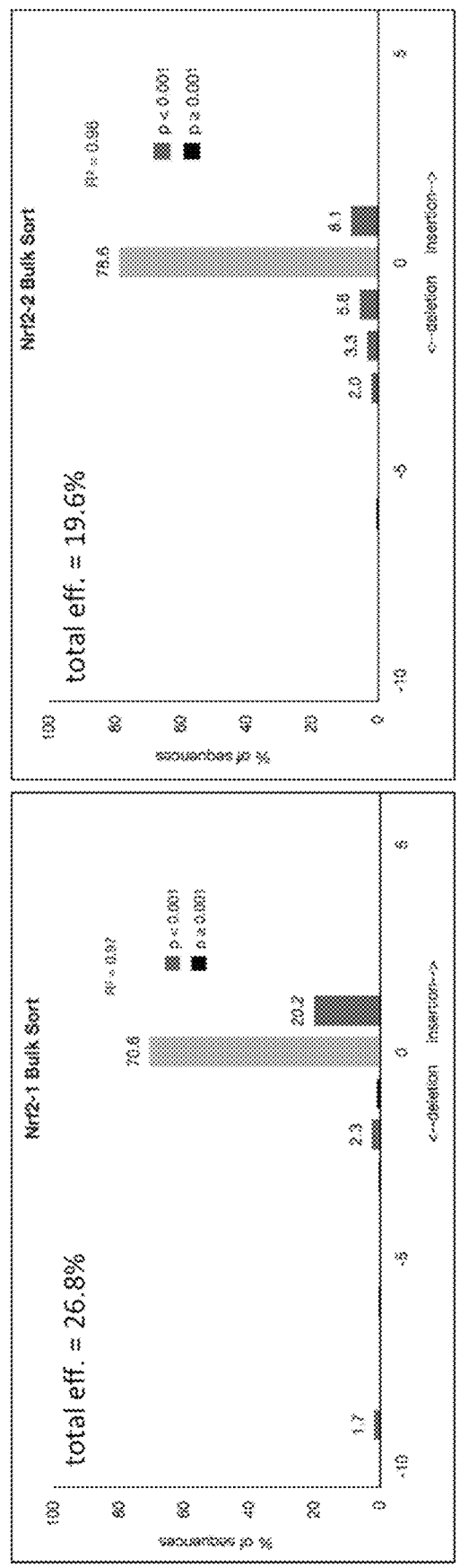
FIGS. 2A and 2B show genomic analyses of NRF2 knockout clones. Bulk sorted GFP+A549 cells transfected with either gRNA1 or gRNA2 were Sanger sequenced and analyzed for indel activity by TIDE (A). Clonally isolated NRF2 targeted cells were genomically analyzed for CRISPR/Cas9 induced NHEJ activity. Genomic DNA was Sanger sequenced and TIDE was used to develop the indel spectrums, sequence decompositions and allelic patterns of NRF2 as shown for clones 1-40 and 2-11 (B). SEQ ID NO:80 (NRF2 WT clone 1-40), SEQ ID NO:81 (allele 1 clone 1-40), SEQ ID NO:82 (allele 2 clone 1-40), SEQ ID NO:83 (allele 3 clone 1-40), SEQ ID NO:84 (NRF2 WT clone 2-11), SEQ ID NO:85 (allele 1 clone 2-11), SEQ ID NO:86 (allele 2 clone 2-11), SEQ ID NO:87 (allele 3 clone 2-11)

FIG. 1B illustrates the functional domains of the NRF2 protein including the KEAP1 Binding Domain, Transactivation Domain, Repressor Binding Domain, β-TrCP Binding Domain, DNA Binding Domain and the Transcriptional Activation Domain. Pandey et al., Crit. Rev. Oncol. Hematol. 116, 89-98 (2017); Jung et al., Molecular Mechanisms to Therapeutic Opportunities. 26, 57-68 (2018); Namani et al., Biochim. Biophys. Acta-Mol. Cell Res. 1843, 1875-1885 (2014). The Neh5 domain spans Exon 4 and 5 and contains a redox-sensitive nuclear-export signal (NES), which regulates the intracellular localization of NRF2. Jung et al., Molecular Mechanisms to Therapeutic Opportunities. 26, 57-68 (2018). In theory, by disrupting the gene/protein within the Neh4 and Neh5 domain, the NES is shifted, rendering it nonfunctional. FIG. 1C exhibits the experimental workflow beginning with the transfection of pX458 containing either gRNA1 or gRNA2 into A549 lung adenocarcinoma cells progressing through to the final step of allelic analyses of an individual clonal population. Importantly, plasmid pX458 contains an eGFP reporter, which allows for isolation of individual transfected cells by FACS. To evaluate the efficiency of CRISPR-directed NRF2 knockout in the total targeted population, eGFP+ cells were isolated as a population, and the degree of genetic disruption at the NRF2 locus in cells, transfected with either gRNA1 or gRNA2 pX458, was determined. The sorted populations were Sanger-sequenced and the resulting trace files were analyzed for the presence of indels, a marker for gene disruption. These data were obtained using a program known as Tracking of Indels by Decomposition (TIDE). Brinkman, et al., Nucleic Acids Res. 42, e168-(2014). As represented in FIG. 2A, both CRISPR/Cas9 designs generated a significant amount of indels, evidenced by TIDE results, indicating a high degree of NRF2 disruption. These results validate the approach and indicate that disruption of the NRF2 is possible in A549 cells via CRISPR/Cas9.

Figure 2B:
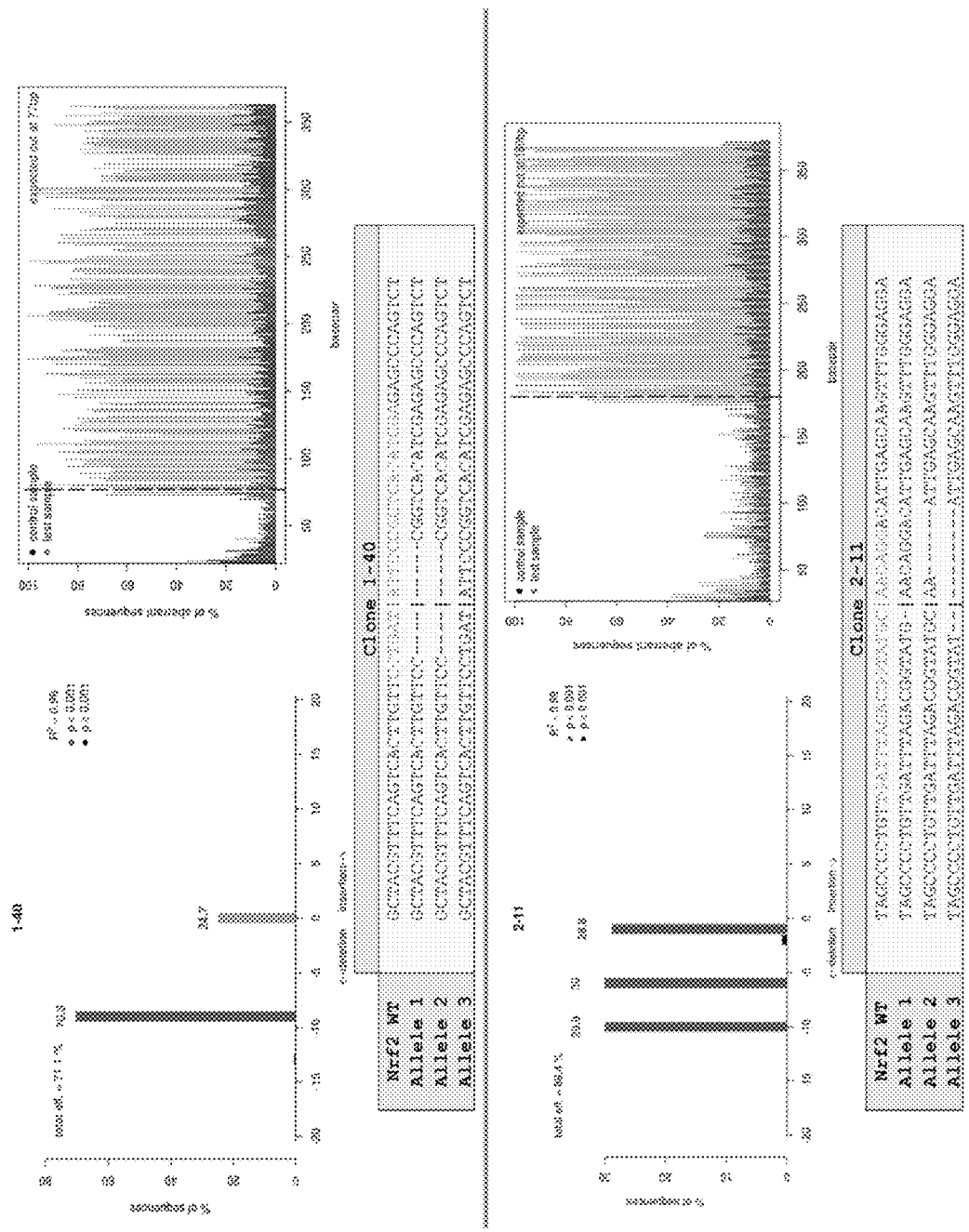

Next, the same experiment was carried out except in this case, individual cells were isolated by FACS sorting to obtain single cell clonal expansions. When the single cell isolates had expanded to sufficient quantity, half of each clonal population was cryo-preserved and allelic sequence analysis was performed on the other half using the same strategy and method described above. FIG. 2B displays the allelic analyses of two clones, 1-40 and 2-11, derived from gRNA1 and gRNA2 transfected cells respectively, which were chosen from a total of nine (Figure Supplement 1) for subsequent experimentation and analyses. It soon became apparent that all isolated clones generated from this parental lot of A549 cells obtained from ATCC harbored three alleles at the NRF2 locus. The red columns indicate the indel sizes present and their respective representative ratios within that clone. Clone 1-40 contains a 9 bp deletion with a 2:1 ratio to 0 bp indels, revealing a heterozygous KO of NRF2. Clone 2-11 contains a 10 bp deletion, a 6 bp deletion and a 1 bp deletion at a 1:1:1 ratio, a homozygous KO of NRF2. The specific indel patterns on each allele of both clones were characterized by manually aligning the sequence trace files to the wild-type sequence, with the TIDE indel data as a guide. For convenience, we refer to clone 1-40 as a heterozygous knockout and clone 2-11 as a homozygous knockout.

Figure 3A:
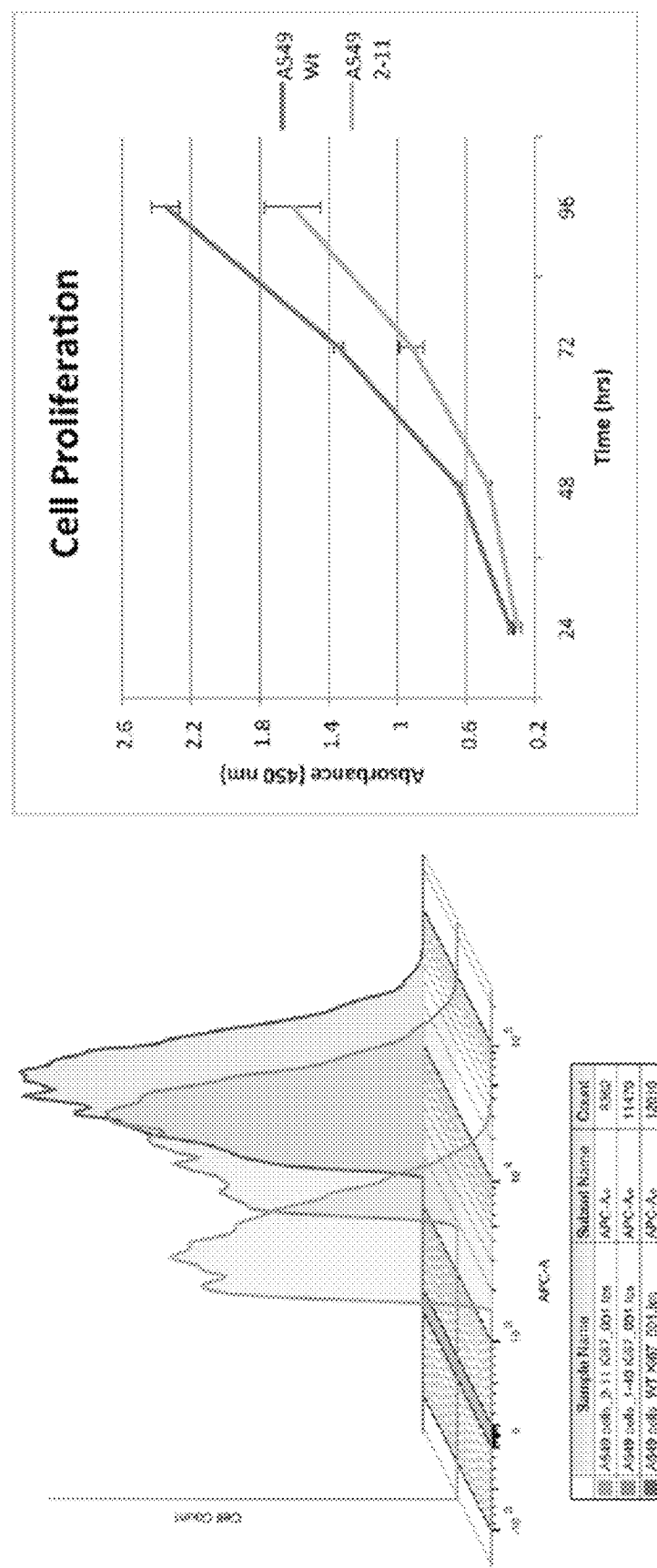
FIGS. 3A and 3B show the cellular proliferation profile of NRF2 knockout A549 cells and western blot analysis. Cells were fixed with ethanol for 72 hours and stained with Alexa Fluor 647 Anti-Ki67. Fluorescence-activated cell sorting (FACS) was used to capture the intensity of Ki67-stained cells and plotted as a histogram using FlowJo software (left panel) (A). Cell proliferation was measured via bioreduction of MTS to a formazan product, plotted as mean raw absorbance values (right panel) and error bars represent±SEM (A). Western blot analysis of wild type A549 cells and NRF2 knockout 2-11 cells using an antibody for phosphorylated NRF2 (B).

A fundamental cellular phenotype that could be affected by the lack of an NES is the rate at which cells proliferate in culture. Murakami et al., Free Radic. Biol. Med. 88, 168-178 (2015); Mitsuishi et al., Cancer Cell 22, 66-79 (2012). Wildtype A549 cells typically have a doubling time of 24 hours, however, it was noted that clones 1-40, but more clearly, 2-11, grew slower in the clonal expansion process (data not shown). This observation prompted us to further investigate the proliferation profile of clones 1-40 and 2-11 by staining the cells with antibodies against Ki67, followed by FACS analysis. Ki67 is a nuclear antigen expressed in actively proliferating cells. Therefore, one might predict a decrease in Ki67 expression based on the growth characteristics seen in cell culture. Ethanol-fixed cells were stained with Alexa Fluor 647 Anti-Ki67, analyzed by FACS and plotted as a histogram (Left panel, FIG. 3A). Nonspecific binding was controlled for using the mouse IgG1 κ isotype control provided and gated on FlowJo. The x-axis represents fluorescence intensity of the allophycocyanin (APC)—conjugated Anti-Ki67, of which a shift to the left can be seen in clone 2-11, indicating a decrease in fluorescence intensity, correlating to a decrease in cellular proliferation.

Figure 3B:
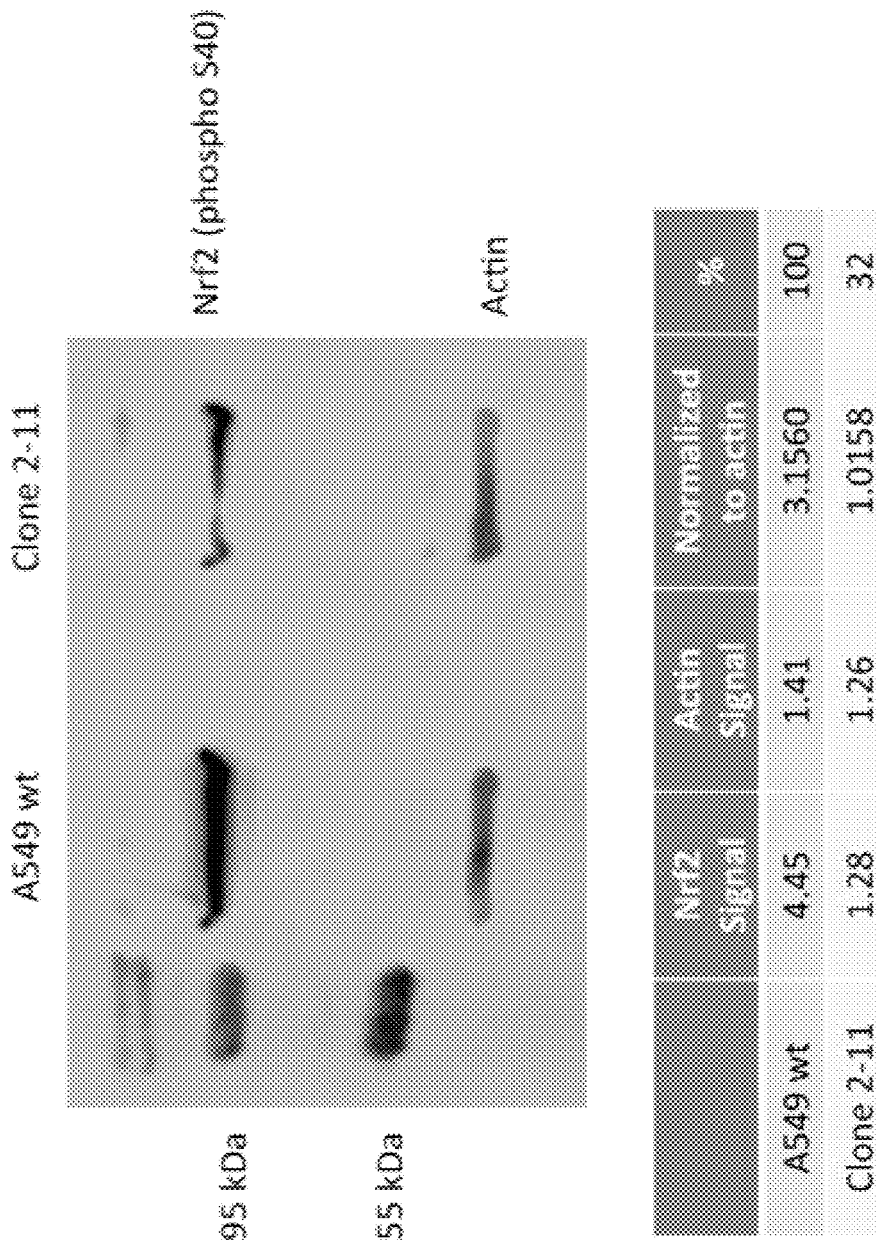

The decrease in proliferation in 2-11 cells was striking while the reduction in proliferation in 1-40 cells was modest at best. Thus, we decided to continue our studies on the effect of NRF2 knockout using 2-11 cells only because CRISPR-directed gene editing succeeded in disrupting function more completely in those cells. Based on growth characteristics in cell culture and the FACS analysis, the MTS assay was utilized to assess the proliferation of 2-11 cells compared to wildtype cells (Right Panel, FIG. 3A). Allelic analysis of clone 2-11 indicated that NRF2 is genetically disabled and when normalized to beta-actin and compared to wildtype A549 cells, clone 2-11 showed a knockdown of ~68% (FIG. 3B). Since one of the three alleles in clone 2-11 maintains a functional reading frame, this result is not unexpected. Genetic analysis indicated that the Neh5 domain, which contains the NES, was disrupted. Thus, we moved forward to characterize this clone identifying it as a functional knockout.

Example 2

Chemosensitivity is Increased in NRF2 Knockout A549 Cell Lines

Methods
MTS Cell Proliferation Assay

Cell viability was evaluated using the CellTiter 96 Aqueous Non-Radioactive Cell Proliferation Assay (Promega, Madison, Wis.). A549 cell lines were plated at $2\times10^3$ cells per well and allowed to culture for 24 hours. The cell media was then aspirated, the cells washed with PBS, then exposed to the MTS reagent for 3 hours. After 3 hours of MTS bio-reduction by proliferating cells, the formazan product's absorbance was measured using a 450 nm filter on an Infinite 2000 PRO microplate reader (Tecan, Mannadorf, Switzerland). Cell viability after drug exposure was evaluated using the CellTiter 96 Aqueous Non-Radioactive Cell Proliferation Assay. A549 cell lines were plated at $2\times10^3$ cells per well and allowed to culture for 24 hours. The cells were then treated with cisplatin, carboplatin, or a combination of cisplatin and vinorelbine for three days. The cell media was then aspirated, the cells washed with PBS, then exposed to the MTS reagent for 3 hours. After 3 hours of MTS bio-reduction by proliferating cells, the formazan product's absorbance was measured using a 450 nm filter on an Infinite 2000 PRO microplate reader.

Results

Figure 4A:
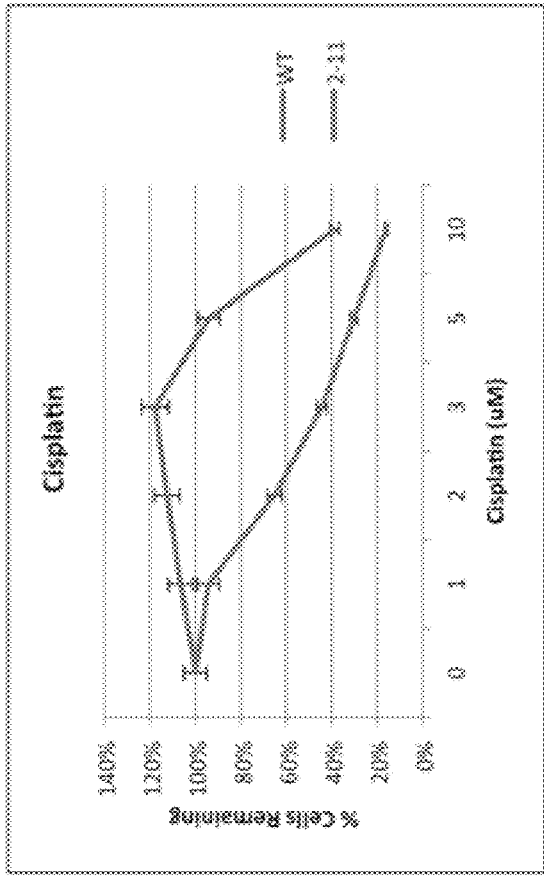
FIGS. 4A and 4B show the proliferation capacity of wild type and NRF2 modified A549 cells (2-11) in response chemotherapeutic drugs. Proliferation was measured via bioreduction of MTS to a formazan product. Cells were treated with increasing dosages of cisplatin (A) and increasing dosages of cisplatin with 5 µM vinorelbine (B) for 72 hours, then evaluated for cell proliferation. Error bars represent±SEM.
Figure 4B:
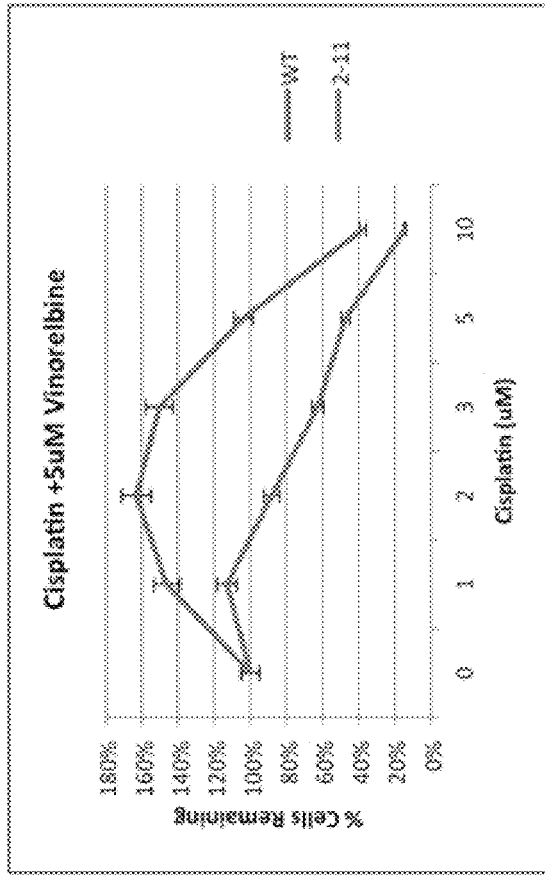

To examine the chemosensitivity of the genetically engineered NRF2-deficient A549 cell lines, the MTS assay, depicted in FIG. 4, was utilized. In 4A, wild type and 2-11 A549 cells were exposed to increasing dosages of cisplatin.

After 72 hours, cisplatin was removed, and the MTS reagent was added for three hours after which time the population was measured for the absorbance of formazan. The data show that, as predicted, wild type A549 cells are resistant to high dosages of Cisplatin. In fact, wild type A549s display a slight increase in cell proliferation up to 3 µM of cisplatin before proliferation is adversely affected at final concentrations of 5 µM and 10 µM, respectively. In the genetically engineered knockout cell lines, we clearly observe an increase in chemosensitivity in a dose-dependent fashion. The 2-11 homozygous knockout cells display a heightened sensitivity, evident even at the lowest dose with a loss of proliferation at concentrations at and above 1 µM. Thus, it is possible that we are observing a gene dosage effect of sorts in that the heterozygous cell line exhibits more resistance to cisplatin than homozygous knockout cells because it contains at least one viable gene copy. In FIG. 4, we display a result from cells being exposed to the same increasing amount of cisplatin as described for Panel A, except Vinorelbine was added to a final concentration of 5 µM. Vinorelbine is an established companion to cisplatin and combinatorial chemotherapeutic regimens NSCLC. Hellmann, et al., Ann. Oncol. Off. J. Eur. Soc. Med. Oncol. 27, 1829-35 (2016). The wild type A549 cells again displayed a dramatic increase in proliferation even at lower doses and did not show elevated sensitivity until the dosage surpassed 5 µM, but the knockout cell line (2-11) displayed increased sensitivity to the combinatorial drug therapy. Carboplatin, a related anticancer drug and commonly used chemotherapy for NSCLC (Hellmann et al., ibid) was also evaluated for enhanced chemosensitivity in these genetically engineered A549 cells and the cell killing response reflected what was observed in the experiments using cisplatin (data not shown).

Example 3

Genetically Reengineered A549 Cells Showed Slower Growth Rate and Increased Chemosensitivity in a Xenograft Mouse Model of Lung Cancer Methods
Animal Experiments and Statistical Analysis
The animal trials presented herein were carried out at Washington Biotech Inc., Simpsonville Md., under animal use and care protocol (SOP 505, SOP 520, SOP 522, SOP 1610, SOP1650) approved by the animal care and use committee of Washington Biotechnology Inc. (AAALAC accredited Animal Welfare Assurance number A4192-01). The human xenograft model was established using methodology reported previously. Kellar et al., Biomed Res. Int. 2015, 1-17 (2015). Female athymic nude mice (Envigo, 5-6 weeks old) were used in this study. Approximately $5 \times 10^6$ cells (wild type A549 or homozygous knockout (clonal expansion 2-11)) suspended in PBS with 20% Matrigel were injected subcutaneously into right flank of each mouse. Tumor volume was measured three times a week with a digital caliper once palpable, and calculated using the formula, tumor size=$ab^2/2$, where 'a' is the larger and 'b' is the smaller of the two dimensions. When tumors grew up to a mean volume of around 100 mm$^3$, A549 tumor bearing mice or A549-2-11 tumor bearing mice were randomly divided into 7 groups (N=5 for each group) respectively and subject to dose/regimen-finding study. They were treated with tail vein injection of (1) Cisplatin (2 mg/kg), (2) Carboplatin (25 mg/kg), (3) Cisplatin (5 mg/kg) and Vinorelbine (5 mg/kg) or (4) saline on day 0, 3, 6 and 9 (day 0 is designated as the day of dose started) (Sanjana et al., 2014, Nature Methods 11(8); 783-784). Tumor volume and body weight was closely monitored over time. After 16 days, the animals were sacrificed, with tumor removed, weighed and processed for molecular analysis. Mice were euthanized. The data were expressed as mean±SD. Student's t-test and one-way or two-way ANOVA was used to assess the significance of difference. A P value<0.05 was considered significant.

Immunofluorescence Staining
A549 xenografts were resected on day 16, snap frozen in liquid nitrogen and stored in −80° C. until usage. All immunofluorescence staining was performed as previously described. Wang et al., Investig. Opthalmology Vis. Sci. 58, 3896 (2017). Briefly, tumors were embedded in Optimum Cutting Temperature (Tissue Tek, Torrance, Calif., USA) and 16-µm-thick sections were obtained with a Leica CM3050 cryostat (Leica Microsystems, Buffalo Grove, Ill., USA), and mounted on slides. Slides were fixed and incubated with blocking buffer for 1 hour at room temperature. Sections were then incubated with primary antibody (refer to Table 3 for more details), then washed in PBS and incubated with Alexa Fluor 488 labeled secondary antibody (1:200 dilution; Invitrogen, Grand Island, N.Y., USA) for 1 hour at RT. Sections were washed in PBS, then mounted with SlowFade Gold antifade mountant with DAPI (Invitrogen, Carlsbad, Calif., USA). Images were obtained with a Zeiss Observer.Z1 microscope (Carl Zeiss, Inc., Gottingen, Germany). The TUNEL assay was conducted with In Situ Cell Death Detection Kit, Fluorescein (Roche, Base, Switzerland), following the manufacturer's instructions.

TABLE 3

| Primary antibody | Fixation | Blocking buffer | Dilution buffer | Incubation condition and dilution rate |
| --- | --- | --- | --- | --- |
| Ki67 (9129, Cell Signaling) | 4% PFA for 30 min at room temperature | 5% goat serum, 0.3% Triton X-100 in PBS | 2% BSA, 0.3% Triton X-100 in PBS | Overnight at 4° C., 1:100 |

Immunocytochemistry and Image Quantification

A549 cell lines were seeded in 8-well chamber slides (LabTek II) and allowed to grow for 24 hours. After exposure to 2 μM of cisplatin for 48 hours, cells were washed with PBS, fixed and permeabilized with 4% paraformaldehyde+0.1% Triton X-100 for 45 minutes, while shaking at room temperature. Cells were washed three times with PBS and blocked with a blocking buffer solution (5% normal goat serum+0.3% Triton X-100 made in 1× PBS) for 2 hours at room temperature. Following blocking, cells were incubated with primary antibody (NRF2 1:500, Abcam ab62352) made in an antibody dilution buffer (1% BSA+0.3% Triton X-100 made in 1× PBS), overnight in a humidified chamber at 4° C. Cells were washed three times with PBS and incubated with a conjugated secondary antibody (goat anti-rabbit Alexafluor 594, Thermo Fisher A-11037) made in an antibody dilution buffer at a concentration of 1:200. Controls included secondary only antibody stains, at the same dilutions. Cells were incubated for one hour at room temperature, in the dark. Cells were washed three times with PBS and the chamber was separated from the glass slide. Immediately following this step, 50 of Slow Fade Gold antifade reagent with DAPI (S36938, Invitrogen) was added to each section of the slide and a coverslip was added and sealed. Slides were imaged on the Zeiss Axio fluorescent observer. Z1 microscope and images were processed on the AxioVision software. Random fields were imaged and the total number of cells/field was counted. Each field was quantified for no staining (none), nuclear staining, or cytoplasmic staining. Two individuals independently counted and quantified the images and values were averaged. The percent of NRF2 positive stained cells over the total cells analyzed in each category was plotted in the graph. Errors bars represent ±SEM and * denotes a significant p value that is <0.05 (Student's T-test).

Results

Figure 5A:
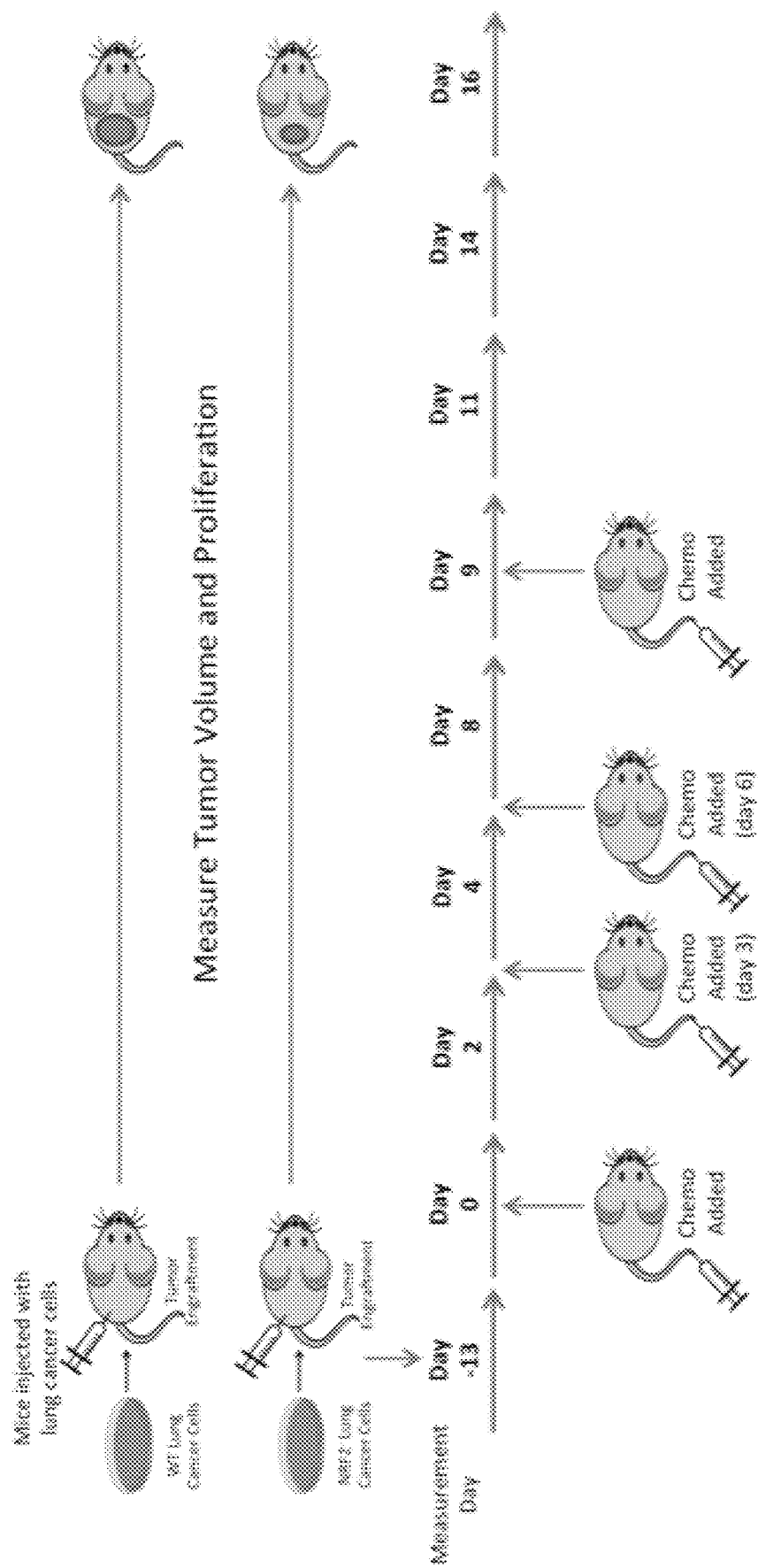
FIGS. 5A, 5B, 5C, 5D and 5E show restored chemosensitivity in mice with NRF2 knockout in tumors. Experimental workflow of mouse xenograft. Athymic nude mice were subcutaneously injected with either wild type A549 cells or NRF2 knockout A549 cells and once established tumors reach 100 mm$^3$ were treated with the first dose of chemotherapy on Day 0. Mice were subsequently treated with chemo on days 3, 6, 9. Tumor volumes were measured daily for 16 days until tumors reached 2000 mm$^3$ (A). Wild type A549 or NRF2 Knockout A549 tumors were treated with either 2 mg/kg of cisplatin (B), 5 mg/kg of cisplatin with 5 mg/kg of vinorelbine (C), 25 mg/kg of carboplatin (D), or saline and tumor size was measured for 16 days. Error bars represent±SEM. Tumors (treated with 2 mg/kg of cisplatin or saline) were extracted from both the wild type A549 and NRF2 knockout A549 (2-11) implanted mice. Representative tumors from each group are shown (n=3) (E).

Since CRISPR/Cas9-mediated NRF2 knockdown increased chemosensitivity in A549 cells in vitro, we examine enhanced chemosensitivity driven by gene editing in a xenograft mouse model. The homozygous knockout A549 cells (clone 2-11) and wild type A549 cells (control group) were implanted into the back of a nude mouse and the cells ($5\times10^6$ per cell line) were allowed to proliferate into a tumor with a diameter of approximately 100 mm$^3$. The workflow is depicted in FIG. 5A. As part of the strategy, the chemotherapeutic agent was added at day 0, day 3, day 6 and day 9, respectively, through tail vein injection as indicated in the diagram. Tumor growth through volume and proliferation were measured over the course of 16 days starting at the time of the first injection of the chemotherapeutic agent, day 0, and the results are presented in FIGS. 5B, 5C and 5D.

Figure 5B:
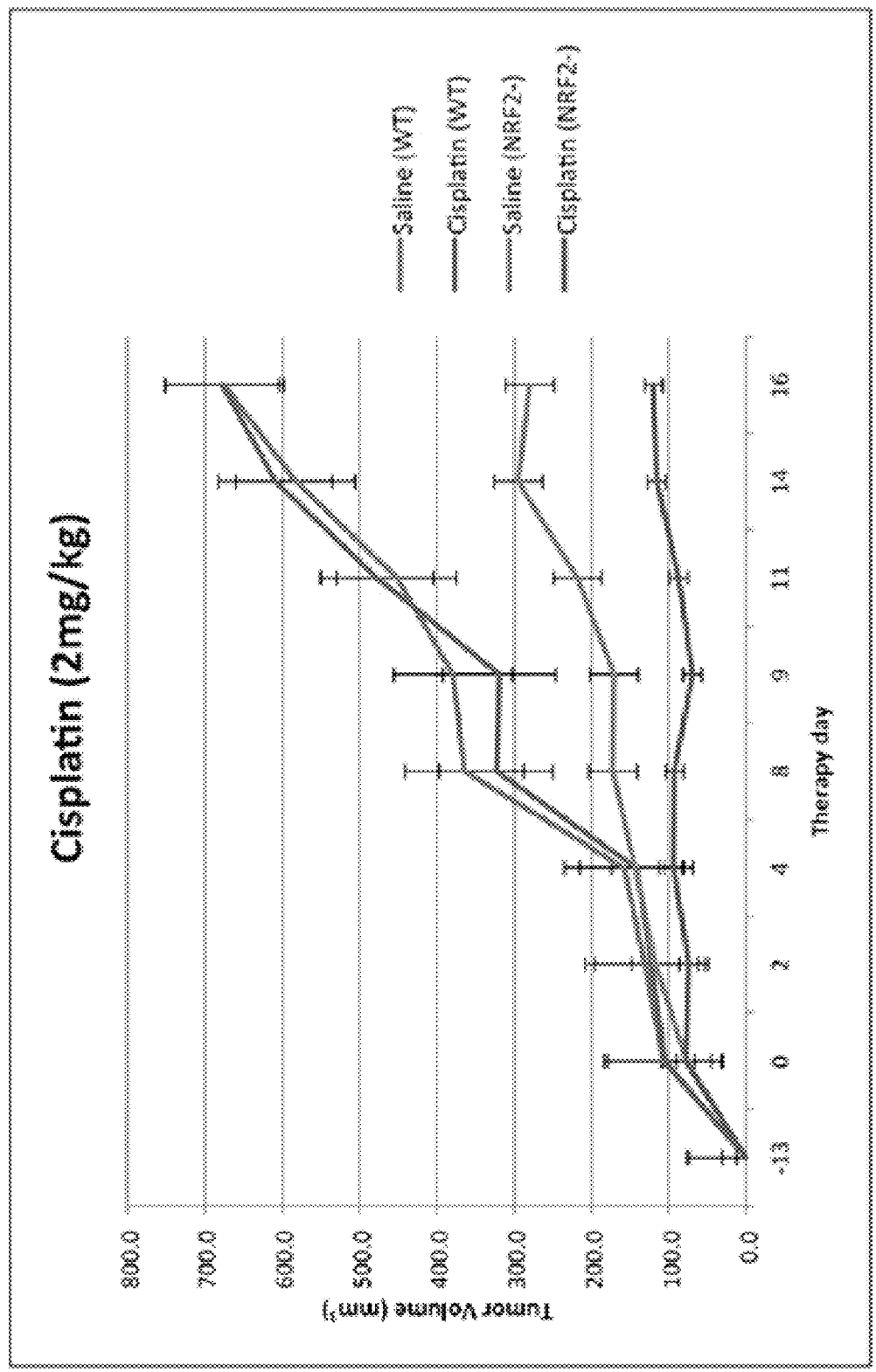

FIG. 5B depicts the results of tumor growth over the course of 16 days. As expected, proliferation of wild type A549 cells, treated with either saline or 2 mg/kg of Cisplatin, was not inhibited by the drug, confirming the well-established resistance of A549 cells to cisplatin. The NRF2 knockout xenograft proliferated in the mouse but at a reduced rate even without the addition of Cisplatin. The most dramatic effect is seen when a combinatorial approach is taken wherein NRF2 knockout cells are treated with cisplatin over a period of 16 days. In this case, proliferation of the implanted cells is arrested, and the tumor size is maintained at the same level throughout the course of the experiment, which confirms our previous results generated from experiments conducted in cell culture (FIG. 4).

Figure 5C:
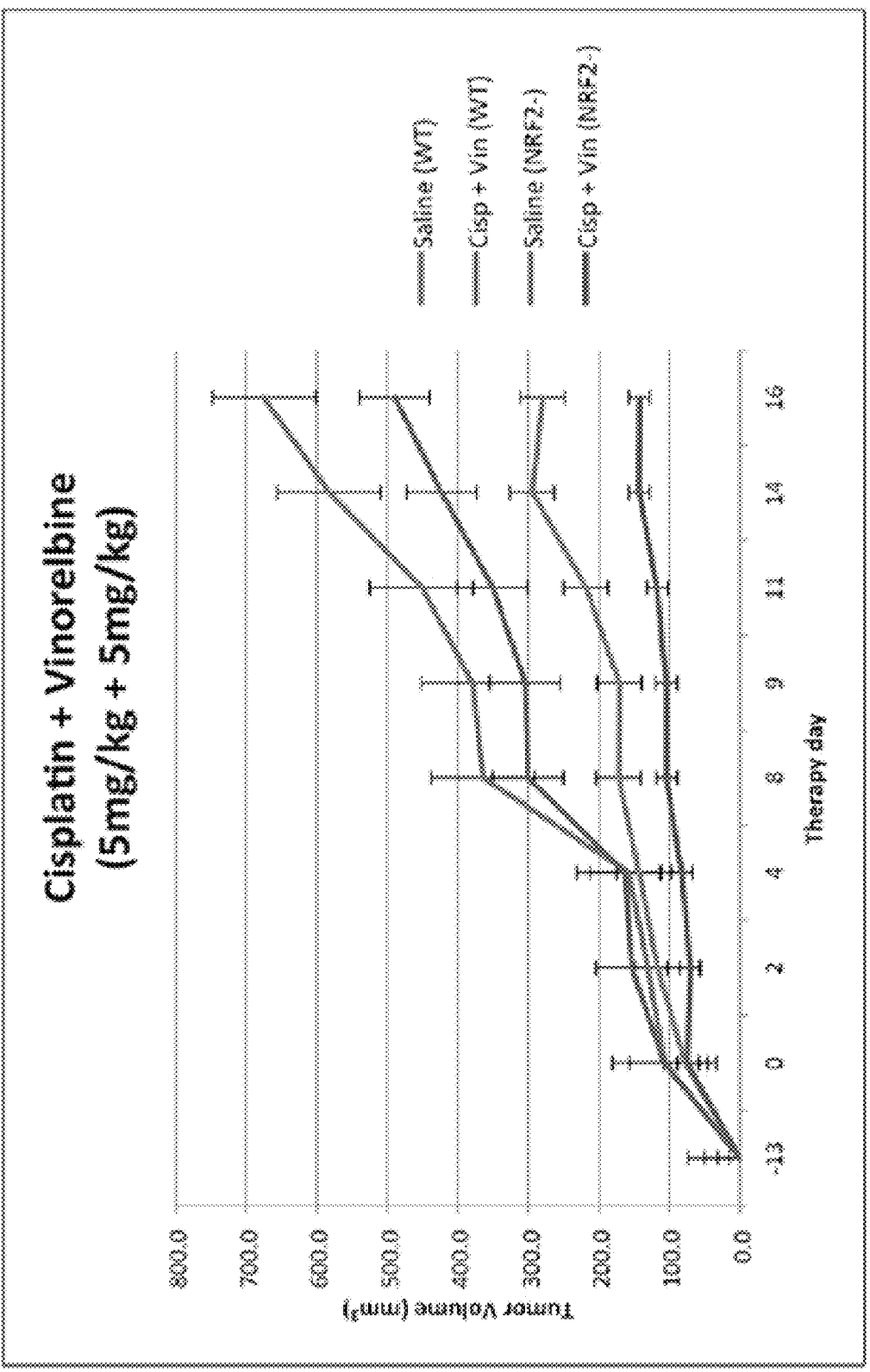
Figure 5D:
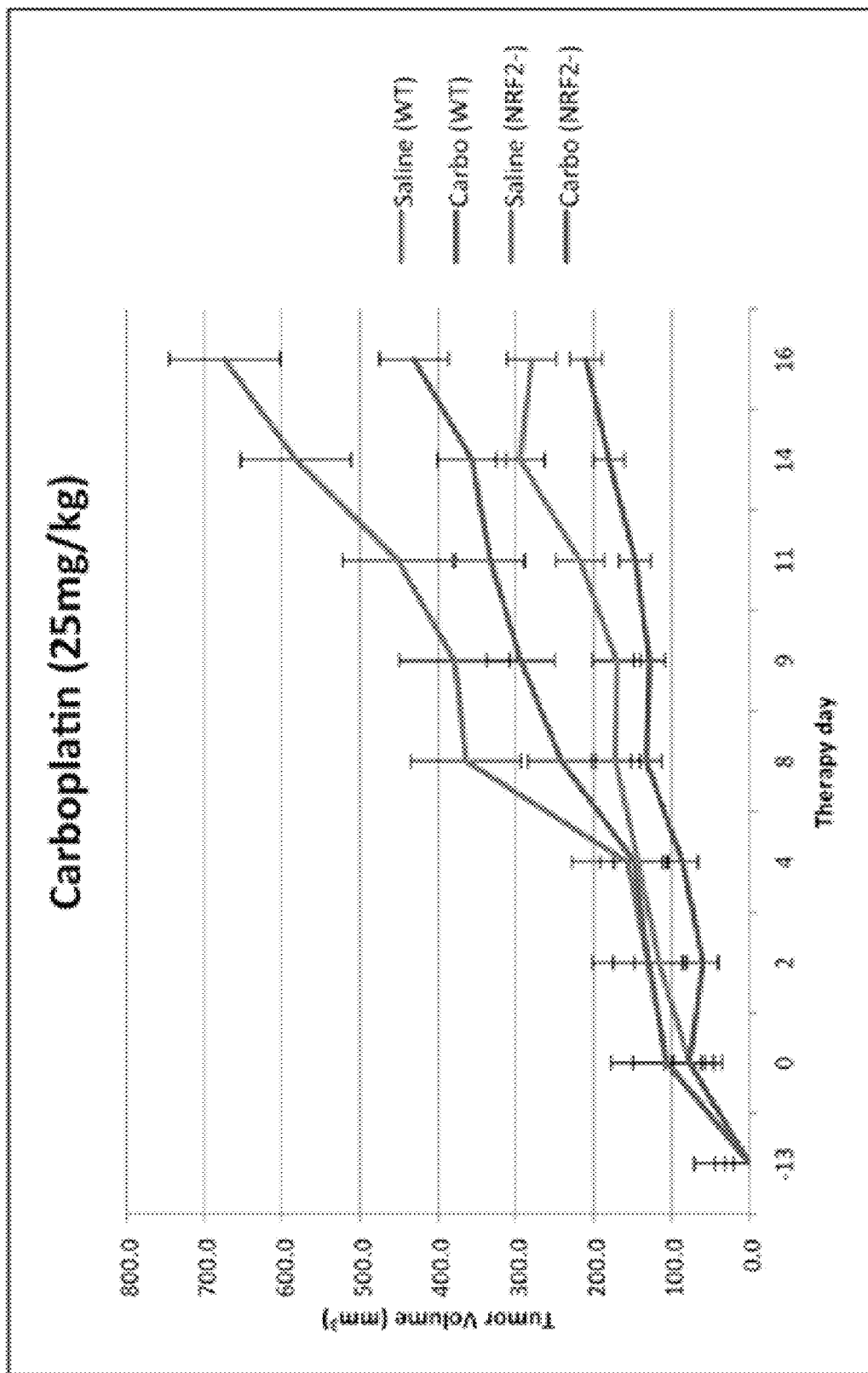

FIG. 5C depicts similar results when fixed concentrations of 5 mg/kg cisplatin and 5 mg/kg vinorelbine are used in combination following the same xenograft mouse experimental protocol. Interestingly, the wild type A549 cells appear to be more sensitive to this combination of drugs. This observation may reflect the synergistic effect that Vinorelbine has on Cisplatin killing of A549 cells, providing an important internal control that our experimental system recapitulates previously known outcomes. Once again, the homozygous knockout 2-11 cell line proliferates at a slower rate than the wild type cells in the absence of drug treatment, but the combination of NRF2 knockout and drug treatment leads to a cessation of tumor growth and maintenance of tumor size over the course of 16 days. The same response is seen once again in the data presented in FIG. 5D wherein 25 mg/kg carboplatin is injected in the tail vein; the same reduced proliferation and growth trend described above is reproduced. These results suggest that the combination of gene editing in chemotherapy produces an enhanced chemosensitivity in A549 cells both in cell culture and in a Xenograft mouse model.

Analyses of A549 Tumor Proliferation

Figure 5E:
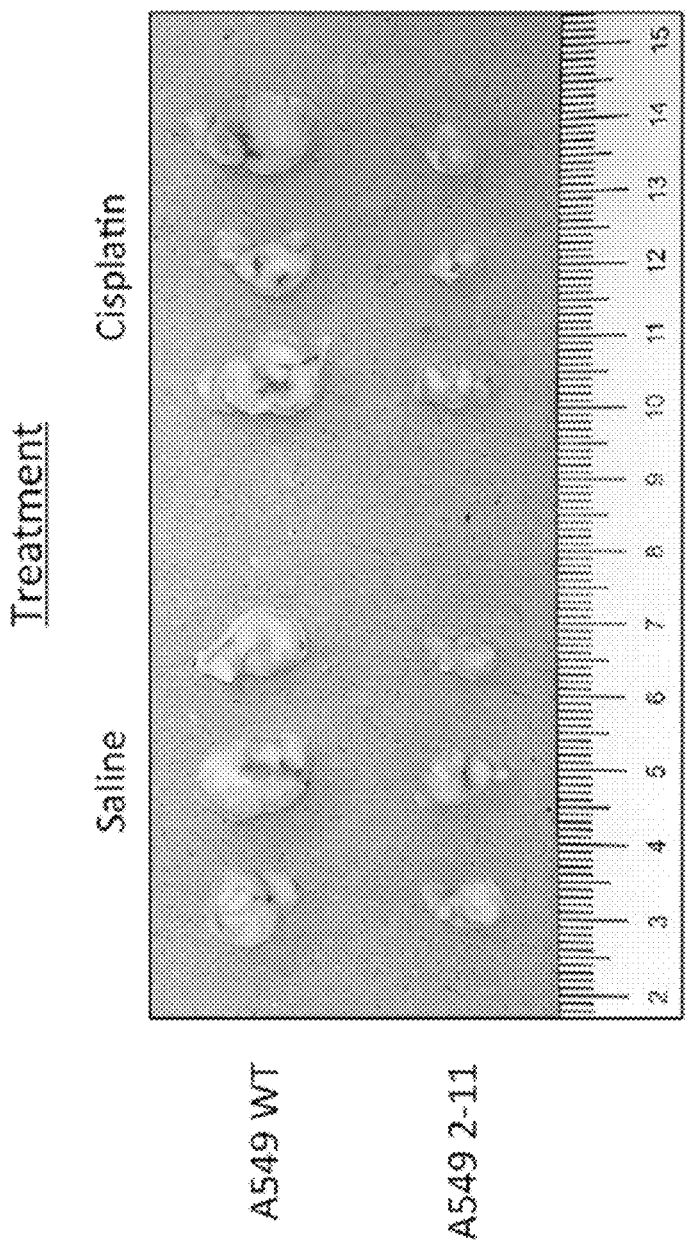

Representative tumor samples were harvested from four groups (wild type A549 with saline, wild type A549 with cisplatin 2 mg/kg, knockout 2-11 with saline, knockout 2-11 with cisplatin 2 mg/kg) (N=3 for each group). As shown in FIG. 5E, a distinct difference among the four extracted tumor groups is apparent. As described above, tumors generated from wild type cells proliferate aggressively within the xenograft mouse model in the absence or presence of cisplatin. The NRF2 knockout cell line proliferates more slowly than the wild type even in the absence of the drug. But, the smallest tumors are observed in all the samples from mice bearing NRF2 knockout cells treated with cisplatin.

Figure 6:
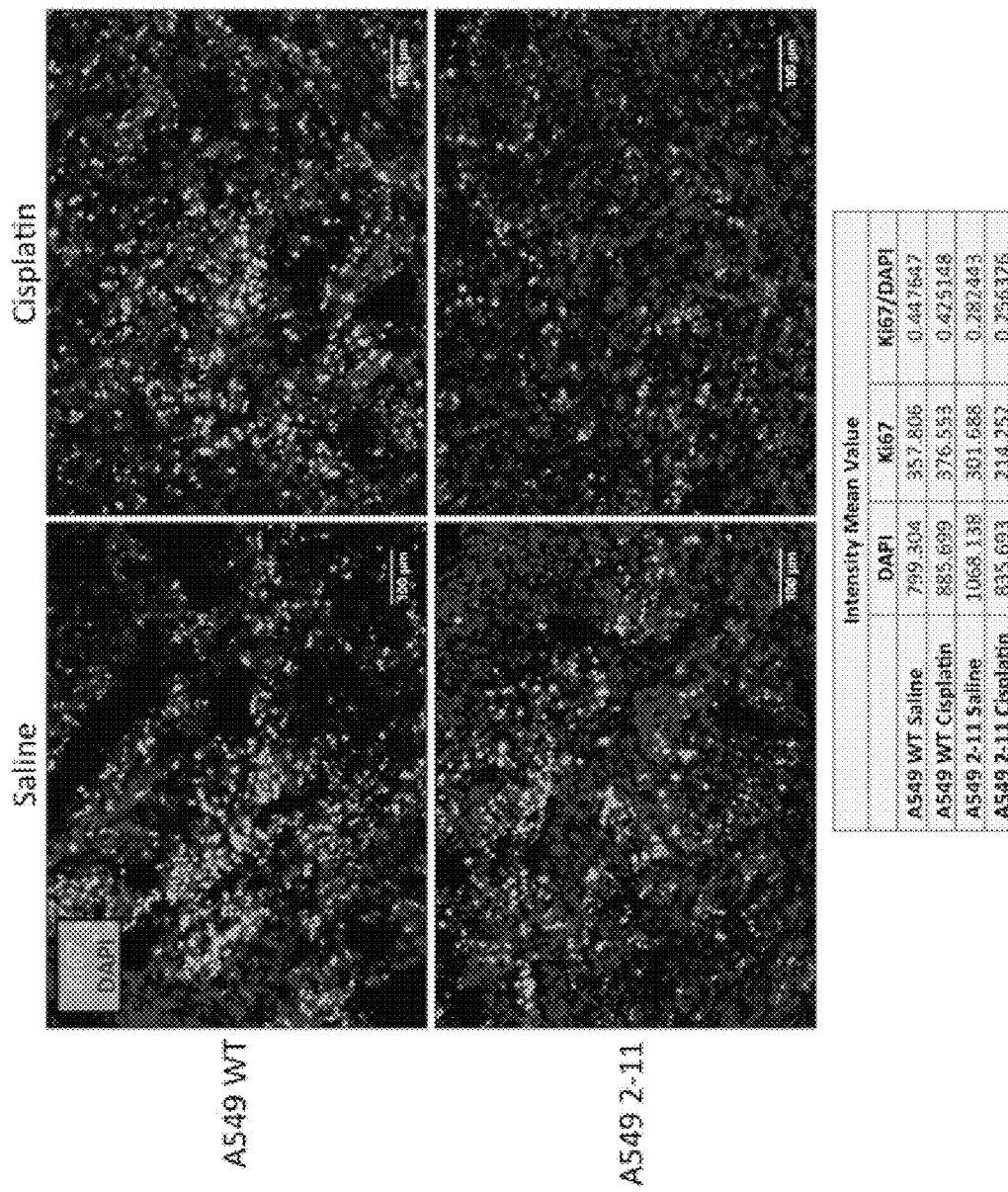
FIG. 6 shows proliferation of xenograft tumors. Representative images of xenograft tumors extracted from mice implanted with either wild type A549 or NRF2 knockout A549 cells (2-11) 16 days after initial treatment of either 2 mg/kg cisplatin or saline were sectioned and stained with Ki67 (green) and DAPI (blue). Fluorescence intensity mean values for DAPI and Ki67 were obtained for the images using the Zeiss Zen software and relative values were obtained for fluorescence intensity of Ki67. Scale bar represents 100 µm.

Since A549 2-11 knockout xenograft tumors exhibited smaller tumor volume compared to their wild type counterparts, we wanted to examine the proliferative activity within the tumors using Ki67, a well-known marker for proliferation, which presents during all active phases of cell cycle (G1, S, G2 and mitosis). Scholzen et al., J. Cell. Physiol. 182, 311-322 (2000). As shown in FIG. 6, within A549 cells treated with only saline, abundant Ki67-positive cells were observed; tumors extracted from mice treated with cisplatin produced similar levels of Ki67 positive cells. In the case of tumors generated from 2-11 cells, Ki67 staining is noticeably decreased and treatment with cisplatin resulted in even lower levels of Ki67, suggesting cisplatin enhances the response of the KO 2-11 cells by slowing down proliferation even further.

Figure 7A:
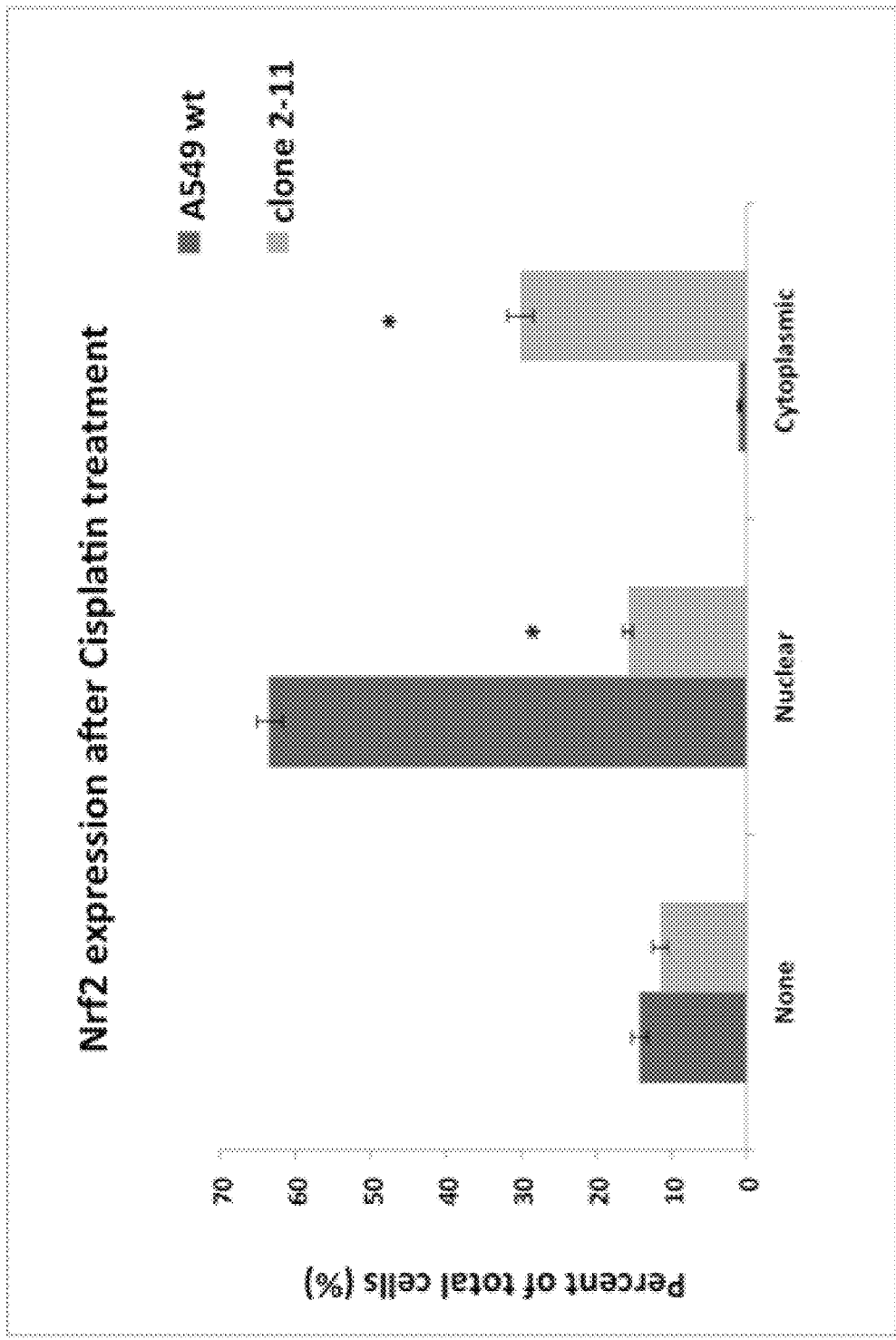
FIGS. 7A and 7B show cisplatin-induced nuclear and cytoplasmic localization of NRF2 in wildtype A549 cells and clone 2-11. Cells were treated with 2 µM Cisplatin, fixed and stained for NRF2. Immunocytochemistry was performed using fluorescence microscopy. Random fields were imaged and the total number of cells/field was counted. The percent of NRF2 positive stained cells over the total cells analyzed in each category was plotted in this graph. Error bars represent±SEM and * denotes a significant p value that is <0.05 (Student's t-test) (A). Representative images of nuclear and cytoplasmic localization of NRF2 in wild type A549 and NRF2 knockout A549 (2-11) (B). Scale bar represents 50 µm.
Figure 7B:
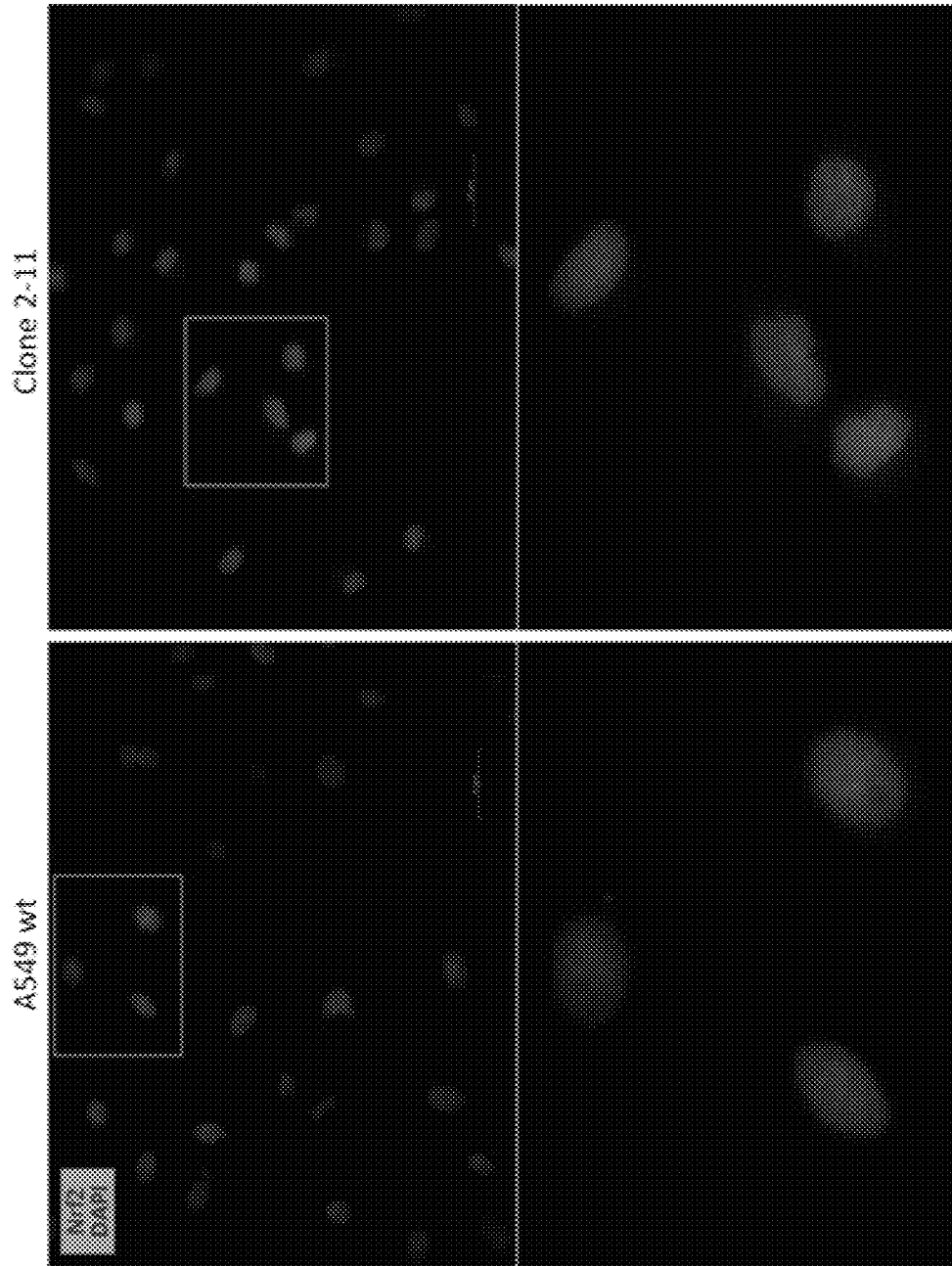

Taken together, the accumulated data build a strong case for clone 2-11 as a functional knockout since these cells enable a higher sensitivity to chemotherapy as compared to the wild-type counterpart. We sought to provide some explanation for this phenotype observed in both cell culture and in the mouse. The effect of the disruption of the NES region located in the Neh5 domain of NRF2 was further characterized using immunocytochemistry. Wild type A549 and clone 2-11 cells were pre-treated with 2 μM Cisplatin to stimulate NRF2 expression. Random fields of each cell sample were identified, imaged and total cell counts determined. Cells were quantified based on the following observed outcomes: no staining of NRF2, nuclear staining only or cytoplasmic staining only. FIG. 7A represents the average quantification of multiple replicates of several experiments with at least 10 fields of view incorporated into the data set. We observed a statistically significant difference in the degree of nuclear localization of NRF2 between wildtype A549 and clone 2-11 cells respectively. In wild-type cells, the majority of NRF2 is located in the nucleus while in the functional knockout cell line (2-11), NRF2 is predominantly found in the cytoplasm as seen in FIG. 7B. The images of cisplatin-induced wildtype and knockout cells (FIG. 7B) reflect the data presented in FIG. 7A.

Cell line 2-11 exhibited a heightened sensitivity to increasing dosages of cisplatin and to a lesser extent in response to increasing concentrations of carboplatin. When cisplatin is combined with vinorelbine, a heightened sensitivity is also observed. Cell killing was determined by the standard MTS assay. Chemosensitivity of the homozygous knockout cell line 2-11 was then evaluated in a xenograft mouse model wherein the cells were implanted in the back of a nude mouse and allowed to proliferate for 16 days. Subsequent tail vein injection of cisplatin, carboplatin or cisplatin and vinorelbine at various days after the tumor had grown to approximately 100 mm$^3$, led to a reduction in tumor proliferation over the course of the next 16 days. Interestingly, cell line 2-11 alone exhibited a slower growth phenotype in a xenograft mouse model even without the addition of chemotherapeutic drugs. This result indicates that the disruption of the NRF2 gene itself reduces proliferative activity to a small degree, although the addition of cisplatin, carboplatin or cisplatin/vinorelbine leads to a significant reduction in tumor cell proliferation.

Tumors isolated from mice implanted with wild type A549 cells or the clonal knockout cells treated with either cisplatin or saline were sectioned and stained for Ki67, a commonly used marker for cell proliferation. Ki67 is strictly associated with cell proliferation and is present during all active phases of the cell cycle, but absent in resting cells. Our results suggest that there is no difference in Ki67 levels in treated or untreated wild type A549 cells grown in the xenograft model, again reflecting the well-known resistance of A549 cells to cisplatin. In contrast, Ki67 levels in NRF2 knockout cells treated with cisplatin were found to be substantially lower when compared to the wild type counterparts. These results provide a plausible explanation for the reduced size of the tumor found in mice implanted with NRF2 knockout cells, a reduction in tumor cell proliferation as a function of CRISPR-directed gene editing. These results reflect those of Velma et al. (Biomark Insights 11, BMI.S39445, 2016) who reported that cisplatin-treated cells are arrested at the G0/G1 border as a function of increasing concentrations. Cisplatin reduces proliferation or retardation of cell cycle progression with an impact at the interface between G0 and G1. These data certainly indicate that disruption of NRF2 in A549 cells leads to a reduced proliferative phenotype, which may preclude the appearance of apoptosis in tumors analyzed at 16 days. It is possible that apoptosis may be evident shortly after the introduction of any of the four treatments of cisplatin taking place in the early part of the experiment.

When stimulated with stressors, functional NRF2 translocates to the nucleus where it binds to the ARE (antioxidant response element) sequence and activates transcription of the various downstream cytoprotective genes. The translocation of NRF2 to the nucleus (appears as purple) can be seen in the images of wildtype A549 cells (FIG. 7B). However, the genetic knockout of NRF2 in clone 2-11 causes loss of NRF2 function and appears to halt translocation of the protein, instead remaining in the cytoplasm, also seen in FIG. 7B. Functional knockouts may have value as CRISPR moves toward clinical application, particularly for cancer therapy.

Our results provide support for the notion that the combination of gene editing activity and chemotherapy act synergistically to reduce tumor cell growth. In our case, the treatment of A549 cells with CRISPR/Cas9 to disable NRF2 at the level of the gene also led to effective killing at lower dosages of multiple chemotherapeutic agents.

Example 4

Chemosensitivity In Vitro and in Xenograft Mouse Models of Melanoma, ESC, HNSCC, and Breast Cancer (Prophetic)

Following the methods in the examples above, the effects of CRISPR/Cas9-mediated NRF2 knockdown will be evaluated for additional cancers, both in vitro and in xenograft mouse models. For example, following the methods in Example 1 above, the gRNA1 sequence (5'-UCGAU-GUGACCGGGAAUAUCAGG) (SEQ ID NO:2) or the gRNA2 sequence (5'-UGAUUUAGACGGUAUGCAAC AGG) (SEQ ID NO:4) will be used to generate NRF2 knockdown cell lines of the human malignant melanoma A375 cell line (Wang, et al., 2018, Oxidative Medicine and Cellular Longevity Volume 2018, Article ID 9742154), the esophageal squamous cancer (ESC) cell lines KYSE-30, -50, -70, -110, -140, -150, -170, -180, -220, and -270 (Shibata et al., 2015, Neoplasia 13:864), the head and neck squamous cell carcinoma (HNSCC) HSC-4 cell line (Kitamura & Motohashi, 2018, Cancer Science 109:900), and the breast cancer (adenocarcinoma) cell line MCF7 (Kang et al., 2014, Scientific Reports 4:7201). Chemosensitivity of the genetically engineered NRF2-deficient cancer cell lines will be compared to that of the corresponding wild type cancer cell line in vitro following the methods provided in Example 2 above. For each cell line, chemosensitivity to the following chemotherapeutic agents will be evaluated as shown in Table 4 below.

TABLE 4

Chemotherapeutic Agents for Evaluation of Chemosensitivity

| Cancer Cell lines | Chemotherapeutic Agent |
| --- | --- |
| human malignant melanoma (A375) | cisplatin |
| esophageal squamous cancer (ESC) (KYSE-30, -50, -70, -110, -140, -150, -170, -180, -220, and -270) | 5-fluorouracil |
| head and neck squamous cell carcinoma (HNSCC) (HSC-4) | cetuximab, cisplatin, fluorouracil, carboplatin |
| breast cancer (MCF7) | doxorubicin |

Wild type and NRF2-deficient cancer cell lines as shown in Table 4 above will be implanted into nude mice and evaluated for chemosensitivity as described in Example 3 above.

Example 5

RF2 gRNA Designs

```
ppx458 plasmid vector
                                          (SEQ ID NO: 9)
Exon 4 gRNA1 - 5' TCGATGTGACCGGGAATATCAGG 3'

(SEQ ID NO: 10)
Exon 4 gRNA2 - 5' TGATTTAGACGGTATGCAACAGG 3'
```

The NRF2 gene-coding sequence was entered into the Zhang lab's online generator (available on the MIT website) and the gRNA with the highest score was chosen for gRNA1

(5' TCGATGTGACCGGGAATATC<u>AGG</u> 3' (SEQ ID NO:9)) and a previously validated gRNA targeting NRF2 was also chosen for gRNA2 (5' TGATTTA-GACGGTATGCAAC<u>AGG</u> 3' (SEQ ID NO:10)) (1). The CRISPR plasmid was cloned using standard cloning methods with single-step digestion-ligation. The CRISPR guide sequences with appropriate 5' overhangs were cloned into the px458 backbone vector digested with BbsI (plasmid 48138, Addgene). These two plasmids were transfected separately to knockout NRF2 in the A549 cell line, creating cell line 1-40 and 2-11, with small indels at the cleavage site (2).

Figure 8:
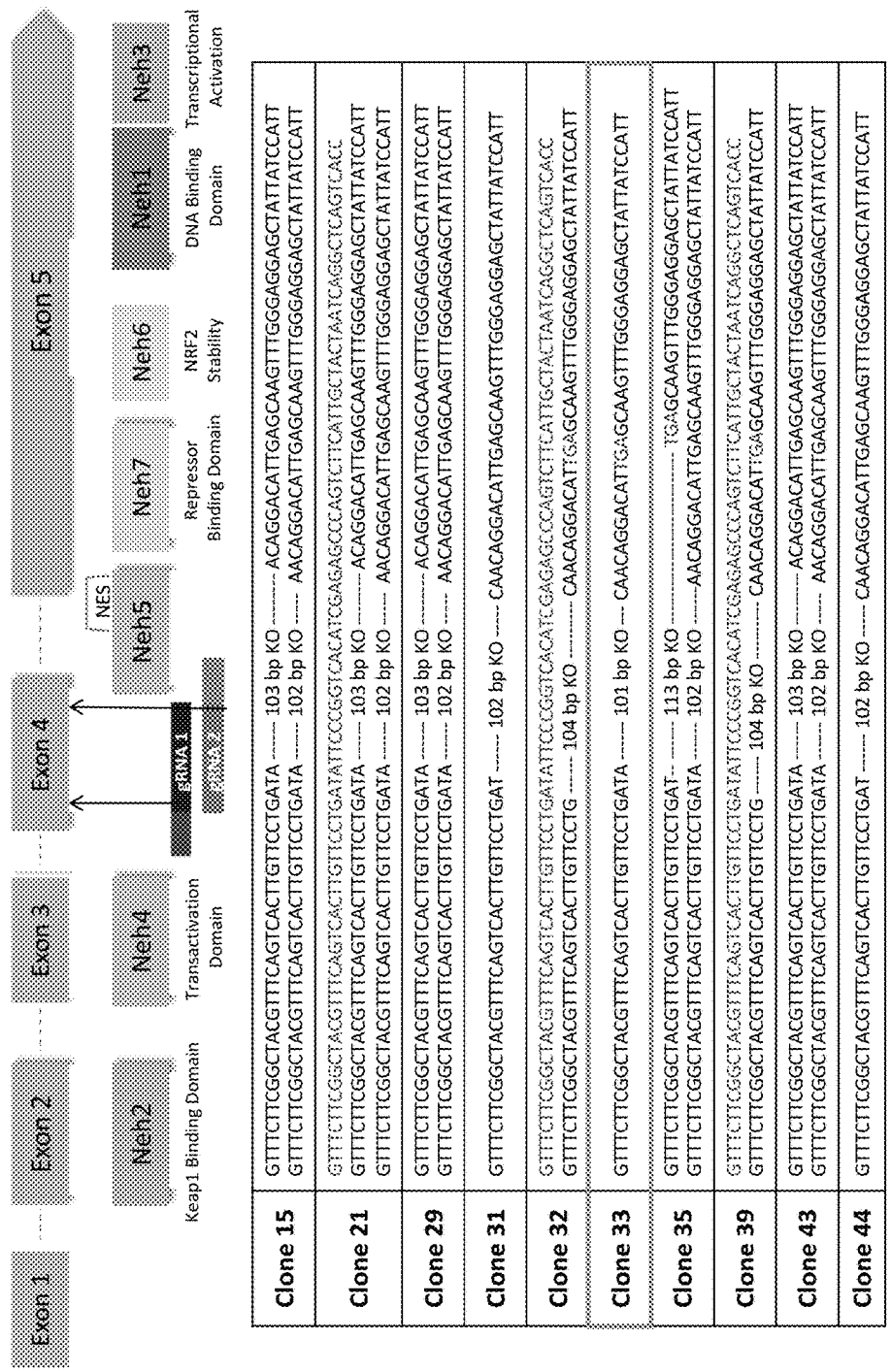
FIG. 8 shows clonal analysis using two CRISPR plasmid constructs to cleave 103 bases in exon 4 of NRF2. The top panel displays the structural domains and target region of gRNA1 and gRNA2 designed and used by Bialk et al., *Mol. Ther.-Oncolytics* 11, 75-89 (2018). The lower panel displays the genetic analysis of various clones recovered by fluorescence activated single cell sorting (FACS). Sequences in green indicate a wildtype sequence and bases highlighted in red indicate a frameshift resulting in a stop codon. SEQ ID NO:88 (clone 15 103 bp KO), SEQ ID NO:89 (clone 15 102 bp KO), SEQ ID NO:90 (clone 21 no KO), SEQ ID NO:91 (clone 21 103 bp KO), SEQ ID NO:92 (clone 21 102 bp KO), SEQ ID NO:93 (clone 29 103 bp KO), SEQ ID NO:94 (clone 29 102 bp KO), SEQ ID NO:95 (clone 31 102 bp KO). SEQ ID NO:96 (clone 32 no KO), SEQ ID NO:97 (clone 32 104 bp KO), SEQ ID NO:98 (clone 33 101 bp KO), SEQ ID NO:99 (clone 35 113 bp KO), SEQ ID NO:100 (clone 35 102 bp KO), SEQ ID NO:101 (clone 39 no KO), SEQ ID NO:102 (clone 39 104 bp KO), SEQ ID NO:103 (clone 43 103 bp KO), SEQ ID NO:104 (clone 43 102 bp KO), SEQ ID NO:105 (clone 44 102 bp KO).

Both plasmid constructs, gRNA1 and gRNA2, were transfected (Lipofection) in the A549 cell line targeting NRF2 in order to cleave and remove a 103 base pair fragment. The transfected cells were single-cell sorted and expanded. Clonal populations were initially screened using PCR and gel electrophoresis to visually analyze a shift in amplicon size. Once screened, DNA was sent out for sequenced across exon 4 of NRF2. FIG. 8 shows the ten clones analyzed for INDEL formation.

```
                                        (SEQ ID NO: 11)
Exon 3 gRNA3 - 5' AAGTACAAAGCATCTGATTTGGG 3'

(SEQ ID NO: 12)
Exon 3 gRNA4 - 5' AGCATCTGATTTGGGAATGTGGG 3'
```

The previously described experiments were designed to cleave within exon 4. In order to ensure complete knockout of NRF2, gRNA3 (5' AAGTACAAAGCATCTGATTT<u>GGG</u> 3' (SEQ ID NO:11)) and gRNA4 (5' AGCATCTGATTTGG-GAATGT<u>GGG</u> 3' (SEQ ID NO:12)) (NRF2 sequence entered into Benchling and gRNA were strategically chosen) were designed to be cloned into the px458 backbone vector to cleave within exon 3. The newly designed gRNAs would be used in conjunction with the previously designed gRNA1 and gRNA2 to cleave from exon 3 to exon 4. gRNA4 was designed to be used with gRNA1 which would remove 782 based. gRNA3 was designed to be used with gRNA2 which would remove 877 bases. Both of these combinations would result in loss of the majority of exon 3 and exon 4, leaving only the beginning of exon 3 and end of exon 4. (Sanjana et al., Nat. Methods 11:783 (2014); Bialk et al., Mol. Ther.— Oncolytics 11:75-89 (2018))

```
Cas9 RNP
                                        (SEQ ID NO: 13)
Exon 2 gRNA - 5' TGGATTTGATTGACATACTTTGG 3'
(Neh2 for NRF2 KO)

(SEQ ID NO: 14)
Exon 5 gRNA - 5' GCTTCTTACTTTTGGGAACAAGG 3'
(Neh3 for NRF2 KO)
```

The following gRNAs were designed to be complexed with tracrRNA and Cas9 protein to form a ribonucleoprotein (RNP) complex. The gRNAs were designed using the NRF2 sequence in Benchling.

Figure 9:
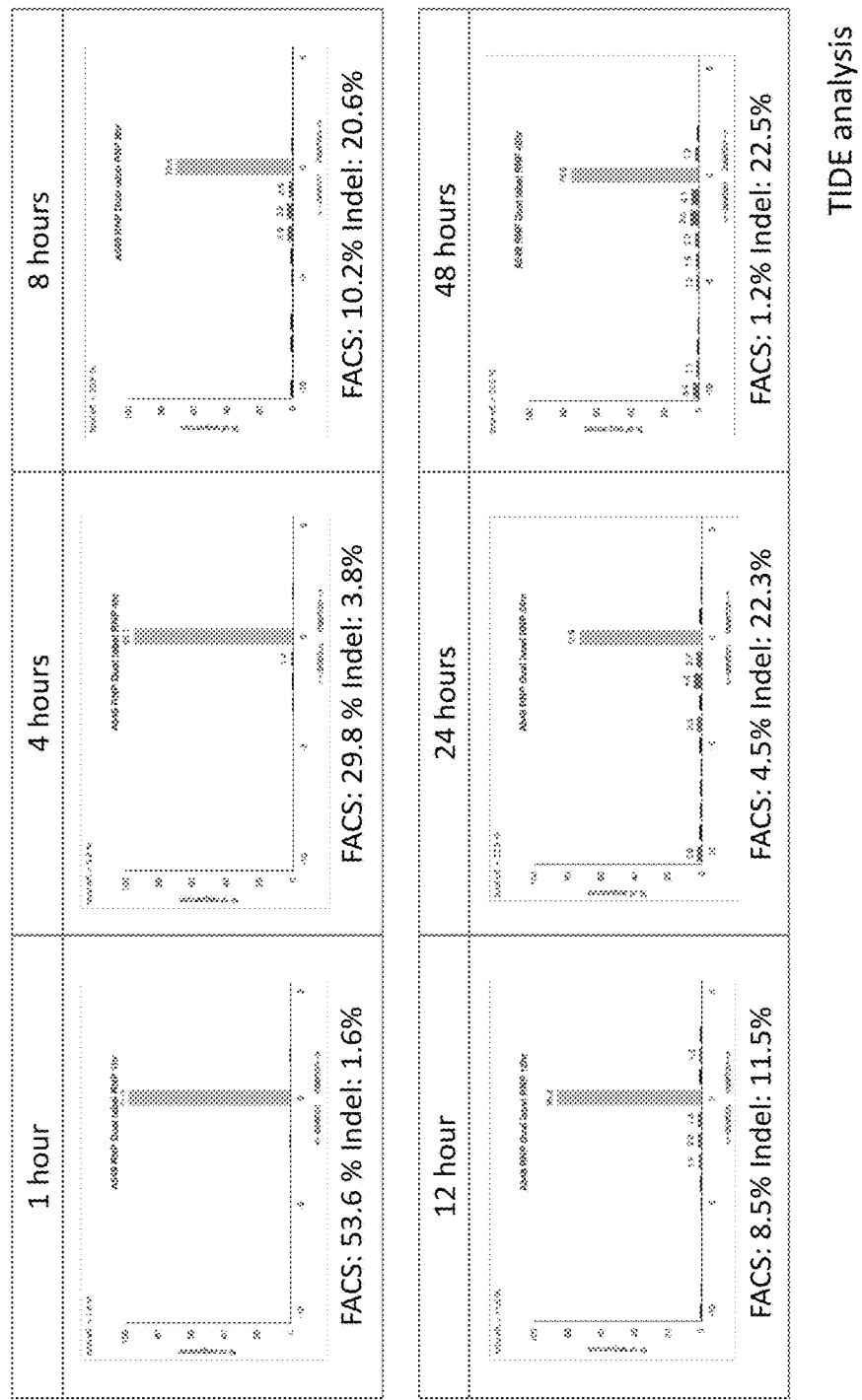
FIG. 9 shows population sequence analysis of CRISPR/Cas9-targeted cells. The A549 cell line was transfected with a RNP complex targeting the Neh2 domain in Exon 2 using gRNA 5' TGGATTTGATTGACATACTT<u>TGG</u> 3' (SEQ ID NO:13). Cells were collected at 1, 4, 8, 12, 24, 48 h post transfection. DNA was isolated, sequenced (across exon 2 of NRF2) and analyzed using Tracking of Indels by DEcomposition (TIDE). The indel efficiencies (%) are listed in the figure.

Exon 2 gRNA (5' TGGATTTGATTGACATACTT<u>TGG</u> 3' (SEQ ID NO:13)) was designed to cleave at the beginning of Neh2 in exon 2 in order to knockout NRF2. The RNP was transfected in A549 cells and collected at various times points to assess indel formation (TIDE analysis), shown in FIG. 9. Cells could be single-cell sorted by FACS to obtain clonal populations to determine the extent of NRF2 KO.

Exon 5 gRNA (5' GCTTCTTACTTTTGGGA<u>A</u>CA<u>AGG</u> 3' (SEQ ID NO:14)) was designed to be to cleave at the end of Neh3 in exon 5 and to be used in conjunction with Exon 2 gRNA. By using both gRNAs, the entire NRF2 gene would be removed (3429 bp). Cells would be transfected with both RNP complexes and single-cell sorted by FACS. Clonal populations would be analyzed for NRF2 KO.

```
Cas12a RNP
                                        (SEQ ID NO: 15)
Exon 2 gRNA - 5' TTTGATTGACATACTTTGGAGGCAA 3'
(Neh2 for NRF2 KO)

(SEQ ID NO: 16)
Exon 5 gRNA - 5' TTTTCCTTGTTCCCAAAAGTAAGAA 3'
(Neh3 for NRF2 KO)
```

The following gRNAs were designed to be complexed with tracrRNA and Cas12a protein to form a ribonucleoprotein (RNP) complex. The gRNAs were designed using the NRF2 sequence in Benchling.

Figure 10:
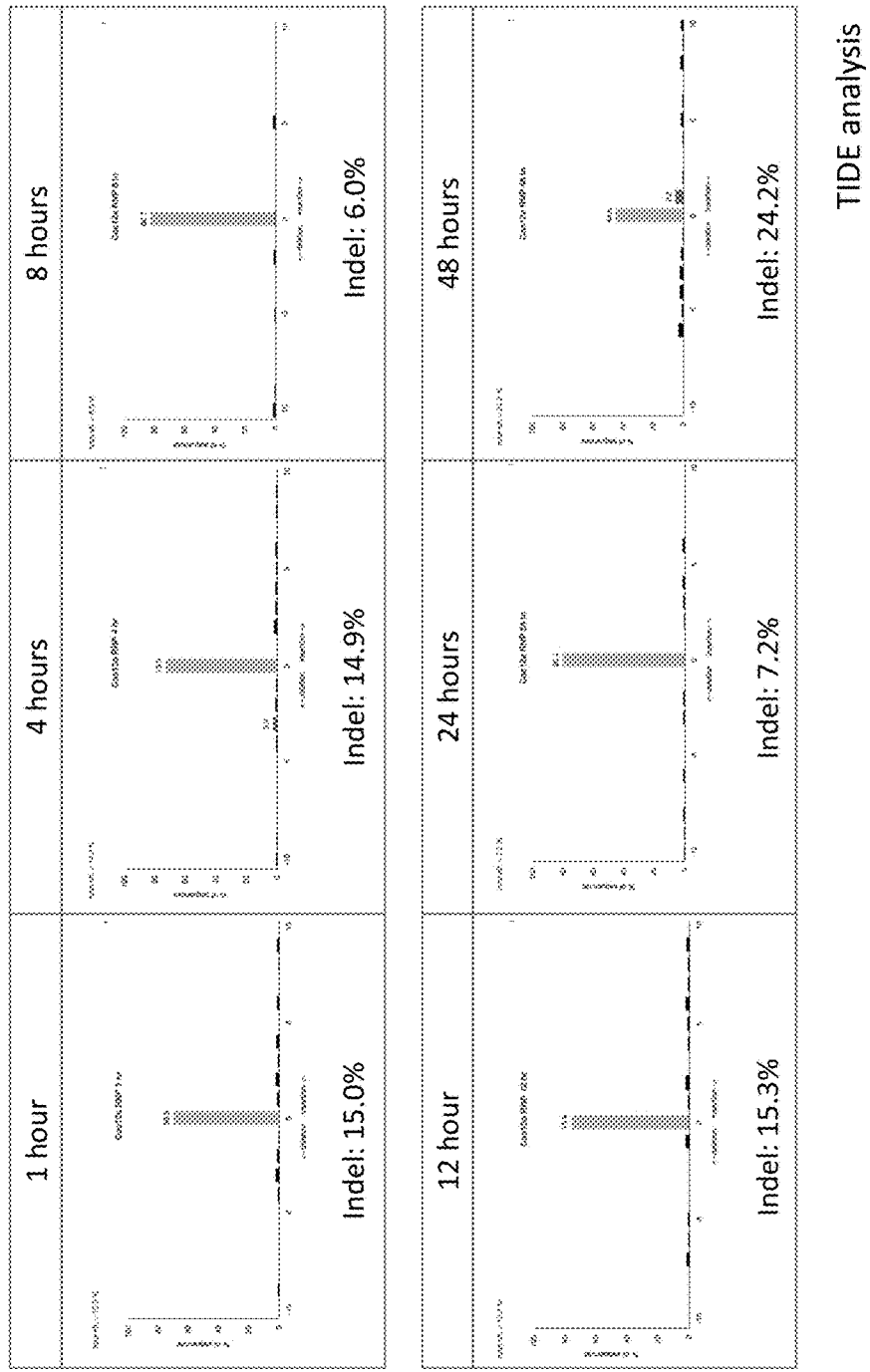
FIG. 10 shows Population Sequence Analysis of CRISPR/Cas12a-targeted cells. The A549 cell line was transfected with a RNP complex targeting the Neh2 domain in Exon 2 using gRNA 5' <u>TTTG</u>ATTGACATACTTTGGAGGCAA 3'. Cells were collected at 1, 4, 8, 12, 24, 48 h post transfection. DNA was isolated, sequenced (across exon 2 of NRF2) and analyzed using TIDE. The indel efficiencies (%) are listed in the figure.

Exon 2 gRNA (5' <u>TTTG</u>ATTGACATACTTTGGAGGCAA 3' (SEQ ID NO:15)) was designed to cleave at the beginning of Neh2 in exon 2 in order to knockout NRF2. The RNP was transfected in A549 cells and collected at various times points to assess indel formation, shown in FIG. 10. Cells could be single-cell sorted by FACS to obtain clonal populations to determine the extent of NRF2 KO.

Exon 5 gRNA (5' <u>TTTT</u>CCTTGTTCCCAAAAGTAAGAA 3' (SEQ ID NO:16)) was designed to cleave at the end of Neh3 in exon 5 and to be used in conjunction with Exon 2 gRNA. By using both gRNAs, the entire NRF2 gene would be removed (3432 bp). Cells would be transfected with both RNP complexes and single-cell sorted by FACS. Clonal populations would be analyzed for NRF2 KO.

Example 6

Figure 11:
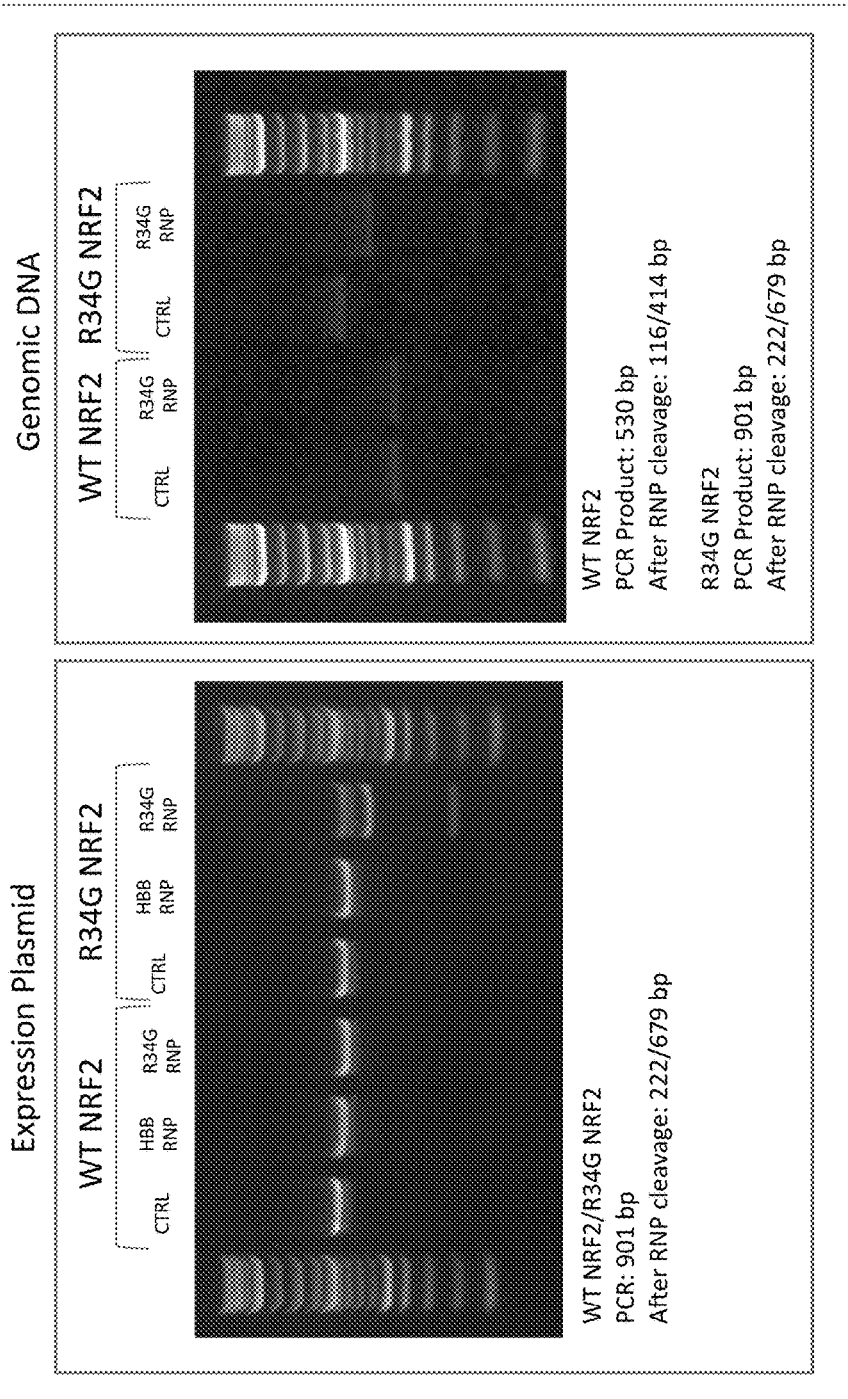
FIG. 11 shows CRISPR target recognition of lung tumor DNA Sequence. An in vitro cleavage reaction was carried out with a CRISPR/Cas9 RNP complex using a gRNA targeting the R34G mutation. The reaction included testing cleavage of an NRF2 expression plasmid containing the R34G mutation as well as using an amplicon 901 base pairs long from the expression plasmid. In both instances, the R34G RNP only recognizes and cleaves with the mutation present, which creates a new PAM site.

The gRNA that would be used to target the R34G mutation using CRISPR/Cas9 is: 5' GATATAGATCTTG-GAGTAAG<u>TGG</u> 3' (SEQ ID NO:25) (underlined—PAM site, bold—R34G mutation). As proof of concept, an in vitro cleavage reaction was carried out to assess the level of discrimination using the R34G gRNA in a ribonucleoprotein complex (RNP). Wildtype and mutated (R34G) NRF2 sequences were incubated with the R34G RNP complex and cleavage products were analyzed by gel electrophoresis (FIG. 11).

To test the specificity and differential recognition of CRISPR/Cas9 in normal versus mutated cells, we will use the BEAS-2B cell line, which is derived from normal human bronchial epithelium, to create an endogenous R34G mutation. This will be done by transfecting two CRISPR/Cas9 constructs (plasmid vector or RNP) designed to cleave within the Neh2 domain. The fragment being cleaved will be replaced using single stranded oligonucleotides, with the same sequence except for the single base change that creates the R34G mutation. The transfected cells will be sorted by fluorescence activated single cell sorting (FACS) for clonal expansion and clonal sequence analysis. The mutation should induce oncogenesis in the engineered cell line.

Once established, we will test the specificity and efficiency of R34G-targeting CRISPR/Cas9 on the new mutated cell line. We will assess gene editing activity by analyzing the cleavage site for indel formation after transfecting the new clonal cell line with the R34G-targeting CRISPR. As a control to show differential recognition of the R34G-targeting CRISPR, we will transfect the wildtype cell line with the R34G CRISPR and assess indel formation. Following these experiments, we will use various techniques to analyze the functionality of NRF2 post gene editing as well as the effect CRISPR cleavage on cellular pathways. We will determine the baseline of chemoresistance in the mutated cell line before gene editing using the MTS assay to measure cell viability. We will carry out the same experiment after transfection of the R34G CRISPR to assess the response to chemotherapeutic drugs. We will do a western blot analysis to determine the degree of NRF2 knockout after gene editing.

A similar approach will be taken in a xenograft model to show the differential recognition of the R34G CRISPR in mutated cells versus normal (i.e., non-cancerous) cells. We will used the established, mutated cell line to inject a mouse xenograft. Once the tumor is established, the R34G CRISPR will be systemically delivered. The tumors will be resected and used for thorough genetic analysis of the NRF2 gene across the cleavage site. Normal (i.e., non-cancerous) tissue will be randomly sampled to assess the presence/absence of off-target gene editing.

TABLE 5

Cancer derived gRNAs from variant NRF2s (substitution in bold)

| | | |
|---|---|---|
| SEQ ID NO: 17 | Guide RNA3 (gRNA3) recognition element | 3'-AAACTAACTGTATGAAACCTCCC-5' |
| SEQ ID NO: 18 | Guide RNA3 (gRNA3) | 5'-UUUGAUUGACAUACUUUGGAGGG-3' |
| SEQ ID NO: 19 | Guide RNA4 (gRNA4) recognition element | 3'-GAATGAGGTTCTAGATATAGACC-5' |
| SEQ ID NO: 20 | Guide RNA4 (gRNA4) | 5'-CUUACUCCAAGAUCUAUAUCUGG-3' |
| SEQ ID NO: 21 | Guide RNA5 (gRNA5) recognition element | 3'-TATGAAACCTCCGTTCTATATCC-5' |
| SEQ ID NO: 22 | Guide RNA5 (gRNA5) | 5'-AUACUUUGGAGGCAAGAUAUAGG-3' |
| SEQ ID NO: 23 | Guide RNA6 (gRNA6) recognition element | 3'-TCCGTTCTATATCTAGAACCTCC-5' |
| SEQ ID NO: 24 | Guide RNA6 (gRNA6) | 5'-AGGCAAGAUAUAGAUCUUGGAGG-3' |
| SEQ ID NO: 25 | Guide RNA7 (gRNA7) recognition element | 3'-CTATATCTAGAACCTCATTCACC-5' |
| SEQ ID NO: 26 | Guide RNA7 (gRNA7) | 5'-GAUAUAGAUCUUGGAGUAAGUGG-3' |
| SEQ ID NO: 27 | Guide RNA8 (gRNA8) recognition sequence | 3'-ACTGACTTCAGTTTATGAAGACC-5' |
| SEQ ID NO: 28 | Guide RNA8 (gRNA8) | 5'-UGACUGAAGUCAAAUACUUCUGG-3' |
| SEQ ID NO: 29 | Guide RNA9 (gRNA9) recognition sequence | 3'-AAGTAGATCAACATTGACTCGCC-5' |
| SEQ ID NO: 30 | Guide RNA9 (gRNA9) | 5'-UUCAUCUAGUUGUAACUGAGCGG-3' |
| SEQ ID NO: 31 | Guide RNA10 (gRNA10) recognition sequence | 3'-TAAGTGGACAGAGAAGTAGATCC-5' |
| SEQ ID NO: 32 | Guide RNA10 (gRNA10) | 5'-AUUCACCUGUCUCUUCAUCUAGG-3' |
| SEQ ID NO: 33 | Guide RNA11 (gRNA11) recognition sequence | 3'-GAGTCAATGTTGATCTACTTCCC-5' |
| SEQ ID NO: 34 | Guide RNA11 (gRNA11) | 5'-CUCAGUUACAACUAGAUGAAGGG-3' |
| SEQ ID NO: 35 | Guide RNA12 (gRNA12) recognition sequence | 3'-ACTTAACCCTCTTTAAGTGGACC-5' |
| SEQ ID NO: 36 | Guide RNA12 (gRNA12) | 5'-UGAAUUGGGAGAAAUUCACCUGG-3' |
| SEQ ID NO: 37 | Guide RNA13 (gRNA13) recognition sequence | 3'-GTTGATCTACTTCTCTGTCCACC-5' |
| SEQ ID NO: 38 | Guide RNA13 (gRNA13) | 5'-CAACUAGAUGAAGAGACAGGUGG-3' |
| SEQ ID NO: 39 | Guide RNA14 (gRNA14) recognition sequence | 3'-TATTATCGAGGAGGGTTTGAACC-5' |
| SEQ ID NO: 40 | Guide RNA14 (gRNA14) | 5'-AUAAUAGCUCCUCCCAAACUUGG-3' |
| SEQ ID NO: 53 | Guide RNA15 (gRNA15) recognition sequence | 3'-AAAAAGCGAGTAATGTTGATCC-5' |

TABLE 5-continued

Cancer derived gRNAs from variant NRF2s (substitution in bold)

SEQ ID NO: 54  Guide RNA15 (gRNA15)  5'-UUUUUCGCUCAGUUACAACUAGG-3'

SEQ ID NO: 55  Guide RNA16 (gRNA16)  3'-GTTGATCTACTTCTCTGTCCACC-5'
               recognition sequence SEQ ID NO: 56  Guide RNA16 (gRNA16)  5'-CAACUAGAUGAAGAGACAGGUGG-3'

PAM sequence underlined.

Example 7

H1703 (NCI-H1703) is a lung squamous cell carcinoma cell line with a missense mutation at codon 285 (GAG→AAG) of its p53 gene. You et al., Cancer Res. 60:1009-13 (2000). NCI-H1703 has been shown to primarily express FGFR1c and to induce Erk1/2 phosphorylation upon stimulation with FGF2. Marek et al., Mol. Pharmacol. 75:196-207 (2009).

```
Cas9 RNP
Exon 2 gRNA 3 -
                                    (SEQ ID NO: 64)
5' TGGAGGCAAGATATAGATCTTGG 3' (Neh2 for NRF2 KO)

R34G ssDNA template -
                                    (SEQ ID NO: 65)
5' TTAAAAAACATGAGCTCTCTCCTTCCTTTTTTTGTCTTAAACATAGG

ACATGGATTTGATTGACATACTTTGGAGGCAAGATATAGATCTTGGAGTA

AGTGGAGAAGTATTTGACTTCAGTCAGCGACGGAAAGAGTATGAGCTGGA

AAAACAGAAAAAACTTGAAAAGGAAAGACAAGAACAACTCCAAAAGGAGC

AAG 3' (underlined, intended R34G mutation)
```

The Exon 2 gRNA 3 was designed to cleave at the D29 codon in exon 2 of the NRF2 gene in order to recreate the R34G mutation. The gRNA was complexed with Cas9 protein to form a RNP and was used with the R34G template DNA to facilitate DNA repair and introduce an intended R34G mutation in the NRF2 gene. The experiment yielded several clonal-derived cell lines which are being characterized further. FIG. 30 displays the clones that were genetically analyzed by DECODR for indel formation. Clone 26 (G9_H1703-26) contains a homozygous R34G mutation, preceded by a 4 bp deletion at the cleavage site of the gRNA used in the transfection. Clone 53(G2_H1703_R34G_53) contains a homozygous R34G mutations, preceded by a 2 bp deletion at the cleavage site of the gRNA used in the transfection. Clone 2-31 (H1703_R34G_2-31) contains two wildtype alleles with two distinct indel patterns, a 6 bp deletion on one allele and a 4 bp deletion on the other allele, at the cleavage site of the gRNA used in the transfection. Clone 2-91 (H1703_R34G_2-91) contains a heterozygous R34G mutation along with a wildtype allele containing a 20 bp deletion at the cleavage site of the gRNA used in the transfection. These clones will be used to further characterize the effect of the R34G mutation and NRF2 KO in exon 2 in the H1703 cell line.

The following gRNAs were designed to be used in the px458 plasmid vector as well as with Cas9 RNP for further experiments in the H1703 cell line. Individual and both RNP complexes is used to create NRF2 KO clonal-derived cell lines for characterization of the NRF2 KO in the H1703 cell line. The clonal-derived cell lines is used for MTS proliferation assay to determine chemosensitivity

```
Cas9 RNP
Exon 4 gRNA1 -
                                    (SEQ ID NO: 66)
5' TCGATGTGACCGGGAATATCAGG 3' (NRF2 KO)

Exon 4 gRNA2 -
                                    (SEQ ID NO: 67)
5' TGATTTAGACGGTATGCAACAGG 3' (NRF2 KO)
```

Example 8

(Prophetic) Chemosensitivity is Increased in NRF2 Knockout H1703 Cell Lines

Methods

MTS Cell Proliferation Assay

Cell viability will be evaluated using the CellTiter 96 Aqueous Non-Radioactive Cell Proliferation Assay (Promega, Madison, Wis.). H1703 cell lines will be plated at $2 \times 10^3$ cells per well and will be allowed to culture for 24 hours. The cell media will then be aspirated, the cells will be washed with PBS, then will be exposed to the MTS reagent for 3 hours. After 3 hours of MTS bio-reduction by proliferating cells, the formazan product's absorbance will be measured using a 450 nm filter on an Infinite 2000 PRO microplate reader (Tecan, Mannadorf, Switzerland). Cell viability after drug exposure will be evaluated using the CellTiter 96 Aqueous Non-Radioactive Cell Proliferation Assay. H1703 cell lines will be plated at $2 \times 10^3$ cells per well and allowed to culture for 24 hours. The cells will then be treated with cisplatin, carboplatin, or a combination of cisplatin and vinorelbine for three days. The cell media will then be aspirated, the cells will be washed with PBS, then will be exposed to the MTS reagent for 3 hours. After 3 hours of MTS bio-reduction by proliferating cells, the formazan product's absorbance will be measured using a 450 nm filter on an Infinite 2000 PRO microplate reader.

Results

To examine the chemosensitivity of the genetically engineered NRF2-deficient H1703 cell lines, the MTS assay will be utilized. Wild type and NRF-2 deficient H1703 cells will be exposed to increasing dosages of cisplatin. After 72 hours, cisplatin will be removed, and the MTS reagent will be added for three hours after which time the population will be measured for the absorbance of formazan. The data will show that wild type H1703 cells are resistant to high dosages of Cisplatin. In the genetically engineered knockout cell lines, we will observe an increase in chemosensitivity in a dose-dependent fashion. The NRF2 knockout cells will display a heightened sensitivity. Thus, it is possible that we will observe a gene dosage effect of sorts in that the heterozygous cell line exhibits more resistance to cisplatin than homozygous knockout cells because it contains at least one viable gene copy.

Example 9

Single guide RNAs were ordered from Synthego (Menlo Park, Calif.). ALT-R SpCas9 from IDT was used.

| sgRNA length | Sequence (5' → 3') | SEQ ID NO: |
|---|---|---|
| 23 nt | CAAGATATAGATCTTGGAGTAAG | 59 |
| 22 nt | AAGATATAGATCTTGGAGTAAG | 60 |
| 20 nt | GATATAGATCTTGGAGTAAG | 61 |
| 18 nt | TATAGATCTTGGAGTAAG | 62 |
| 17 nt | ATAGATCTTGGAGTAAG | 63 |

H1703 parental cells were cultured 48 hours prior to transfections and about 60-80% confluent on the day of transfection. $10^6$ cells per 100 ul was used per transfection and each condition was run in duplicate.

Figure 12:
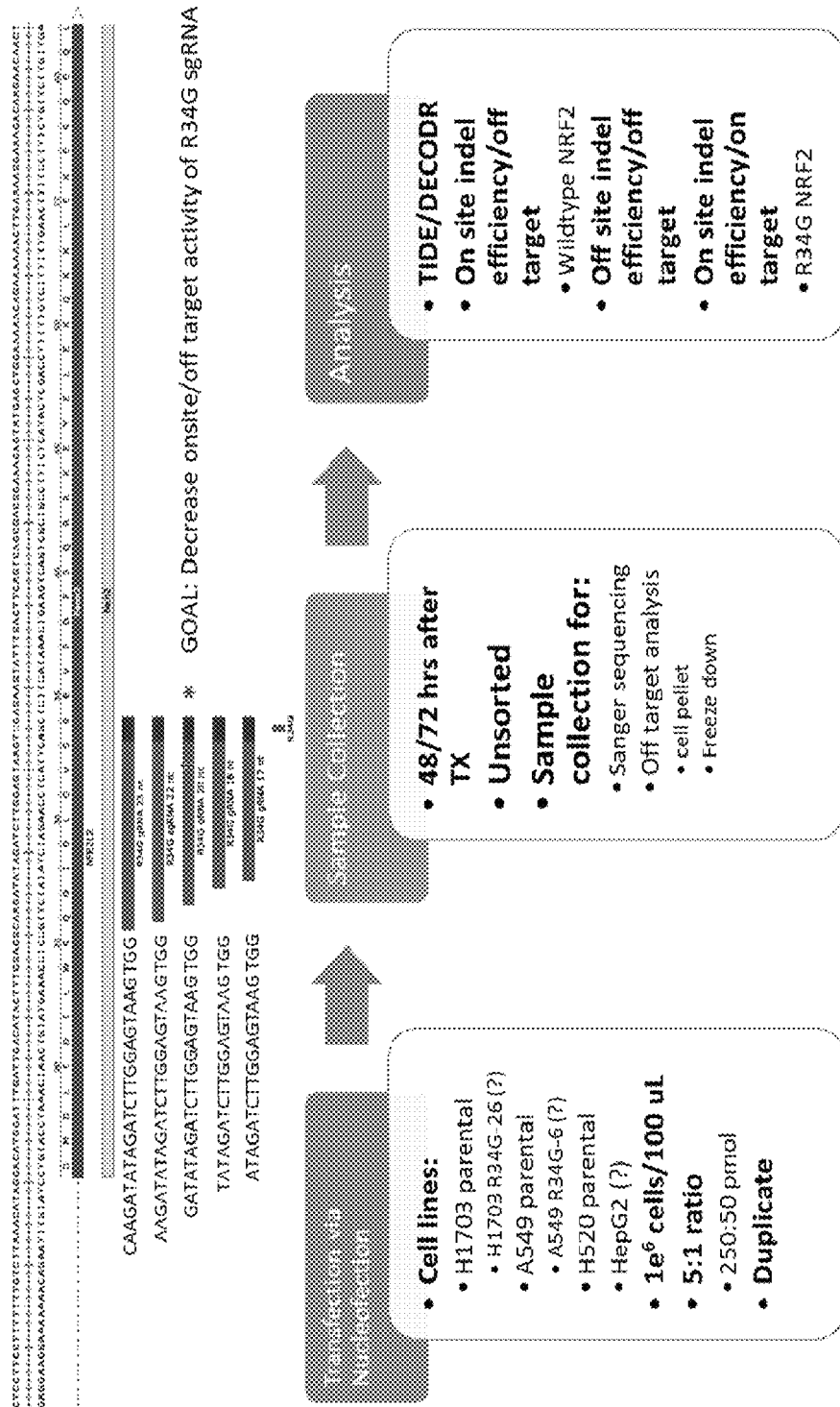
FIG. 12 shows a Schematic diagram and experimental design for assessing off targets using R34G sgRNA at various lengths. Five sgRNAs (SEQ ID NOs: 59-63) were designed using R34G mutation as the PAM site to assess on target and off target indel efficiency. The figure presents an overview of the experimental design including CRISPR/Cas9 complexing, transfection of lung cancer cell lines, sample collection and analysis.

Each CRISPR/Cas9 RNP was complexed at a 5:1 ratio of sgRNA to Cas9. 250 pmol of sgRNA was complexed at room temperature with 50 pmol of Cas9, in duplicate. The RNP complex was then transfected into H1703 parental cells using nucleofection (Lonza) with the SF Nucleofection Kit. Transfected cells were plated and allowed to recover for 72 hours. After the 72 hours, each sample of cells was collected by trypsinization and pelleted for further analysis. Cell pellets were used for genomic DNA isolation, PCR and Sanger sequencing. Sanger sequences were used for indel analysis by TIDE (overall scheme shown in FIG. 12).

It has been reported that gRNA length can affect target specificity (Fu et al., Nat. Biotechnol. 32:279-84 (2014)). The efficiency of indel formation of the various length R34G sgRNAs to the wildtype "on-target" site was evaluated. sgRNAs for each length were synthetized and complexed with purified Cas9. Replicate experiments were carried out with H1703 lung squamous cells that were transfected with each RNP, recovered for 72 hours, then analyzed for indel formation. No R34G site is present in the wildtype NRF2 gene in the H1703 cell line, therefore only minimal or background gene editing activity is expected.

Figure 13:
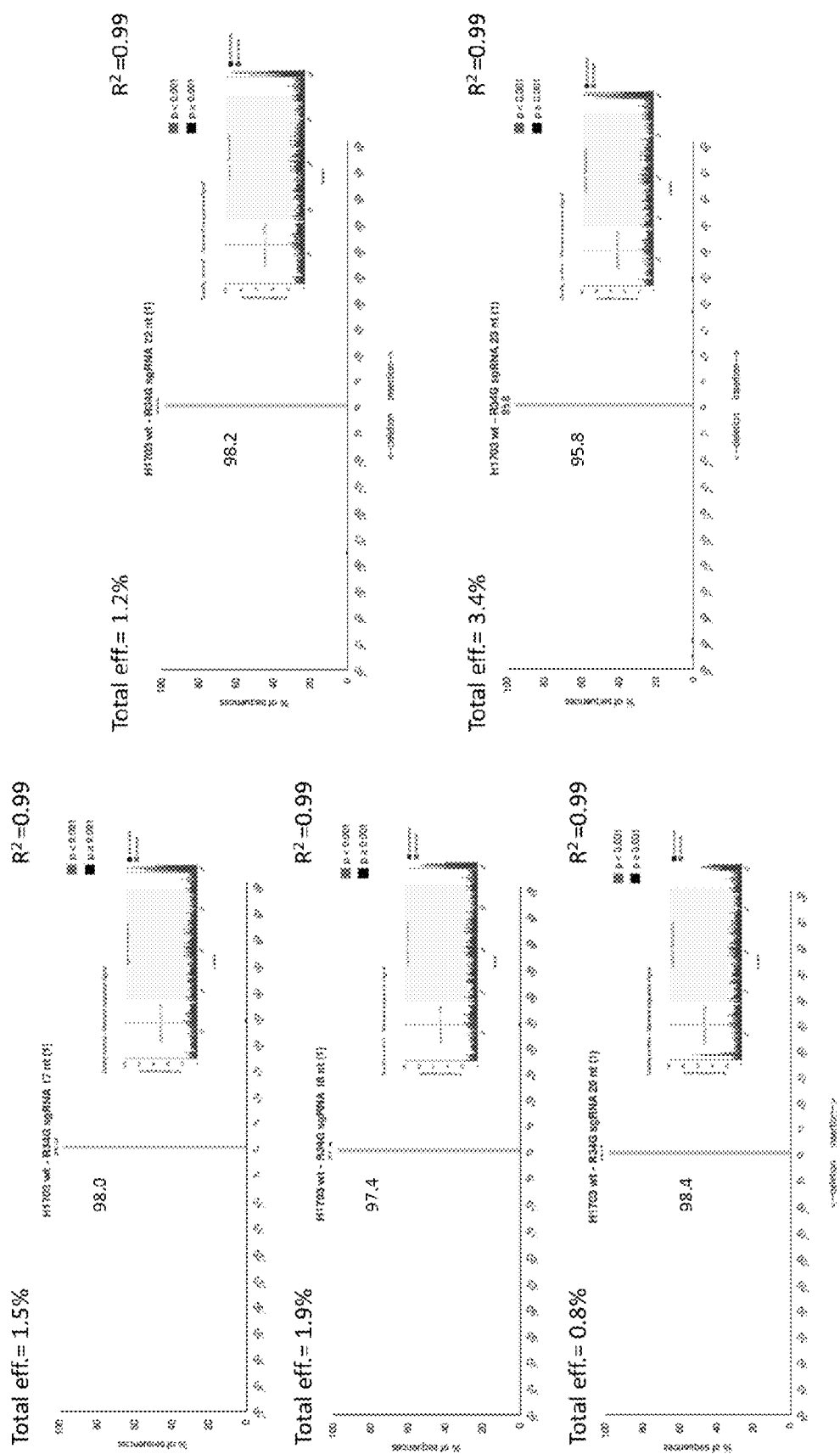
FIG. 13 shows genetic analysis by TIDE for indel efficiency of R34G sgRNA at various lengths—Replicate 1. The H1703 parental cell line was transfected with complexed CRISPR/Cas9 RNP (250 pmol sgRNA to 50 pmol Cas9). After a 72 hour recovery period, a sample for each R34G sgRNA length was collected for genomic DNA isolation, PCR amplification, sanger sequencing and TIDE analysis. This figure shows the genetic analysis by TIDE of replicate 1.
Figure 14:
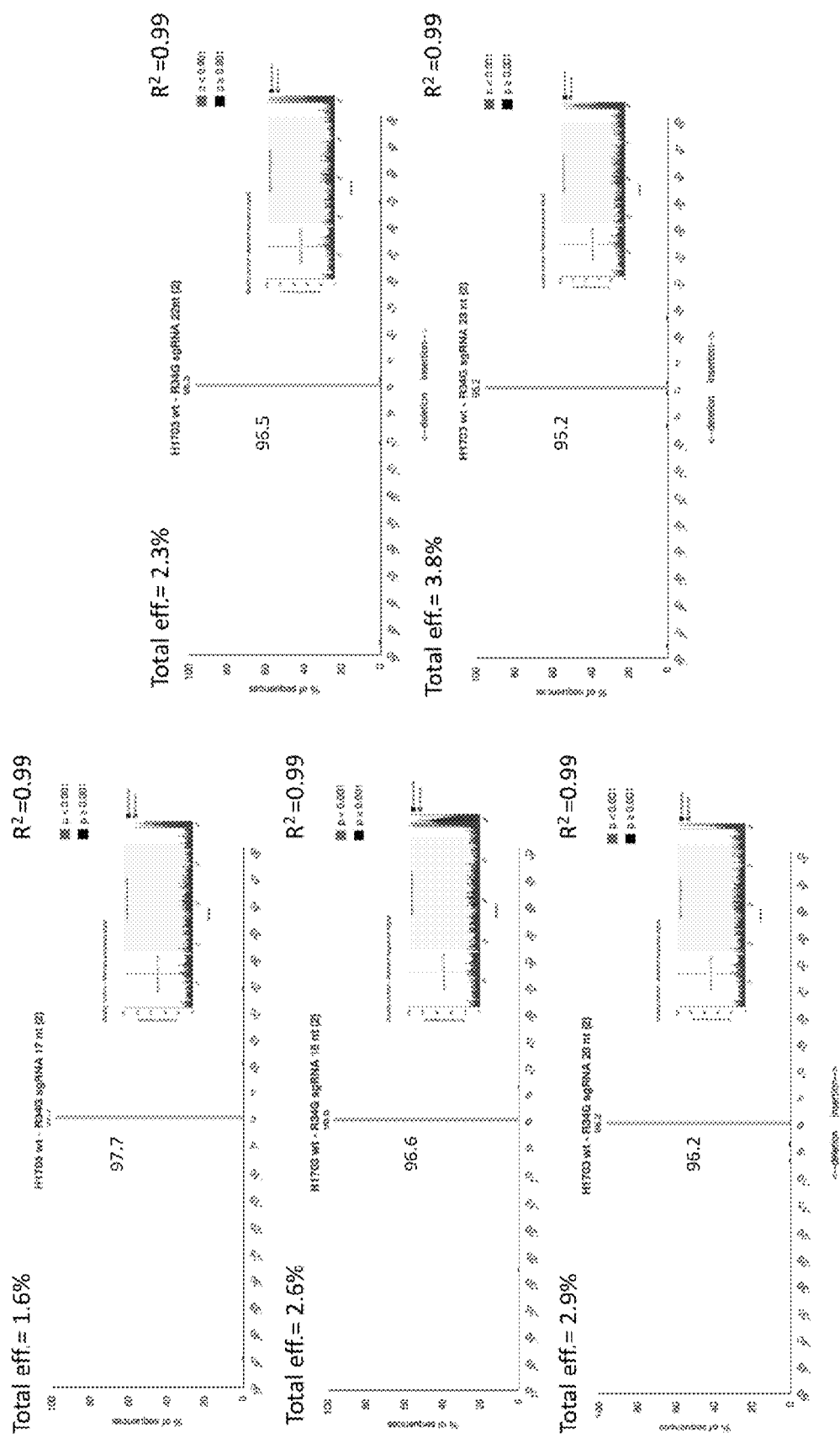
FIG. 14 shows genetic analysis by TIDE for indel efficiency of R34G sgRNA at various lengths—Replicate 2. The H1703 parental cell line was transfected with complexed CRISPR/Cas9 RNP (250 pmol sgRNA to 50 pmol Cas9). After a 72 hour recovery period, a sample for each R34G sgRNA length was collected for genomic DNA isolation, PCR amplification, sanger sequencing and TIDE analysis. This figure shows the genetic analysis by TIDE of replicate 2.

The indel efficiencies of various length sgRNAs from the replicate experiments are displayed in FIGS. 13 and 14. Each gRNA length produced minimal, statistically insignificant indels and total indel efficiency did not exceed 3.8% overall (p value<0.05) as analyzed by TIDE. In both replicates, the 17 nucleotide length sgRNA produced a total indel efficiency of 1.5% and 1.6% with 98.0% and 97.7% of the sequence remaining wildtype. The 18 nucleotide length sgRNA produced a total indel efficiency of 1.9% and 2.6% with 97.4% and 96.6% of the sequence remaining wildtype. The 20 nucleotide length sgRNA produced a total indel efficiency of 0.8% and 2.9% with 98.4% and 96.2% of the sequence remaining wildtype. The 22 nucleotide length sgRNA produced a total indel efficiency of 1.2% and 2.3% with 98.2% and 96.5% of the sequence remaining wildtype. The 23 nucleotide length sgRNA produced a total indel efficiency of 3.4% and 3.8% with 95.8% and 95.2% of the sequence remaining wildtype. As shown by the inset of each graph, every test sample (green bars) was aligned with a control sample (black bars) and the aberrant sequence signal is shown. Each inset shows almost complete overlap of both signals indicating there is very little indel activity in the test sample as indicated by the main graph and total indel efficiency. From this, we can conclude there is high specificity of each sgRNA for its target sequence. Lack of indel activity can be attributed to the missing PAM site in the wildtype sequence, which is required for CRISPR cleavage. The difference in sgRNA length appears to have a minimal impact indel efficiency, with a slight trend towards higher efficiency as length increases, suggesting a longer gRNA may tolerate mismatches more readily and cleave the wildtype "on-target" sequence (summary shown in FIG. 15).

Example 10

A549 Neh2 Knock-Out

The lung adenocarcinoma-derived cell line, A549, was used transfected with CRISPR/Cas9 designed to target exon 2 of NRF2 to create individual clones with random indel patterns. A total of three clones, 1-17, 2-16, and 2-23, were isolated and expanded. All three clones were collected for genomic DNA isolation and sanger sequencing to confirm the indels present. The DECODR program was used to deconvolute the sanger sequencing of each clone. The A549 cell line is polyploid and therefore, these clones contain 3 alleles of the NRF2 gene. Clone 1-17 contains −2, −2, −13 base pair deletions. Clone 2-16 contains a −1 base pair deletion across all alleles. Clone 2-23 contains two wildtype alleles and a −2 base pair deletion. See FIG. 16. A cell proliferation assay was used to assess the functionality of NRF2 after CRISPR targeting in combination with cisplatin treatment. The MTS assay was used to measure cellular proliferation of A549 wildtype, Clone 1-17, 2-16, and 2-23 cells. Cells were plated at the same concentration in each well and allowed to recover for 24 hours. Cells were plated in quadruplets for each concentration of cisplatin tested (0, 1, 2, 3, 5, and 10 μM). Each MTS experiment was performed in duplicate for a total of 8 replicates per clone per concentration. Absorbance values for each clone and concentration were normalized by dividing the absorbance by the absorbance of each control well (0 μM). Normalized values for each clone at each concentration were then averaged across and standard error of the mean was calculated. Averaged normalized values of each concentration were graphed on a scatter graph.

Figure 18:
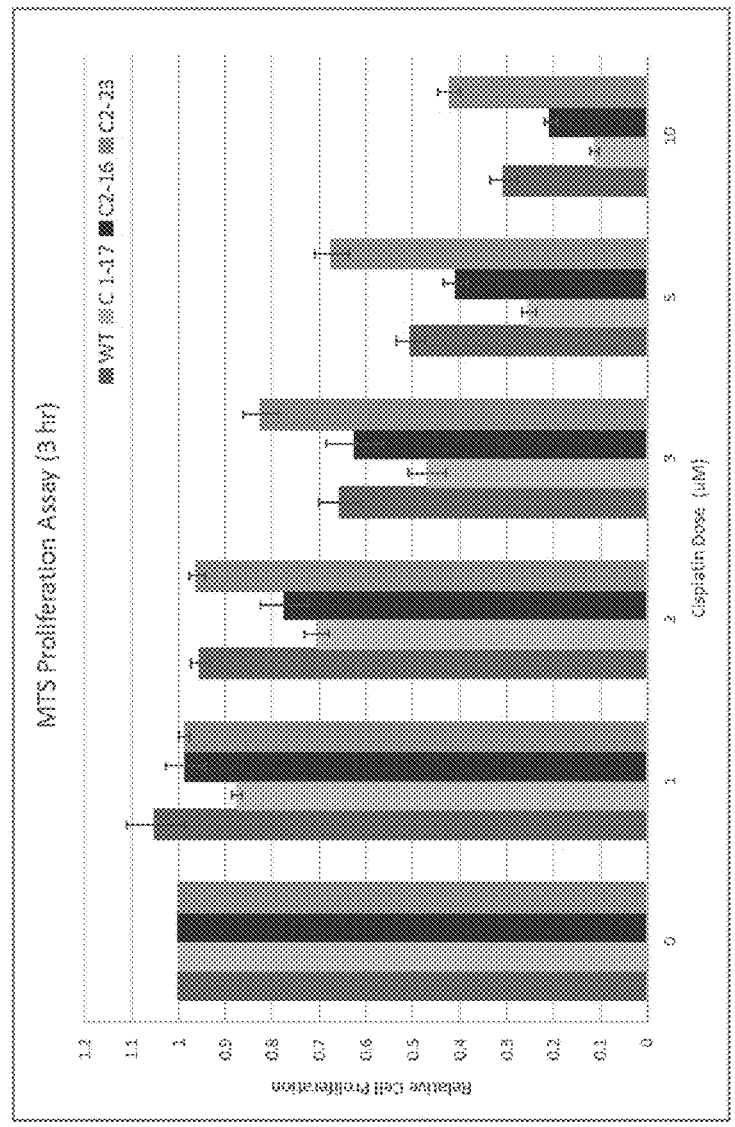

Several A549 NRF2 knockout clones were created and used for dose curves with Cisplatin and Carboplatin (0-10 uM concentration). A single guide RNA was used to target exon 2 of the NRF2 gene to create the NRF2 knockout clones. The A549 clones selected were clones 1-17, 2-16, 2-23. These three were created by targeting NRF2 with a single guide RNA in exon 2, which encodes the Neh2 Domain. Clone 1-17 contains a −2 (62%), −2 318%) and −13 (6%) bp deletion. Clone 2-16 contains a −1 (100%) bp deletion. Clone 2-23 contains two wildtype alleles (79%) and a −2 (21%) bp deletion. These genomic profiles were analyzed by TIDE and DECODR. An MTS assay was used to determine cellular proliferation and chemosensitivty profiles of each NRF2 KO clone. The cells were treated with various concentrations of cisplatin (1, 2, 3, 5, 10 uM) to assess chemosensitivty after different degrees of NRF2 KO. Both FIGS. 17 and 18 contain the normalized and averaged data from two replicates of the experiment, as compared to wildtype A549 cells shown in green shown as a scatter graph and bar graph, respectively. Clone 2-23 contains a predominant wildtype alleles which are causing it to show even higher resistance than the wildtype cells. Clone 1-17 and 2-16 show relatively the same trend of sensitivity as a result of the various indels at the CRISPR cleavage site in exon 2 of the NRF2 gene. There is a gene dose-dependent effect on the sensitivity of the cells to cisplatin after NRF2 knockout. This data mimics the type of response would potentially be seen when targeting cancer cells with CRISPR and chemotherapy.

Example 11

CRISPR-Directed Tumor Cell Selectivity at the DNA Level

When NRF2 is expressed in normal cells, it acts as a tumor suppressor promoting cell survival against oxidative stress. However, when overexpressed in tumor cells, it acts as an oncogene favoring tumor cell survival and protecting against oxidative stress and chemopreventive compounds, thus conferring chemoresistance (Menegon et al., Trends Mol. Med. doi:10.1016/j.molmed.2016.05.002 (2016)). Overexpression of NRF2 can occur as a result of mutations in the KEAP1 and/or NRF2 and are most commonly found in lung cancer. Loss-of-function mutations in KEAP1, found in all of the domains of the protein, interfere with binding of NRF2. Gain-of-function mutations in NRF2 are primarily found in the DLG and ETGE motifs, shown in FIG. 19 (schematic diagram of reported and characterized NRF2 mutations (Frank et al., Clin. Cancer Res. 24:doi:10.1158/1078-0432.CCR-17-3416 (2018); Kerins et al., Sci. Rep. 8:12846 (2018); Menegon et al., Trends Mol. Med. 22:578-93 (2016); Shibata et al., Source 105:13568-73 (2008); Fabrizio et al., Oxid. Med. Cell. Longev. 2018:1-21 (2018); Fabrizio et al., Oxid. Med. Cell. Longev. 2018:2492063 (2018); Fukutomi et al., Mol. Cell. Biol. 34:832-46 (2014)), which are responsible for binding to KEAP1. These mutations exclusively interfere with the protein-protein interactions between KEAP1 and NRF2, causing overexpression of NRF2 in tumor cells. This overexpression of NRF2 alters its function from a tumor suppressor to an oncogene through the accumulation and lack of degradation of the protein. With the loss of KEAP1 binding, NRF2 is no longer sequestered for degradation causing accumulation of the protein in the cytoplasm and nucleus, in turn conferring cyto-protection and detoxifications through activation of downstream pathways.

Recently, a study by Kerins and Ooi in Scientific Reports, catalogued somatic NRF2 mutations in various cancer cases reported in The Cancer Genome Atlas (Kerins et al., Sci. Rep. 8:12846 (2018)). The study identified the percentage of NRF2 and KEAP1 mutations found across 33 different tumor types as well as the common mutations responsible for constitutive NRF2 activation. They reported 214 cases of NRF2 mutations, predominantly seen in Lung Squamous Cell Carcinoma (LUSC). Several of these NRF2 mutations have been reported and characterized previously and are shown in FIG. 19. Of these 214 cases, the most common mutation reported in LUSC is R34G. The R34G mutation has been characterized to inhibit KEAP1-mediated degradation of NRF2 causing increased NRF2 stability and nuclear accumulation (Kerins et al., Sci. Rep. 8:12846 (2018); Fabrizio et al., Oxid. Med. Cell. Longev. 2018:2492063 (2018)). The R34G mutation occurs as a result of a base change from cytosine to guanine in the first base of codon 34 in NRF2 (CGA→GGA), which changes the amino acid from arginine to glycine. This mutation is especially of interest from a CRISPR-directed gene editing approach because this mutation creates a new Protospacer Adjacent Motif (PAM) site for Cas9 recognition, binding and cleavage (FIG. 20). The PAM consists of 2-6 nucleotides adjacent to the CRISPR seed sequence and allows the Cas nuclease protein to recognize, bind and cleave the target DNA. The Cas9 nuclease recognizes 5' NGG 3' where N can be any nucleotide. After cleavage, Cas9 creates blunt-end, double-stranded breaks which are then repaired by one of two mechanisms: non-homologous end joining (NHEJ) or homology-directed repair (HDR). NHEJ is responsible for insertions or deletions (indel) at the cut site, generating genetic knockouts (KO) of the gene and potentially causing loss of protein expression. Differential Cas9 recognition sites such as this could be the basis for selective cleavage of the tumor cell genome. There are several other NRF2 mutations that have been reported and characterized that would be applicable for this approach. Those mutations are presented in FIG. 19 in magenta with the red base indicating the nucleotide that is mutated to create a new Cas9 PAM site.

Mutations in the DLG motif have been shown to disrupt intramolecular interactions inhibiting KEAP1 binding (Fukutomi et al., Mol. Cell. Biol. 34:832-46 (2014)). More recently, Kerins and Ooi investigated the nature of the R34G mutation in NRF2 and found the mutation itself increased protein stability. Therefore, due to the nature of the R34G mutation, it should only be present in cancerous cells allowing for the differentiation of tumor genomic DNA from normal genomic DNA. This approach also improves the delivery method and specificity of delivery. The guide RNA (gRNA) that would be used to target the R34G mutation with CRISPR/Cas9 is: 5' GATATAGATCTTGGAGTAAGT GG 3' (bold—PAM site, underlined—R34G mutation (SEQ ID NO:25)). Several experiments have been conducted to assess the level of discrimination and specificity of the R34G mutation-specific CRISPR/Cas9 complex.

As proof of concept, an in vitro cleavage reaction was conducted to assess the level of discrimination using the R34G guide RNA in a ribonucleoprotein complex (RNP). The in vitro cleavage reaction encompasses complexing target specific-guide RNA with Cas9 protein to form a ribonucleoprotein (RNP). The RNP is incubated with DNA of interest (100 ng) and the reaction and cleavage products are visualized by gel electrophoresis. For this experiment, wildtype and R34G-mutated NRF2 PCR products (901 bp) from an NRF2 expression plasmid (FIG. 21) were incubated with R34G-targeting RNP complex (1 µM) and cleavage products were visualized by gel electrophoresis, shown in FIG. 22. A nonspecific RNP (HBB RNP) was also used to demonstrate the specificity of the new site and its targeting RNP. In lane 6 of the gel image (R34G NRF2-R34G RNP), two new bands (222 & 679 bp) are seen as a result of RNP cleavage, indicating the R34G-targeting RNP only recognizes and cleaves the mutated DNA sequence.

After the initial proof of concept, in vivo experiments were conducted to further assess specificity and efficacy. Initial in vivo studies were conducted in the A549 cell line, derived from a human lung adenocarcinoma. The A549 cell line was genetically engineered to contain the R34G mutation in the NRF2 gene. The work conducted in the A549 cell lines is also being conducted in the H1703 cell line, which is derived from a human lung squamous cell carcinoma. The parental A549 cell line, R34G-mutated A549 cell line (A549 R34G-6) and H1703 parental cell line were sequenced across exon 2. Both A549 and H1703 parental cell lines contain no mutations within exon 2 of the NRF2 gene, whereas, the A549 R34G-6 cell line contains a heterozygous R34G mutation (FIG. 23). The A549 cell line is known to be bi- and tri-allelic, therefore, the R34G mutation in the A549 R34G-6 clone is believed to be on two of three alleles as seen by the double peak of the 'G' nucleotide (black peak) as compared to the peak of the 'C' nucleotide (blue peak), indicated by the red arrow (FIG. 23).

Once the sequences were verified, genomic DNA from each cell line was used to amplify exon 2 of NRF2. The PCR products (530 bp) from each cell line were then used in in vitro cleavage reactions under various parameters to test specificity and fidelity of the R34G-targeting RNP. For these cleavage reactions, expected cleavage products would appear at 385 and 145 bp as indicated by the red lines along the ladder, with uncut product appearing at 530 bp. FIG. 24 depicts the gel image from an in vitro cleavage reaction using wildtype NRF2 sequence from parental A549 cells and R34G-mutated NRF2 sequence from the A549 R34G-6 cells. An increasing concentration (0.5-5 pmol) of R34G-targeting RNP was used to determine the threshold and fidelity of the sequence. The gel image shows that 5× the standard concentration of RNP used does not result in cleavage of wildtype NRF2 sequence (lanes 2-5), whereas with a R34G-mutated NRF2 sequence, cleavage products can be seen even with half of the standard concentration (lane 7) of the R34G-targeting RNP. Uncut product (top band, 530 bp) can still be seen in lanes 7-10, which corresponds to the heterozygosity of the R34G mutation in the A549 R34G-6 cell line. Therefore, the wildtype NRF2 allele in the A549 R34G-6 cell line acts as an internal negative control.

Another in vitro cleavage reaction was conducted to assess the cleavage efficiency of the wildtype NRF2 sequence to ensure the R34G-targeting RNP was, in fact, not cleaving the wildtype NRF2 sequence because of the lack of the R34G mutation. A guide RNA with a cut site 29 bp upstream (labeled Neh2 RNP) from the R34G RNP cut site was selected and used as a positive cleavage control. The results of the in vitro cleavage reaction using both RNPs is displayed in the gel image in FIG. 25. Lanes 1-8 were reactions using wildtype NRF2 sequence while lanes 9-16 were reactions using R34G-mutated NRF2 sequence. In lanes 2-4 and 10-12, PCR products were incubated with increasing concentrations (1, 3 & 5 pmol) of RNP targeting the beginning of exon 2 (Neh2 RNP). The Neh2 guide RNA sequence is: 5' TGGATTTGATTGACATACTTTGG 3' (SEQ ID NO:13) which is a native CRISPR site and used as the positive control for cleavage for these reactions. The cleavage products using Neh2 RNP are 116 and 414 bp and can be seen in both wildtype and R34G-mutated NRF2 sequences, indicating both wildtype and R34G-mutated NRF2 sequences are amenable to CRISPR/Cas9 cleavage within the target region. In lanes 6-8 and 14-16, PCR products were incubated with increasing concentrations (1, 3 & 5 pmol) of R34G-targeting RNP. The cleavage products are 145 and 385 bp and can be seen clearly in lanes 14-16 with minimal cleavage seen in lanes 6-8 of the wildtype NRF2 sequence. This further reinforces the specificity of the R34G-targeting RNP only recognizing the target DNA in the presence of the R34G mutation in exon 2 of NRF2. The residual cleavage of the wildtype NRF2 sequence can be explained by the nature of the cleavage reaction and sequence homology of the guide RNA to the target DNA. The parameters of the cleavage reaction include incubating target DNA with RNP for an hour for maximum cleavage. Therefore, the nature of this reaction may induce nonspecific cleavage.

The last in vitro cleavage reaction before moving to in vivo studies was conducted using genomic DNA and NRF2 exon 2 PCR products from the H1703 and A549 parental cell lines, which contain wildtype NRF2, and the A549 R34G-6 cell line, which contains R34G-mutated NRF2 (FIG. 26). The R34G-targeting RNP was used in increasing concentrations (1 & 5 pmol) with each PCR product (lanes 2, 3, 5, 6, 8, 9). There is minimal cleavage seen with wildtype NRF2 sequence in both the H1703 and A549 parental cell lines (lanes 3 & 6), whereas cleavage products (145 & 385 bp) are clearly seen in the A549 R34G-6 cell line with the R34G-mutated NRF2 sequence (lanes 8 & 9). Again, this data reinforces the specificity and efficacy of the R34G-targeting RNP as shown in the data presented in the previous figures.

The in vitro cleavage reactions were further assessed through cell based-experiments using the same cell lines: A549 and H1703 parental cell lines and the A549 R34G-6 cell line. The cell lines were cultured under the standard conditions and transfected by electroporation (Lonza, Nucleofection) using previously established parameters. FIGS. 27-29 depict the genetic analysis of eight separate experiments using all three cell lines after transfection of the R34G-targeting RNP. This experiment was conducted under three different conditions. The first condition was using an equimolar concentration of duplexed guide RNA to Cas9. The second condition was using five times the amount of duplexed guide RNA to Cas9, along with using a GFP (Green Fluorescent Protein) expression vector to measure transfection efficiency and to sort the GFP-positive population for further analysis. The third condition was using five times the amount of single guide RNA to Cas9, along with the GFP expression vector and sorting of the GFP-positive population for further analysis.

FIG. 27 depicts the genetic analysis after transfection of the R34G-targeting RNP in the A549 parental cells. The A549 parental cells contain a wildtype NRF2 gene therefore there is no native CRISPR/Cas9 recognition site for the R34G-targeting RNP. Genomic DNA from the transfected cells was analyzed by TIDE analyses (shown in FIG. 27). The top panel displays indel efficiency and sequence alignment of an unsorted population. According to TIDE analysis, there is a total indel efficiency of 11.8% and statistically insignificant insertions and deletions (black bars-p value>0.001). The middle panel shows a total indel efficiency of 4.3% from a GFP-positive sorted population with only statistically insignificant insertions or deletions. The bottom panel shows a total indel efficiency of 11.4% from a GFP-positive sorted population with one statistically significant insertion (+1 bp).

FIG. 28 depicts the genetic analysis after transfection of the R34G-targeting RNP in the A549 R34G-mutated clonal cell line (A549 R34G-6). The A549 R34G-6 cells contain a heterozygous R34G mutation in exon 2 of the NRF2 gene, creating a new CRISPR recognition site for the R34G-targeting RNP. Genomic DNA from transfected cells was analyzed for gene editing activity by TIDE analysis (shown in FIG. 28). The top panel shows indel efficiency and sequence alignment of an unsorted population with a total indel efficiency of 43.0% and statistically significant insertions (+1, 30 bp) and deletions (−9, 41 bp) along with several insignificant deletions. The middle panel shows a total indel efficiency of 55.7% from a GFP-positive sorted population with statistically significant insertions (+1, 30 bp) and deletions (−1, 9 bp) and insignificant deletions. The significant total indel efficiency indicates the R34G-targeting RNP is very active. Since this clonal cell line is heterozygous for the R34G mutation and contains one wildtype NRF2 allele, we would expect ⅓ of the sequence to remain wildtype (displayed at the 0 tick mark), which is seen in this experimental data (32.0% of the sequence analyzed is wildtype). The bottom panel shows a total indel efficiency of 32.7% with significant insertions (+1, 30 bp) and deletions (−2 bp) and insignificant indels from a GFP-positive sorted population. The lower R2 value indicates some of the sequence analysis is unaccounted for likely because of sequence quality. Overall from this data, we can infer that the R34G mutation does in fact create a new CRISPR recognition site that is actively cleaved when tested in cell-based experiments. Although only a speculation, the R34G-targeting RNP does differentiate between the wildtype and R34G-mutated alleles within the clonal cell line.

FIG. 29 depicts the genetic analysis after transfection of the R34G-targeting RNP in the NCI-H1703 cell line, which contains a wildtype NRF2 gene and no native CRISPR recognition site. Genomic DNA from transfected cells was analyzed for gene editing activity by TIDE analyses (shown in FIG. 29). The top panel shows total indel efficiency of 0.0% from an unsorted population. The bottom panel shows total indel efficiency of 4.6% with only insignificant indels from a GFP-sorted population.

Further studies include engineering the H1703 cell line to contain the R34G mutation to be used as a model system for Lung Squamous Cell Carcinoma in downstream experiments. This will be done by transfecting a CRISPR/Cas9 ribonucleoprotein (RNP) designed to cleave within exon 2 of the NRF2 gene, which contains the Neh2 Domain. A single stranded oligonucleotide (ssODN) containing the R34G mutation will serve as a template strand to bridge the double-strand break. The RNP and ssODN will be transfected via electroporation (Nucleofection, Lonza) and transfected cells will be sorted by fluorescence activated single cell sorting (FACS) for clonal expansion and sequence analysis. Once a R34G mutated-H1703 cell line is established, we will test the specificity and efficiency of the R34G-targeting CRISPR/Cas9 (5' GATATAGATCTTG-GAGTAAGTGG 3' (SEQ ID NO:25)) on the new mutated cell line using several cell-based experiments and a xenograft mouse model. We will assess gene editing activity of the R34G-targeting RNP by analyzing the cleavage site for indel formation (TIDE analysis, Desktop Genetics website) after transfection of the R34G mutated-H1703 cell line with the R34G-targeting RNP. Cells will be harvested after transfection, sequenced and analyzed. We will also assess the specificity of the R34G-targeting RNP in the parental cell line to determine the degree of recognition of the wildtype NRF2 sequence. Experiments will be repeated to ensure reproducibility. To mimic experiments in the xenograft mouse model, cellular proliferation and cell viability experiments will be conducted to assess the effect of NRF2 knockout following R34G-targeting with CRISPR/Cas9. To do so, cell proliferation and cell viability will be measured by Ki67 staining and MTS assay. Experiments will be repeated with cisplatin treatment as a condition to further assess sensitivity of these cells following R34G-targeting.

The invention claimed is:

1. A method of reducing variant NRF2 expression or activity in a cancer cell comprising introducing into the cancer cell (a) one or more DNA sequences encoding one or more guide RNAs (gRNAs) that are complementary to one or more target sequences in a variant NRF2 gene and (b) a nucleic acid sequence encoding a Clustered Regularly Interspaced Short Palindromic Repeat (CRISPR)-associated endonuclease, whereby the one or more gRNAs hybridize to the variant NRF2 gene and the CRISPR-associated endonuclease cleaves the variant NRF2 gene, and wherein NRF2 expression or activity is reduced in the cancer cell relative to a cancer cell in which the one or more DNA sequences encoding the one or more gRNAs and the nucleic acid sequence encoding the CRISPR-associated endonuclease are not introduced;

[I] wherein a variant NRF2 polypeptide encoded by the variant NRF2 gene in the cancer cell comprises one or more amino acid substitutions of (i) V32G, R34G, F71S, E79G, or E185D relative to SEQ ID NO:8;

(ii) V32G, R34P, F71S, E79G, or E185D relative to SEQ ID NO:8;

(iii) Q26P, V32G, R34G, F71S, E79G, or E185D relative to SEQ ID NO:8;

(iv) Q26P, V32G, R34P, F71S, E79G, or E185D relative to SEQ ID NO:8; or

[II] wherein the variant NRF2 gene comprises:

(a) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:52 substituting positions 728-706 of the reverse complement of SEQ ID NO:7, or SEQ ID NO:57 substituting positions 360-381 of SEQ ID NO:7;

(b) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:52 substituting positions 728-706 of the reverse complement of SEQ ID NO:7, or SEQ ID NO:57 substituting positions 360-381 of SEQ ID NO:7;

(c) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:52 substituting positions 728-706 of the reverse complement of SEQ ID NO:7, or SEQ ID NO:57 substituting positions 360-381 of SEQ ID NO:7;

(d) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:52 substituting positions 728-706 of the reverse complement of SEQ ID NO:7, or SEQ ID NO:57 substituting positions 360-381 of SEQ ID NO:7;

(e) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7;

(f) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7;

(g) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7, or (h) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7.

2. The method of claim 1, wherein the one or more gRNAs are complementary to a target sequence in exon 2 of the variant NRF2 gene.

3. The method of claim 1, wherein the one or more gRNAs comprise a trans-activated small RNA (tracrRNA) and a CRISPR RNA (crRNA).

4. The method of claim 1, wherein the one or more gRNAs are one or more single guide RNAs.

5. The method of claim 1, wherein the CRISPR-associated endonuclease is a class 2 CRISPR-associated endonuclease.

6. The method of claim 5, wherein the class 2 CRISPR-associated endonuclease is Cas9 or Cas12a.

7. The method of claim 1, wherein expression of one or more allele(s) of the variant NRF2 gene is reduced in the cancer cell.

8. A method of reducing variant NRF2 expression or activity in a cancer cell comprising introducing into the cancer cell (a) one or more guide RNAs (gRNAs) that are complementary to one or more target sequences in the variant NRF2 gene and (b) a Clustered Regularly Interspaced Short Palindromic Repeat (CRISPR)-associated endonuclease, whereby the one or more gRNAs hybridize to the variant NRF2 gene and the CRISPR-associated endonuclease cleaves the variant NRF2 gene, and wherein variant NRF2 expression or activity is reduced in the cancer cell relative to a cancer cell in which the one or more gRNAs and the CRISPR-associated endonuclease are not introduced,

[I] wherein a variant NRF2 polypeptide encoded by the variant NRF2 gene in the cancer cell comprises one or more amino acid substitutions of
   (i) V32G, R34G, F71S, E79G, or E185D relative to SEQ ID NO:8;
   (ii) V32G, R34P, F71S, E79G, or E185D relative to SEQ ID NO:8;
   (iii) Q26P, V32G, R34G, F71S, E79G, or E185D relative to SEQ ID NO:8;
   (iv) Q26P, V32G, R34P, F71S, E79G, or E185D relative to SEQ ID NO:8; or

[II] wherein the variant NRF2 gene comprises:
   (a) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:52 substituting positions 728-706 of the reverse complement of SEQ ID NO:7, or SEQ ID NO:57 substituting positions 360-381 of SEQ ID NO:7;
   (b) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:52 substituting positions 728-706 of the reverse complement of SEQ ID NO:7, or SEQ ID NO:57 substituting positions 360-381 of SEQ ID NO:7;

(c) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:52 substituting positions 728-706 of the reverse complement of SEQ ID NO:7, or SEQ ID NO:57 substituting positions 360-381 of SEQ ID NO:7;

(d) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:52 substituting positions 728-706 of the reverse complement of SEQ ID NO:7, or SEQ ID NO:57 substituting positions 360-381 of SEQ ID NO:7;

(e) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7;

(f) one or more polynucleotide sequences selected from the group consisting of SEQ ID NO:41 substituting positions 205-227 of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7;

(q) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:45 substituting positions 230-252 of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7; or (h) one or more polynucleotide sequences selected from the group consisting of SEQ ID NO:42 substituting positions 249-227 of the reverse complement of SEQ ID NO:7, SEQ ID NO:43 substituting positions 215-237 of SEQ ID NO:7, SEQ ID NO:44 substituting positions 224-246 of SEQ ID NO:7, SEQ ID NO:46 substituting positions 273-251 of the reverse complement of SEQ ID NO:7, SEQ ID NO:47 substituting positions 385-363 of the reverse complement of SEQ ID NO:7, SEQ ID NO:48 substituting positions 398-376 of the reverse complement of SEQ ID NO:7, SEQ ID NO:49 substituting positions 366-388 of SEQ ID NO:7, SEQ ID NO:50 substituting positions 411-389 of the reverse complement of SEQ ID NO:7, SEQ ID NO:58 substituting positions 374-396 of SEQ ID NO:7, SEQ ID NO:52 substituting positions 728-706 of the reverse complement of SEQ ID NO:7, or SEQ ID NO:57 substituting positions 360-381 of SEQ ID NO:7.

\* \* \* \* \*